(12) United States Patent
Sanders et al.

(10) Patent No.: US 11,793,835 B2
(45) Date of Patent: Oct. 24, 2023

(54) METHODS OF USING RARγ AGONISTS FOR CANCER TREATMENT

(71) Applicant: Io Therapeutics, Inc., Spring, TX (US)

(72) Inventors: Martin E. Sanders, Spring, TX (US); Vidyasagar Vuligonda, Lake Forest, CA (US)

(73) Assignee: Io Therapeutics, Inc., Spring, TX (US)

( * ) Notice: Subject to any disclaimer, the term of this patent is extended or adjusted under 35 U.S.C. 154(b) by 0 days.

(21) Appl. No.: 17/993,528

(22) Filed: Nov. 23, 2022

(65) Prior Publication Data

US 2023/0095368 A1    Mar. 30, 2023

Related U.S. Application Data

(60) Provisional application No. 63/282,547, filed on Nov. 23, 2021.

(51) Int. Cl.
*A61K 35/17*    (2015.01)
*A61P 35/00*    (2006.01)
*C07C 251/48*    (2006.01)
*C07D 307/81*   (2006.01)

(52) U.S. Cl.
CPC .............. *A61K 35/17* (2013.01); *A61P 35/00* (2018.01); *C07C 251/48* (2013.01); *C07D 307/81* (2013.01)

(58) Field of Classification Search
CPC ....... A61K 35/17; A61P 35/00; C07C 251/48; C07D 307/81
See application file for complete search history.

(56) References Cited

U.S. PATENT DOCUMENTS

| | | | |
|---|---|---|---|
| 5,071,773 A | 12/1991 | Evans et al. | |
| 5,298,429 A | 3/1994 | Evans et al. | |
| 9,907,768 B2 * | 3/2018 | Chandraratna | .... A61K 39/3955 |
| 10,213,401 B2 * | 2/2019 | Chandraratna | ........ A61K 39/39 |
| 10,471,030 B2 * | 11/2019 | Chandraratna | ...... C12N 5/0638 |
| 2007/0185055 A1 | 8/2007 | Jiang et al. | |
| 2008/0300312 A1 | 12/2008 | Chandraratna et al. | |
| 2018/0338940 A1 * | 11/2018 | Chandraratna | .... A61K 31/5513 |
| 2019/0015363 A1 | 1/2019 | Chandraratna et al. | |
| 2020/0390736 A1 | 12/2020 | Sanders et al. | |

OTHER PUBLICATIONS

Windschwendter (Windschwendter, et al., Int. J. Cancer 1997 71:497-504) (Year: 1997).*
Perri et al. "BCL-xL/MCL-1 inhibition and RARγ antagonism work cooperatively in human HL60 leukemia cells", Exp Cell Res. 327(2):183-191, 2014.
Meister et al. (Anticancer Res. 18(3A):1777-1786, 1998).
Cheung et al. (Biochem Biophys Res Commun. 229(1):349-54, 1996).
Raffo et al. (Anticancer Res. 20(3A):1535-43, 2000).

* cited by examiner

*Primary Examiner* — Julie Wu
*Assistant Examiner* — John L Van Druff
(74) *Attorney, Agent, or Firm* — K&L Gates LLP; Louis C. Cullman; Michelle Glasky Bergman

(57) ABSTRACT

The invention discloses novel RAR gamma selective agonists used in the treatment of cancer. The invention also discloses administration of RAR gamma selective agonists to mammals, including humans for the purpose of selectively activating RAR gamma receptor and treat cancer by way of activating tumor infiltrating lymphocytes.

17 Claims, 23 Drawing Sheets

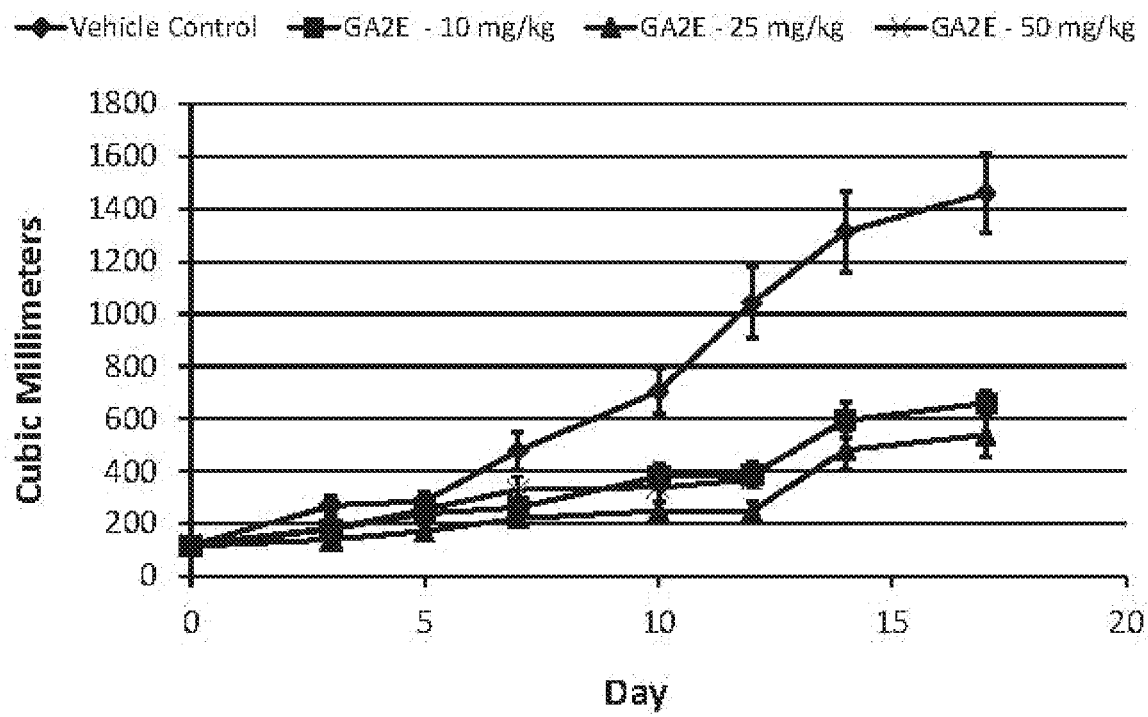
Figure 7
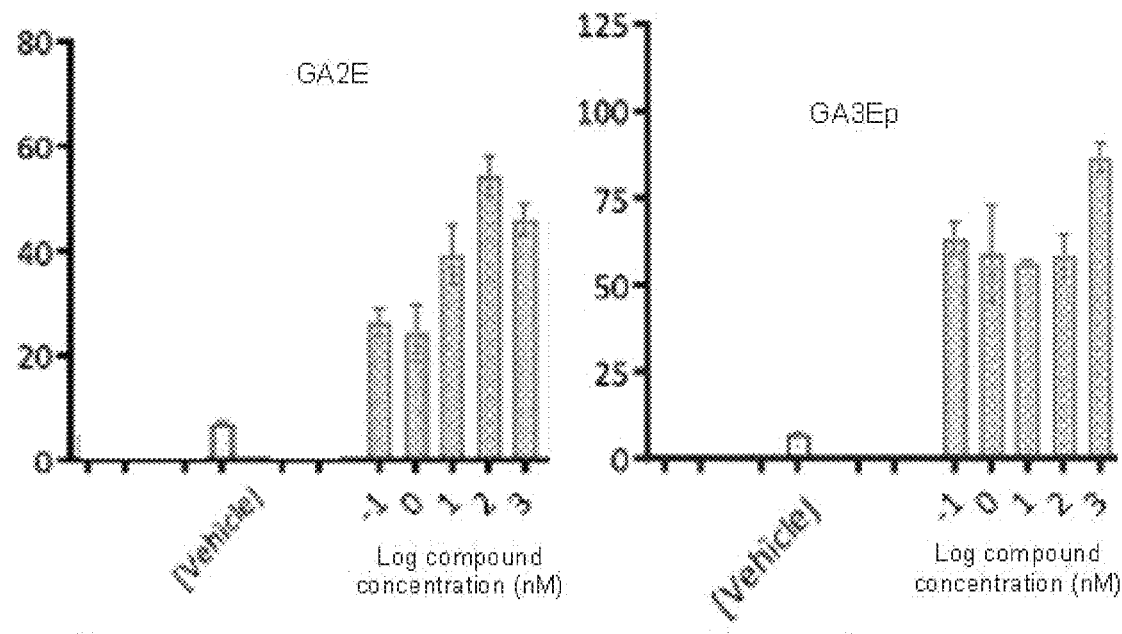
Figure 8A
Figure 8B

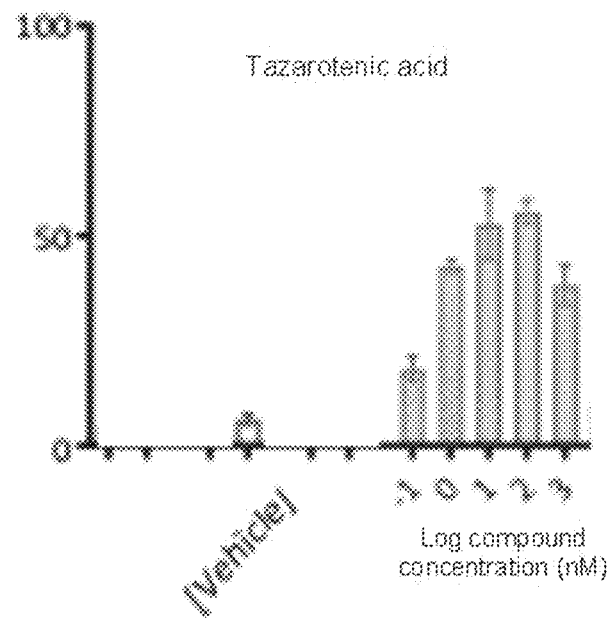
Figure 8C
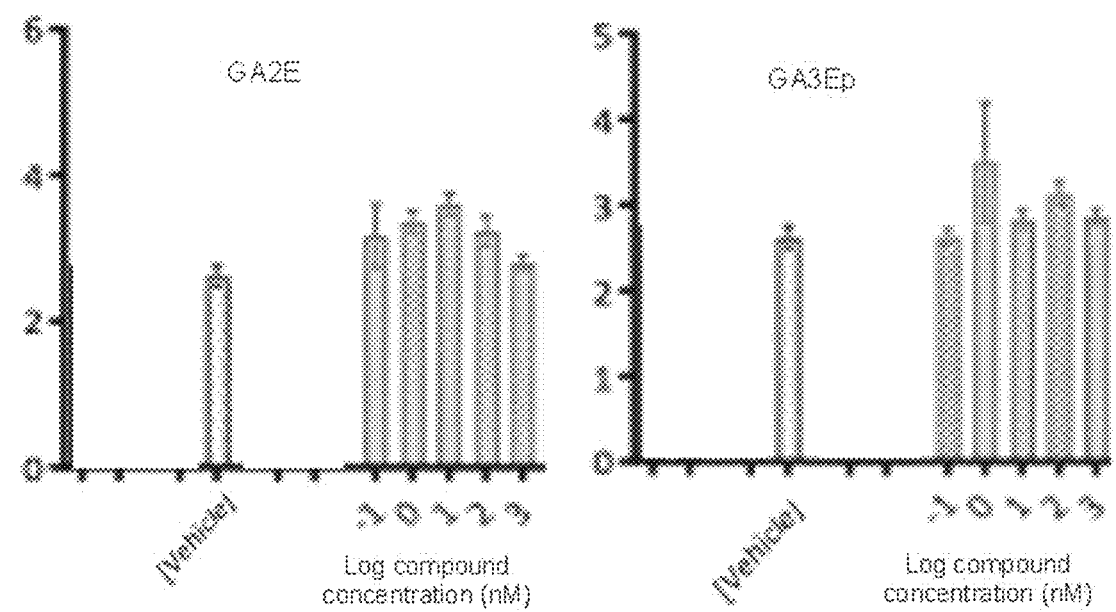
Figure 9A
Figure 9B

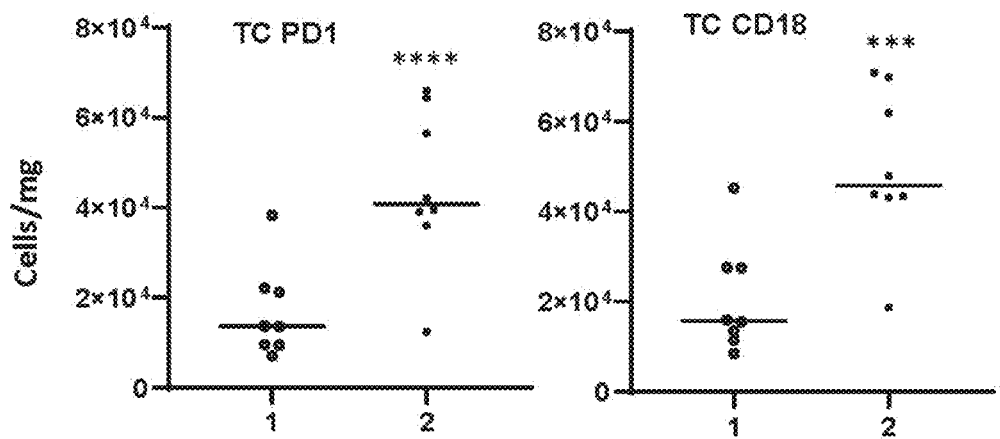
Figure 13A
Figure 13B
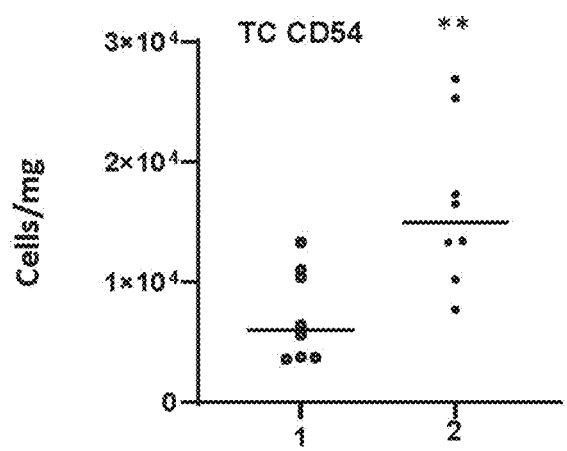
Figure 13C

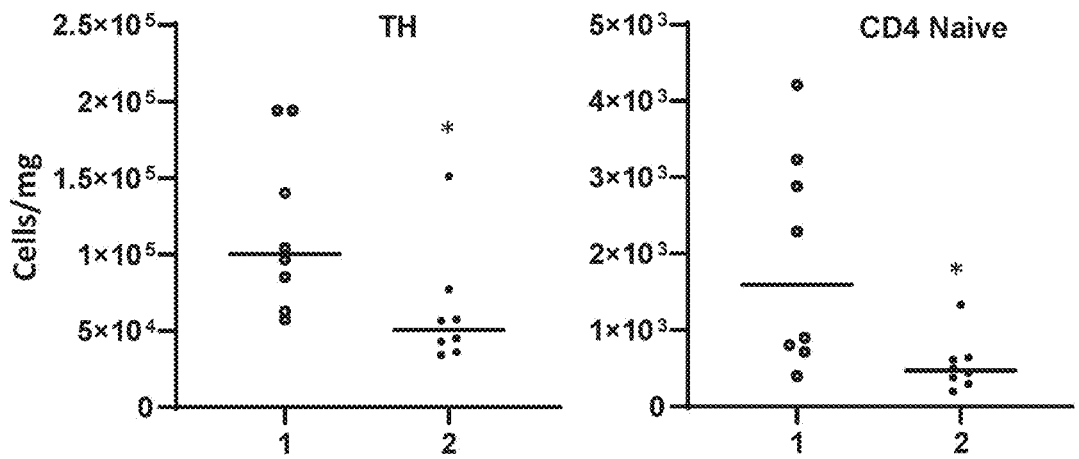
Figure 14A
Figure 14B
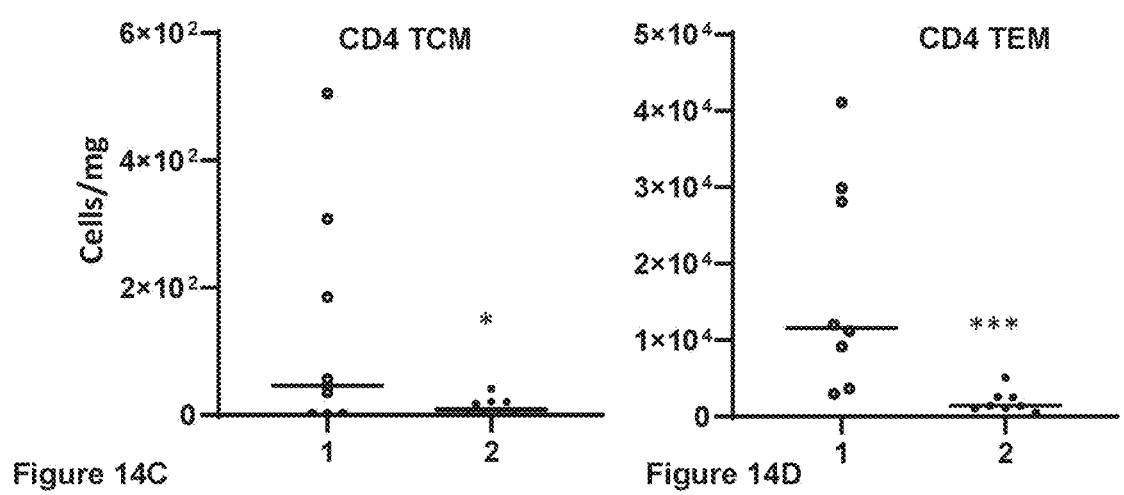
Figure 14C
Figure 14D
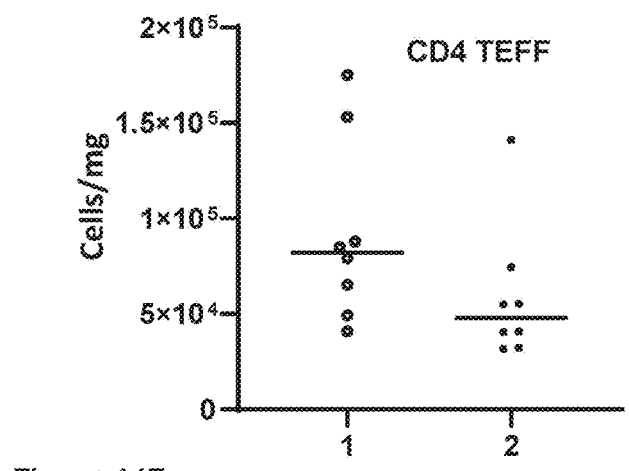
Figure 14E

METHODS OF USING RARγ AGONISTS FOR CANCER TREATMENT

CROSS REFERENCE TO RELATED APPLICATIONS

The present application claims the benefit of U.S. Provisional Patent Application 63/282,547 filed Nov. 23, 2021, the entire contents of which is incorporated by reference herein.

FIELD

The present disclosure relates to methods of treating cancer with RARγ agonists.

BACKGROUND

Retinoids are a class of small molecules that interact with the nuclear receptors retinoic acid receptor (RAR) and retinoid X receptor (RXR). Retinoids that interact with RXR are termed rexinoids and, in some contexts, the term retinoid is used to indicate a compound that interacts with RAR. Both RAR and RXR have three subtypes, α, β, and γ. Retinoids can act as either agonists or antagonists of these receptors. Some retinoids interact with both RAR and RXR and with each of the subtypes, while others will preferentially or specifically interact with a particular receptor type or subtype(s). Retinoids regulate development and the differentiation of multiple types of cells. Retinoids have pleotropic effects depending, in part, on the particular receptor types and subtypes that a particular retinoid activates or inhibits. Retinoids exhibit a degree of structural diversity. It is not possible to reliably predict which receptor type and subtype a particular retinoid will interact with or whether it will act as an agonist or antagonist.

Further uncertainty about what can be expected from a particular subtype of retinoid arises from a degree of inconsistency in the scientific literature as to what effects may be observed. In tissue culture studies of a leukemic cell line Perri et al. (*Exp Cell Res.* 327(2):183-191, 2014) found that a RARα agonist and a RARγ antagonist each inhibited proliferation, and that a combination of the RARγ antagonist and a dual antagonist of BCL-$x_L$ and MCL-1 was profoundly inhibitory. In contrast, Meister et al. (*Anticancer Res.* 18(3A):1777-1786, 1998) found RARγ agonists had the greatest antiproliferative effect against a neuroblastoma cell line. In both studies apoptosis was seen as the primary mechanism of inhibiting tumor cell proliferation. Cheung et al. (*Biochem Biophys Res Commun.* 229(1):349-54, 1996) studied the effects of RAR subtype specific agents by transfecting a neuroblastoma cell line with each individual RAR subtype and concluded the RARβ expression was necessary for growth inhibition. Raffo et al. (*Anticancer Res.* 20(3A):1535-43, 2000) observed some apoptotic activity against breast cancer cell lines by agonists of all three subtypes, but the greatest effect from RARα agonists. As compared to these in vitro experiments, what effects any of these compounds may have in vivo, where the whole panoply of pleiotropic effects would be in play, is even less clear.

Treatments for cancer are ever evolving, gaining in specificity and sophistication. Early non-surgical cancer treatments generally targeted rapidly dividing cells which were more sensitive to radiological and chemical assault. Over time, more specific and less generally toxic treatments have been developed. Some treatments appear to have broad applicability, for example immune checkpoint inhibitors. Others are targeted to cancers that express a particular antigen or other biomarker involved in the regulation of proliferation or differentiation; including many monoclonal antibodies and kinase inhibitors. Yet as the variety of cancer treatments has grown, it has become ever harder to determine which candidate treatments might be productively pursued and for what indications.

SUMMARY

Disclosed herein are methods of expanding tumor-infiltrating lymphocytes (TIL) in vitro and associated methods treating cancer by administering an effective amount of a RARγ selective agonist and/or expanded TIL to a subject in need thereof.

One aspect is a method of treating cancer comprising administering, to a patient in need thereof, an effective amount RARγ-selective agonist having the structure

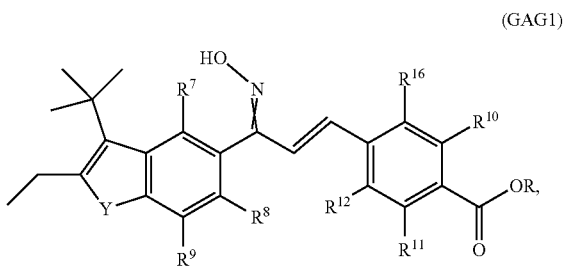

(GAG1)

or a pharmaceutically acceptable salt thereof, wherein R is H or $C_{1-6}$ alkyl, and the crossed double bond to the =N—OH group indicates that stereochemistry is not specified. However, in some embodiments, the E configuration of the =N—OH group is preferred. $R^7$ to $R^{12}$ are independently: $C_{1-6}$ alkyl, a hydrogen atom, an alkoxy group, a halogen atom (for example F, Cl, or Br), a nitro group, a hydroxy group, $OCF_3$, or $COR^{13}$, where $R^{13}$ is $C_{1-6}$ alkyl or $CF_3$. Y is oxygen, sulfur, or $NR^{14}$, where $R^{14}$ is $C_{1-6}$ alkyl. $R^{16}$ is H or F.

In some embodiments, the RARγ-selective agonist has the structure

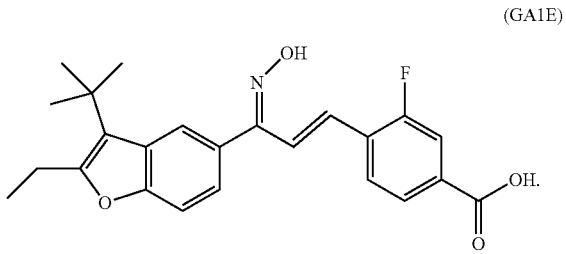 [SMILES: CCc1oc2ccc(C(/C=C/c3ccc(C(=O)O)cc3F)=N/O)cc2c1C(C)(C)C]

(GA1E)

One aspect is a method of generating, differentiating, or expanding the number of TIL by contacting them with a RARγ selective agonist. In some embodiments, contacting comprises culturing the TIL in vitro in a media supplemented with the RARγ selective agonist. In some embodiments, contacting comprises administering the RARγ selective agonist to a subject having a tumor.

With respect to the above aspects, in some embodiments, the RARγ selective agonist is selective in that it has no or negligible agonistic activity for RARα at clinically relevant concentrations. In some embodiments the RARγ selective agonist is selective in that it has no or negligible agonistic activity for both RARα and RARβ at clinically relevant concentrations.

In some embodiments, the RARγ selective agonist is a compound of structure (GAG1)

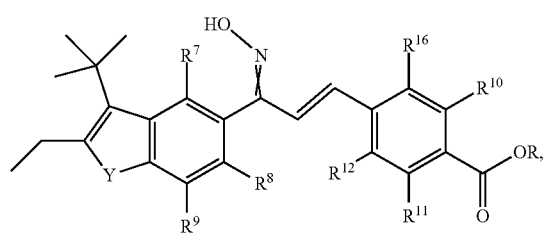

or a pharmaceutically acceptable salt thereof, wherein R is H or $C_{1-6}$ alkyl, and the crossed double bond to the =N—OH group indicates that stereochemistry is not specified. However, in some embodiments, the E configuration of the =N—OH group is preferred. $R^7$ to $R^{12}$ are independently: $C_{1-6}$ alkyl, a hydrogen atom, an alkoxy group, a halogen atom (for example F, Cl, or Br), a nitro group, a hydroxy group, $OCF_3$, or $COR^{13}$, where $R^{13}$ is $C_{1-6}$ alkyl or $CF_3$. Y is oxygen, sulfur, or $NR^{14}$, where $R^{14}$ is $C_{1-6}$ alkyl. $R^{16}$ is H or F.

In some embodiments, the RARγ selective agonist is 4-((1E,3E)-3-(3-(tert-butyl)-2-ethyl-benzofuran-5-yl)-3-(hydroxyimino)prop-1-en-1-yl)-3-fluorobenzoic acid (GA1E), having the structure (GA1E)

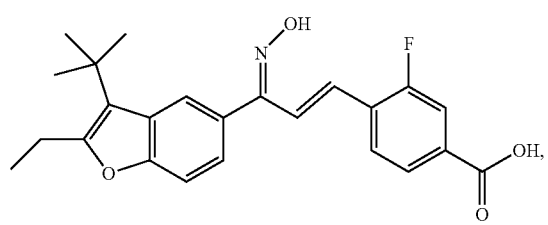

or a pharmaceutically acceptable salt thereof. In some embodiments, the RARγ selective agonist is 4-((1E,3Z)-3-(3-(tert-butyl)-2-ethyl-benzofuran-5-yl)-3-(hydroxyimino)prop-1-en-1-yl)-3-fluorobenzoic acid (GA1Z), having the structure (GA1Z)

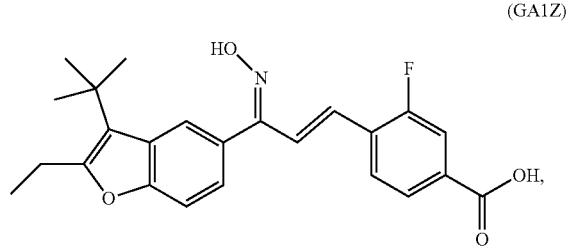 [SMILES: CCc1oc2ccc(C(/C=C/c3ccc(C(=O)O)cc3F)=N\O)cc2c1C(C)(C)C]

or a pharmaceutically acceptable salt thereof.

In some embodiments, the RARγ selective agonist is a compound of structure (GAG2)

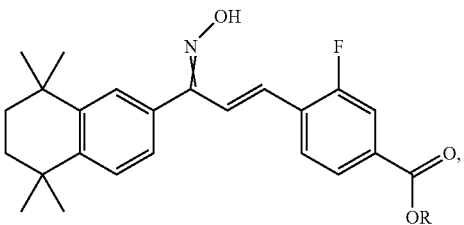

or a pharmaceutically acceptable salt thereof, wherein R is H or $C_{1-6}$ alkyl, and the crossed double bond to the =N—OH group indicates that stereochemistry is not specified. However, in some embodiments, the E configuration of the =N—OH group is preferred. In some embodiments, the RARγ agonist is 3-fluoro-4-((1E,3E)-3-(hydroxyimino)-3-(5,5,8,8-tetramethyl-5,6,7,8-tetrahydronaphthalen-2-yl)prop-1-en-1-yl)benzoic acid (GA2E), having the structure (GA2E)

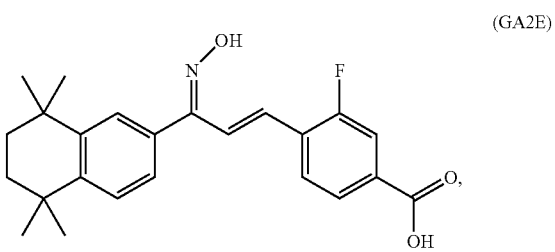 [SMILES: CC1(C)CCC(C)(C)c2cc(C(/C=C/c3ccc(C(=O)O)cc3F)=N/O)ccc21]

or a pharmaceutically acceptable salt thereof. In some embodiments, the RARγ selective agonist is 3-fluoro-4-((1E,3Z)-3-(hydroxyimino)-3-(5,5,8,8-tetramethyl-5,6,7,8-tetrahydronaphthalen-2-yl)prop-1-en-1-yl)benzoic acid (GA2Z), having the structure (GA2Z)

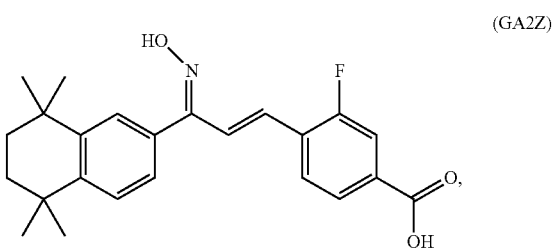 [SMILES: CC1(C)CCC(C)(C)c2cc(C(/C=C/c3ccc(C(=O)O)cc3F)=N\O)ccc21]

or a pharmaceutically acceptable salt thereof.

In some embodiments, the RARγ selective agonist is a compound of structure (GAG3)

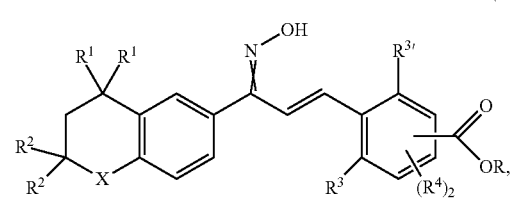

or a pharmaceutically acceptable salt thereof, wherein R is H or $C_{1-6}$ alkyl; each $R^1$ and $R^2$ are independently H or $C_{1-6}$ alkyl; $R^3$ and $R^{3'}$ are independently H, or halogen (for example, Cl, F, or Br); $(R^4)_2$ comprises $R^4$ and $R^{4'}$ which are independently H, halogen (for example, Cl, F, or Br), $C_{1-6}$ alkyl or $C_{1-6}$ alkoxy; X is O, S, $CH_2$, $C(R^5)_2$, or $NR^6$, wherein each $R^5$ and $R^6$ are independently H or $C_{1-6}$ alkyl; the crossed double bond to the =N—OH group indicates that stereochemistry is not specified; and the COOR group is in the meta or para position and the two $R^4$ groups occupy the remaining positions on the ring. In some embodiments, the para-position of the COOR group is preferred. In some embodiments, the E configuration of the =N—OH group is preferred. In some embodiments, both $R^1$ are $CH_3$. In some embodiments, both $R^2$ are H. In some embodiments, X is $C(R^5)_2$. In some embodiments, both $R^5$ are $CH_3$. In some embodiments, one $R^3$ is H and the other $R^3$ is F. In some embodiments, both $R^4$ are H. In some embodiments, all $R^3$ and $R^4$ are H. In some embodiments, R is H. In some embodiments, R is methyl or ethyl. In some embodiments, the COOR group is in the para position. In some embodiments, the COOR group is in the meta position. In some embodiments, the =N—OH group is in the E configuration. In some embodiments the =N—OH group is in the Z configuration. In particular embodiments, R is H and the carboxylic acid group is in the para position, both $R^1$ are $CH_3$, both $R^2$ are H, X is $C(CH_3)_2$, all $R^3$ and $R^4$ are H, and the =N—OH group is in the E configuration (GA3Ep). Some embodiments specifically include one or more specific substituents at one or more of the variable positions. Some embodiments specifically exclude one or more specific substituents at one or more of the variable positions.

In some embodiments, the RARγ selective agonist is CD437, CD2325, CD666, trifarotene, or BMS961.

One aspect is a method of treating cancer with RARγ agonist-expanded TIL. In some embodiments, the RARγ agonist is administered to a subject having a cancer to be treated.

In alternative embodiments, T lymphocytes are expanded in in vitro culture by exposing the culture to the RARγ agonist, and the RARγ agonist-expanded T lymphocytes are administered to a subject having a cancer to be treated, as adoptive T cell therapy. That is, the culture media is supplemented with the RARγ agonist. The concentration of RARγ agonist in the culture media can be in a range of 1 pM to 1 mM. In some embodiments, the concentration of RARγ agonist in the culture media is 0.5 nM. In some embodiments, the T lymphocytes are TIL isolated from a tumor explant from a subject. In some embodiments, the T lymphocytes are peripheral blood mononuclear cells (PBMC). In some embodiments, the T lymphocyte culture further comprises lethally irradiated tumor cells. In some embodiments, the tumor cells to be lethally irradiated are obtained from the subject to be treated. In some embodiments, the culture media is supplemented with interleukin 2 (IL-2). In some embodiments, the expanded T lymphocytes are administered to the subject by infusion, for example, by intravenous or intratumoral infusion.

In some embodiments, the subject is a mammal. In some embodiments, the subject is a human. In some embodiments, the RARγ agonist is GA1E. In some embodiments, the RARγ agonist is GA2E.

With respect to the above aspects, in some embodiments, the cancer is breast cancer. In some embodiments, the breast cancer is triple negative breast cancer. In some embodiments, the cancer is Her2$^+$ breast cancer. In some embodiments, the cancer is lung cancer, for example, non-small cell lung cancer. In some embodiments, the cancer is a solid tumor. In some embodiments, the cancer is a hematologic cancer. In some embodiments, the cancer is a carcinoma, a sarcoma, a melanoma, a glioblastoma, a leukemia, a lymphoma, a myeloma, or a plasma cell cancer.

In some embodiments, the effective amount of the RARγ agonist is about 0.01 to about 300 mg/m$^2$/day; however, doses below or above this exemplary range are within the scope of the present disclosure. The daily dose can be about 0.5 to about 100 mg/m$^2$/day, about 1 to about 90 mg/m$^2$/day, about 5 to about 80 mg/m$^2$/day; or at least about 0.02, 0.03, 0.05, 0.07, 0.1, 0.2, 0.3, 0.5, 0.7, 1, 2, 3, 5, 7, 10, 15, 20, 25, 30, 50, 70, or 100 mg/m$^2$/day; or not more than about 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m$^2$/day; or a range defined by any two of the foregoing values. In some embodiments, the effective amount for a human is about 0.006 to about 200 mg/day or about 1 to about 100 mg/day.

In some embodiments, the effective amount of the RARγ agonist is about 0.27 μg/kg/day to about 8 mg/kg/day; however, doses below or above this exemplary range are within the scope of the present disclosure. The daily dose can be about 0.013 to about 2.7 mg/kg/day, about 0.025 to about 2.5 mg/kg/day, about 0.130 to about 22 mg/kg/day; or at least about 0.0005, 0.0008, 0.001, 0.0013, 0.0020, 0.0025, 0.005, 0.0008, 0.0010, 0.0013, 0.0020, 0.0027, 0.005, 0.008, 0.010, 0.013, 0.020, 0.027, 0.05, 0.08, 0.1, 0.13, 0.2, 0.5, 0.8, 1.0, 1.3, 1.8, 2.0, or 2.7 mg/kg/day; or not more than about 0.0027, 0.005, 0.008, 0.010, 0.013, 0.020, 0.027, 0.05, 0.08, 0.1, 0.13, 0.2, 0.5, 0.8, 1.0, 1.3, 1.8, 2.0, or 2.7, 3.3, 4.0, 4.7, 5.4, 6.1, 6.8, 7.4, or 8.0 mg/kg/day, or a range defined by any two of the foregoing values.

With respect to any aspect comprising administering the RARγ selective agonist to a subject, in some embodiments, the administering occurs periodically throughout an interval of treatment. That is, the RARγ agonist is administered at regularly occurring time points within the interval of treatment. In some embodiments, periodically is twice daily, once daily, every other day, every third day, or twice weekly. In some embodiments, the administering occurs in repeated cycles throughout an interval of treatment. In some embodiments, a cycle comprises 1) administering the RARγ selective agonist periodically over a first span of time and 2) suspending administration of the RARγ selective agonist over a second span of time, after which a new cycle may be initiated. In some embodiments, the first span of time (during which the RARγ agonist is administered) is 10-15 days, or any integer number of days therein. In some embodiments, the second span of time (during which administration of the RARγ agonist is suspended) is two weeks to one month or any integer number of days therein. In various embodiments, the interval of treatment extends from a first administration of the RARγ agonist until, a complete response is achieved, stable disease is obtained, or disease progression again occurs after stable disease or regression.

With respect to any aspect comprising administering the RARγ selective agonist to a subject, some embodiments further comprise administering an inhibitor of regulatory T cells (Tregs). In some embodiments, the inhibitor of Tregs is a Treg-depleting antibody. In various embodiments, the Treg-depleting antibody is anti-CD25 antibody, an anti-glucocorticoid-induced tumor necrosis factor-related protein (GITR) antibody, an anti-FoxP3 antibody, an anti-CCR$_4$ antibody, or an anti-folate receptor 4 antibody. In some embodiments, the inhibitor of Tregs comprises an RARα antagonist.

With respect to any aspect comprising administering the RARγ selective agonist to a subject, some embodiments further comprise administering an RXR agonist having the structure

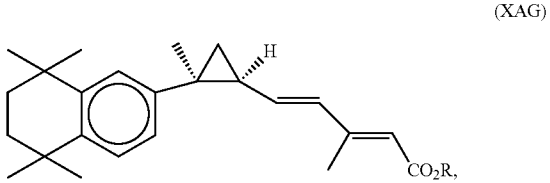

(XAG)

where R is H or $C_{1-6}$ alkyl, or a pharmaceutically acceptable salt thereof. In some embodiments, the RXR agonist is 3,7-dimethyl-6(S),7(S)-methano,7-[1,1,4,4-tetramethyl-1,2,3,4-tetrahydronaphth-7-yl]2(E), 4(E) heptadienoic acid (IRX4204).

With respect to any aspect comprising administering the RARγ-selective agonist to a subject, some embodiments further comprise administering a CAR-T cell. In some embodiments, the RARγ-selective agonist is a compound having a structure of GAG1 as defined above.

With respect to any aspect comprising administering the RARγ-selective agonist to a subject, some embodiments further comprise administering an anti-PD-1 or anti-PD-L1 antibody.

With respect to any aspect comprising generating or expanding TIL by contacting them with a RARγ selective agonist, some embodiments further comprise administering or supplementing culture media, as appropriate, with an anti-PD-1 or anti-PD-L1 antibody.

One aspect is a method of potentiating chimeric antigen receptor-T (CAR-T) cancer immunotherapy comprising administering an effective amount RARγ-selective agonist having the structure of GAG1, as defined above, to a cancer patient who is receiving, has received, or is scheduled to receive, CAR-T cells.

One aspect is a compound having a structure of GAG1 as defined above. One embodiment is 4-((1E,3E)-3-(3-(tert-butyl)-2-ethyl-benzofuran-5-yl)-3-(hydroxyimino)prop-1-en-1-yl)-3-fluorobenzoic acid (GA1E). Some embodiments are a pharmaceutically-acceptable salt of GA1E. Some embodiments are a $C_{1-6}$ ester of GA1E. Some embodiments are a pharmaceutical composition comprising GA1E, or a salt or ester thereof.

One aspect is a method of general synthesis of GAG1 according to the synthetic scheme in FIG. 1. A complete synthesis begins with Compound 1 and proceeds through intermediates, Compounds 2 through 5, to produce the species of GAG1, the isomers GA1E and GA1Z. Some embodiments are a method of synthesizing GAG1 species comprising producing intermediate Compound 4 by reacting Compound 3 with n-BuLi and N-methoxyl-N-methylacetamide. Some embodiments are a method of synthesizing GAG1 species comprising producing intermediate Compound 5 by reacting Compound 4 with methyl 3-fluoro-4-formylbenzoate. Some embodiments are a method of synthesizing GAG1 species by reacting Compound 5 with hydroxylamine hydrochloride in the presence of an organic or inorganic base. In some embodiments, the base is pyridine.

One aspect is intermediate Compound 4, having the structure

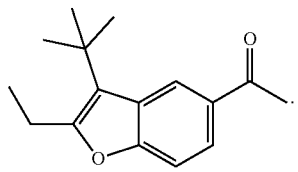 [SMILES: CCc1oc2ccc(C(C)=O)cc2c1C(C)(C)C]

A further aspect is a method of synthesizing Compound 4 by reacting Compound 3 with n-BuLi and N-methoxyl-N-methylacetamide.

One aspect is intermediate Compound 5, having the structure

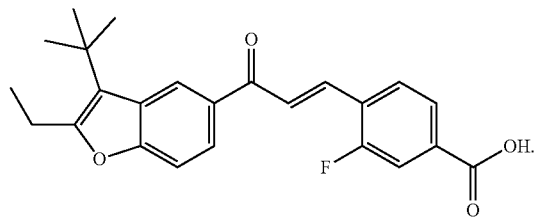 [SMILES: CCc1oc2ccc(C(=O)/C=C/c3ccc(C(=O)O)cc3F)cc2c1C(C)(C)C]

A further aspect is a method of synthesizing Compound 5 by reacting Compound 4 with methyl 3-fluoro-4-formylbenzoate in the presence of a base, such as NaOH.

BRIEF DESCRIPTION OF DRAWINGS

FIG. 4A shows tumor volume over the course of the experiment in each of the three arms of the study, and thus inhibition of tumor growth. FIG. 4B shows body weight over the course of the experiment in each of the three arms of the study.

FIG. 5A shows the number of live cells in the tumors and their percentage of the total cells (Live), the number of leukocytes based on CD45 staining and their percentage of the live cells (CD45), the total number of T cells based on CD3 staining and their percentage of the leukocytes (Tot T), and $CD4^+$ T cell based on CD4 staining and their percentage of total T cells (CD4T). FIG. 5B shows the number of memory T helper cells based on staining for CD4 and intracellular IFNγ and their percentage of total $CD4^+$ cells (TH IFNγ), the number of Th17 cells based on staining for CD4 and intracellular IL-17 and their percentage of total CD4+ cells (TH IL17), the number of T regulatory cells based on staining for CD4, CD25, and FOXP3 and their percentage of total CD4⁺ cells (Treg), CD8⁺ T cell based on CD8 staining and their percentage of total T cells (CD8T), and memory cytolytic T cells based on staining for CD8 and intracellular IFNγ and their percentage of CD8⁺ cells (TC IFNγ).

FIG. 7 depicts tumor growth, in mm³, in Balb/c mice implanted with EMT6 triple negative breast cancer cells in control mice (◆) and GA2E treated mice at 10 mg/kg (■) 25 mg/kg (▲), or 50 mg/kg (X), from the first day of treatment (Day 0) through the end of the study.

FIGS. 8A-C depict the production of IFNγ (in pg/ml) by recall antigen-stimulated PBMC treated with vehicle control or a RARγ selective agonist; FIG. 8A GA2E; FIG. 8B GA3Ep; FIG. 8C tazarotenic acid.

FIGS. 9A-C depict PBMC proliferation of recall antigen-stimulated CD8⁺ PBMC treated with vehicle control or a RARγ selective agonist; FIG. 9A GA2E; FIG. 9B GA3Ep; FIG. 9C tazarotenic acid.

FIG. 13A-C depicts flow cytometric biomarker analysis of CD8⁺ TIL from NSG-B2M mice implanted with a Her2⁺ breast cancer cell line (JIMT-1) and human PBMC in control (◆) and GA2E treated (■) mice on Day 26 (termination) of the study. The subsets were PD-1⁺ CD8⁺ T cells (FIG. 13A, TC PD1), CD18β⁺ CD8⁺ T cells (FIG. 13B, TC CD18), and CD54⁺ CD8⁺ T cells (FIG. 13C, TC CD54). Significance of the difference between treated and control:  indicates P<0.005; * indicates P<0.001; **** indicates P<0.0001.

FIG. 14A-E depicts flow cytometric T subset analysis of CD4⁺ TIL from NSG-B2M mice implanted with a Her2⁺ breast cancer cell line (JIMT-1) and human PBMC in control (◆) and GA2E treated (■) mice on Day 26 (termination) of the study. The subsets were total CD4⁺ T cells (FIG. 14A, TH), naive CD4⁺ T cells (FIG. 14B, CD4 Naïve), central memory CD4⁺ T cells (FIG. 14C, CD4 TCM), effector memory CD4⁺ T cells (FIG. 14D, CD4 TEM), and terminally differentiated effector CD4⁺ T cells (FIG. 14E, CD4 TEFF). Significance of the difference between treated and control: * indicates P<0.05; *** indicates P<0.001; no asterisks indicates P>0.05.

DESCRIPTION

Disclosed herein are methods of expanding tumor-infiltrating lymphocytes (TIL) and associated methods of treating cancer by administering an effective amount of a RARγ selective agonist to a subject in need thereof.

As used herein "RARγ selective agonist" refers to RARγ agonists that have no or negligible agonistic activity for RARα at some clinically relevant concentrations. In some embodiments, the RARγ selective agonist is selective in that it has no or negligible agonistic activity for both RARα and RARβ at some clinically relevant concentrations. "Clinically relevant concentrations" refers to the concentration in the blood (typically determined by assaying plasma or serum) of a subject receiving efficacious doses of the RARγ selective agonist, or the concentration used in in vitro culture for generating, differentiating, or expanding TIL, as relevant to the method in which the RARγ selective agonist is being used. In some embodiments, the $EC_{50}$ for activation of RARγ is at least 100-fold less, or at least 50-fold less, than for the activation of RARα, or RARα and RARβ.

One aspect is a method of treating cancer comprising administering, to a patient in need thereof, an effective amount RARγ-selective agonist having a structure

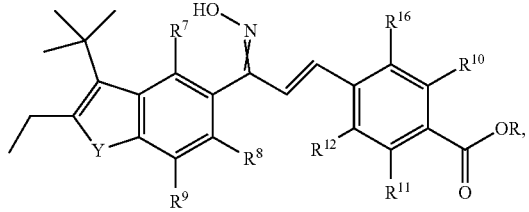

(GAG1)

or a pharmaceutically acceptable salt thereof, wherein R is H or $C_{1-6}$ alkyl, and the crossed double bond to the =N—OH group indicates that stereochemistry is not specified. However, in some embodiments, the E configuration of the =N—OH group is preferred. $R^7$ to $R^{12}$ are independently: $C_{1-6}$ alkyl, a hydrogen atom, an alkoxy group, a halogen atom (for example F, Cl, or Br), a nitro group, a hydroxy group, $OCF_3$, or $COR^{13}$, where $R^{13}$ is $C_{1-6}$ alkyl or $CF_3$. Y is oxygen, sulfur, or $NR^{14}$, where $R^{14}$ is $C_{1-6}$ alkyl. $R^{16}$ is H or F. In some embodiments, R is methyl or ethyl. In some embodiments, R is H. In some embodiments, $R^{16}$ is F.

Figure 1:
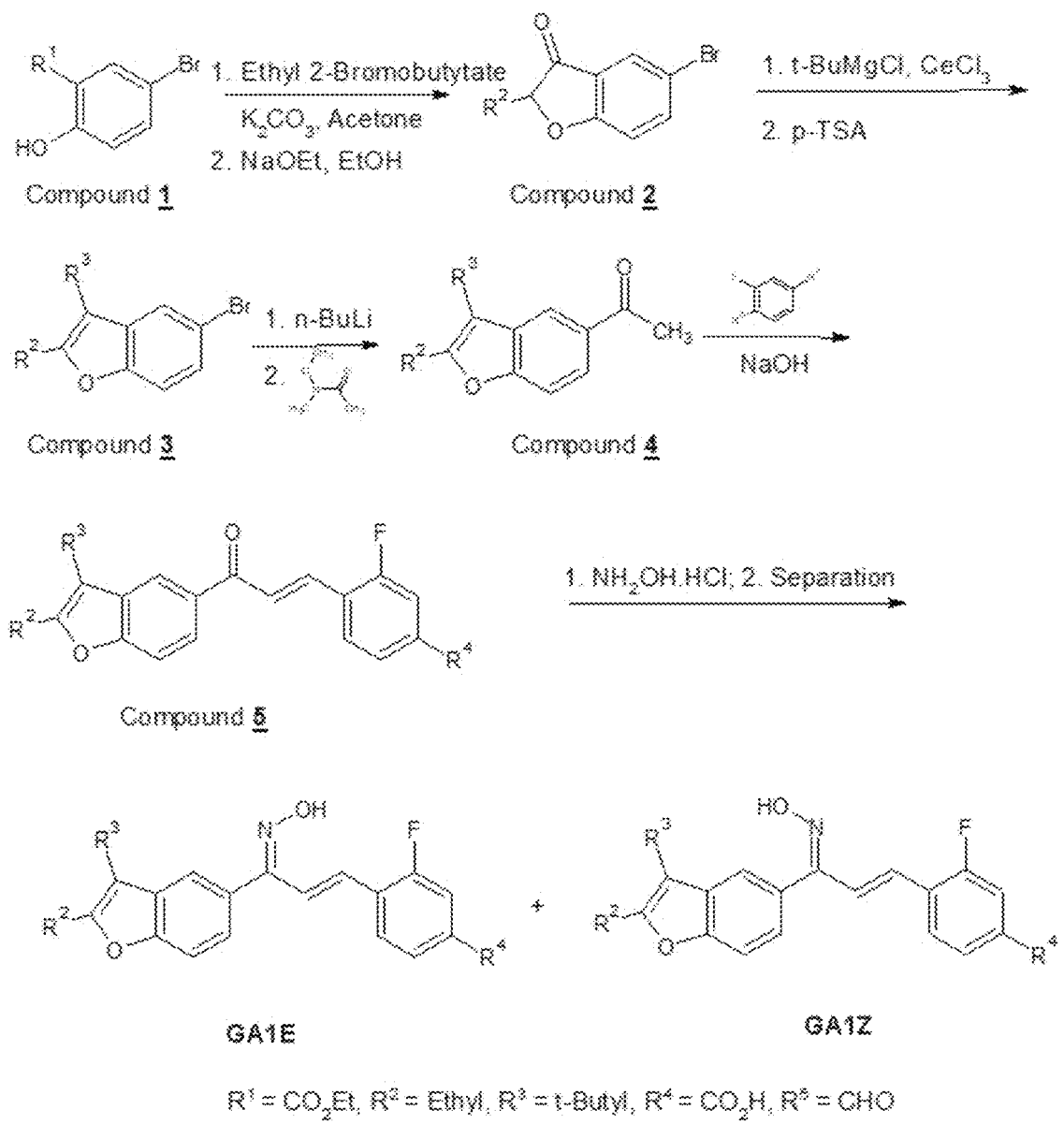
FIG. 1 presents a scheme for the synthesis of the species of GAG1, GA1E and GA1Z.
Figure 2:
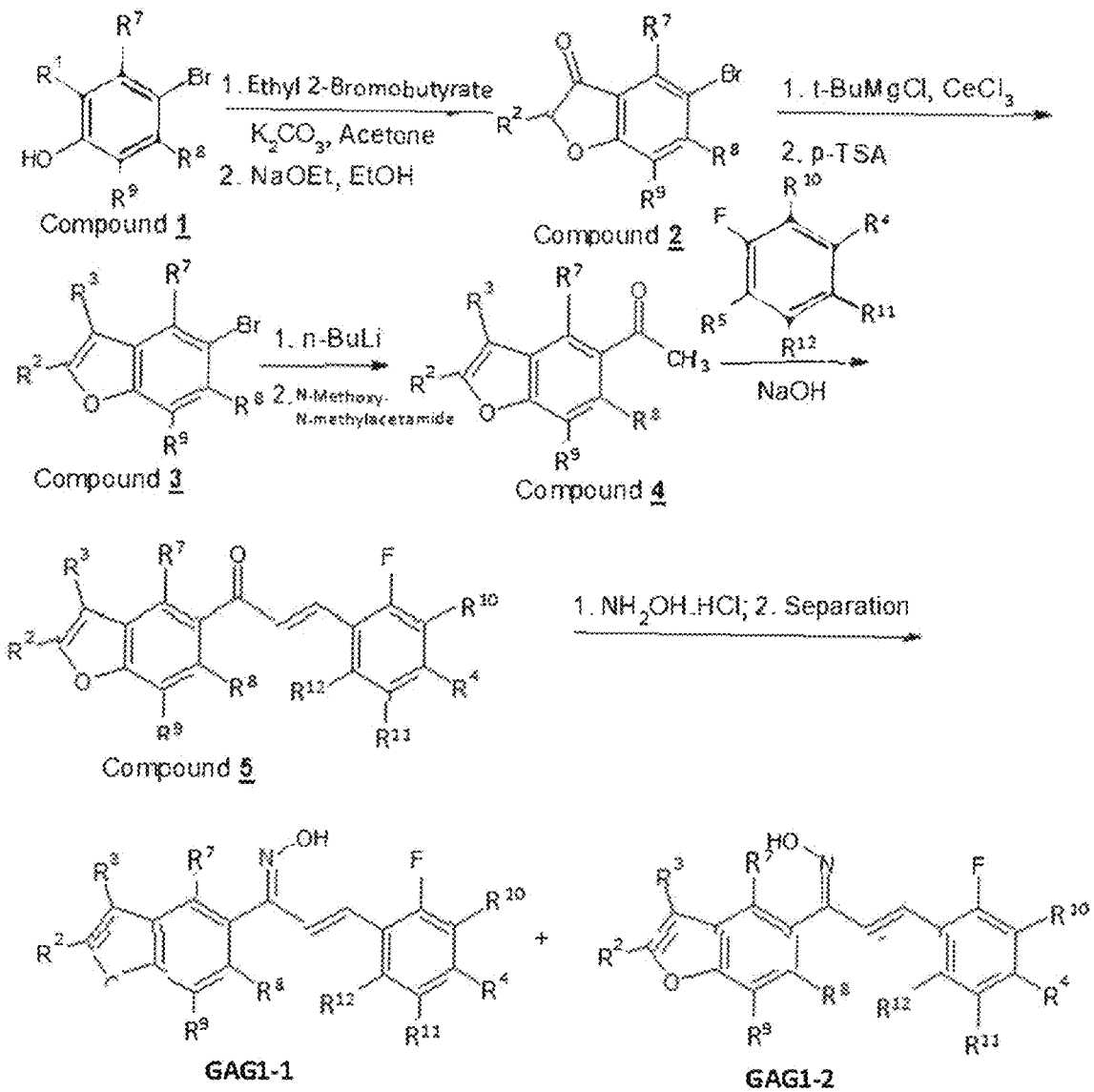
FIG. 2 presents a scheme for the synthesis of the species of GAG1, GAG1-1 and GAG1-2.

Synthetic schemes for species of GAG1 are presented in FIGS. 1 and 2.

In some embodiments, in the RARγ-selective agonist having a structure of GAG1, Y is O:

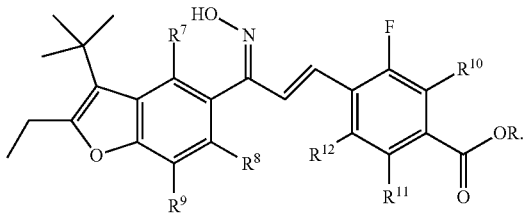

(GAG1-1)

In some embodiments, in the RARγ-selective agonist having a structure of GAG1, the =N—OH group is in the E configuration:

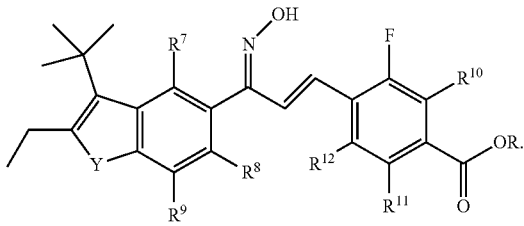

(GAG1-2)

In some embodiments, the RARγ-selective agonist having a structure of GAG1 has the structure

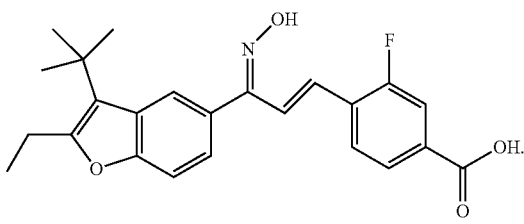

(GA1E)

As used herein, alkyl means a moiety composed of carbon and hydrogen containing no double or triple bonds. Alkyl may be linear alkyl, branched alkyl, cycloalkyl, or a combination thereof. $C_{1-6}$ alkyl, means an alkyl group having 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having anywhere from 1-6 carbon atoms. These considerations apply equally to the alkyl portion or an alkoxy group.

With respect to the herein disclosed structures comprising aromatic rings substituted with R groups, when the R group is an alkoxy group, one valence of the oxygen atom is attached to the aromatic ring and the other valence is attached to the alkyl portion of the alkoxy group.

One aspect disclosed herein is a method of generating, differentiating, or expanding TIL by contacting them with a RARγ selective agonist. RARγ agonists stimulate T cell effector function, but not Treg cells, and thus can promote an anti-cancer immune response. In particular, the RARγ selective agonists described herein can promote expansion of $CD8^+$ TIL. IL-2 has been used previously for expanding TIL. In vitro culture can result in changes to the T cell receptor repertoire and the in vitro-expanded TIL are typically infused with further IL-2 as a growth factor. However, IL-2 is also associated with a variety of toxicities, some associated with capillary leak syndrome presented by edema, hypotension and reduced urine output within hours of infusion, but also fevers, rigors, myalgia and nausea. An alternative agent to expand TIL without producing such substantial toxicity is a long-felt, unmet need.

As used herein, the term "TIL" refers primarily to the lymphocytes that can be found within a tumor. Such TIL can be isolated from explanted tumor tissue and expanded in vitro. Yet TIL infiltrate the tumor from outside the tumor thus can also be found outside the tumor. Therefore, it is also possible to culture PBMC in vitro in the presence of tumor antigen (for example, lethally irradiated tumor cells) to generate or expand T cells capable of infiltrating into tumors. Methods of generating, differentiating, or expanding TIL encompass such use of PBMC.

In some embodiments, contacting TIL with a RARγ selective agonist comprises culturing the TIL in vitro in a media supplemented with the RARγ selective agonist. Procedures for culturing TIL are known to those of skill in the art. To summarize a basic procedure, resected tumor tissue is minced into approximate 1-3 mm$^3$ fragments and placed in culture (for example in 24- or 48-well plates with 2 or 1 mL of culture media, respectively) and the TIL allowed to extravasate from the tissue. Alternatively, the tumor tissue may be subjected to enzymatic digestion and/or mechanical disaggregation to obtain a single cell suspension. For expansion, the TIL can be cultured in vitro for 3-6 weeks in an appropriate medium, replacing half the media every 2-3 days and splitting at 80% confluence. Tumor cells disappear from the culture over the first 1-3 weeks. To more rapidly expand the TIL, anti-CD3 antibody and 100 to 200-fold excess of irradiated feeder cells (autologous or allogeneic) can be added to the culture. The TIL can be transferred to a bioreactor to support high cell density and achieve a population of from $10^9$ to $2\times10^{11}$ cells. The RARγ selective agonist is used continually in the culture.

In some embodiments, in which TIL are being generated or expanded from PBMC, the PBMC are obtained from the subject to be treated (autologous). In other embodiments, the PBMC are obtained from an HLA-matched donor. In some embodiments, tumor cells are obtained from the subject to be treated, while in other embodiments they are obtained from a different individual. In some embodiments, the PBMC and the tumor cells are obtained from the same individual. In some embodiments, that individual is the subject to be treated. In some embodiments, the PBMC and the tumor cells are obtained from different individuals, for example, the PBMC can be autologous but cultured with tumor cells from an HLA-matched or allogeneic donor. In some embodiments, the PBMC (or TIL) are cultured with lethally-irradiated tumor cells, but in alternative embodiments the culture contains a tumor cell lysate, or purified or synthetic tumor antigens.

In some embodiments, contacting comprises administering the RARγ selective agonist to a subject having a tumor.

One aspect disclosed herein is a method of treating cancer comprising providing RARγ selective agonist-expanded TIL to a patient in need thereof. In one embodiment, the RARγ selective agonist is administered to a subject having a cancer to be treated. In an alternative embodiment, TIL are expanded in culture by exposing the culture to the RARγ selective agonist, and the RARγ selective agonist-expanded TIL are administered to a subject having a cancer to be treated as adoptive T cell therapy. In some embodiments, the subject is a mammal. In some embodiments the subject is a human. In some embodiments, the RARγ selective agonist is GAG1. In some embodiments, the RARγ selective agonist is GAG2. In some embodiments, the RARγ selective agonist is GAG3p. In some instances, the =N—OH group of GAG1, GAG2, or GAG3p is in the E configuration. In still further embodiments, the RARγ selective agonist is any individual species or group of species encompassed by structures GAG1, GAG2, or GAG3. Some embodiments specifically, exclude any individual species or group of species encompassed by structures GAG1, GAG2, or GAG3.

With respect to any relevant aspect, in some embodiments, the cancer is a solid tumor, a carcinoma, a sarcoma, or a hematologic cancer. With respect to any relevant aspect, in some embodiments, the cancer is a melanoma, a glioblastoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer ovarian cancer, a leukemia, a lymphoma, a myeloma, or a plasma cell cancer. With respect to any relevant aspect, in some embodiments, the cancer is breast cancer. In some embodiments, the breast cancer is triple negative breast cancer. In some embodiments, the cancer is Her2$^+$ breast cancer. In some embodiments, the cancer is lung cancer, for example, non-small cell lung cancer. In some embodiments, the subject in need thereof is human.

The growth of many breast cancers is stimulated by estrogen, progesterone and (particularly when the cancer expresses excess human epidermal growth factor receptor 2 (Her2)) epidermal growth factor. Agents that antagonize these effects have proven to be effective treatments for breast cancer. However, about 10-20% of breast cancers do not express estrogen receptor, progesterone receptor, or excess Her2. These cancers are therefore termed "triple negative breast cancer". Triple negative breast cancer is typically more aggressive and has a poorer prognosis than other types of breast cancer, in part due to there being fewer treatment options. Triple negative breast cancer is also more likely to metastasize and more likely to recur after treatment. Breast cancers are graded on their resemblance to normal healthy breast cells on a 3 point scale, with higher grades indicating less resemblance to normal cells. Triple negative breast cancers are often grade 3. Triple negative breast cancers are usually "basal-like" meaning they resemble the basal cells lining the breast ducts. Basal-like cancers tend to be more aggressive and higher grade. The onset of triple negative breast cancer tends to occur at an earlier age, for example, under 50 as compared to other types of breast cancer which are more commonly diagnosed in persons over 60 years of age. About 70% of cancers having a BRCA mutation are triple negative. Altogether, these factors make triple negative breast cancer a particularly difficult disease to treat.

Current treatments for triple negative breast cancer include neoadjuvant chemotherapy (chemotherapy prior to surgical removal of the tumor); inhibitors of poly ADP-ribose polymerase (PARP), such as olaparib; and immunotherapy for example by PD-1 blockade, such as by atezolizumab, in combination with albumin-bound paclitaxel.

In some embodiments, in which the RARγ selective agonist is administered to the subject, the effective amount is about 0.01 to about 300 mg/m$^2$/day; however, doses below or above this exemplary range are within the scope of the present disclosure. The daily dose can be about 0.5 to about 100 mg/m$^2$/day, about 1 to about 90 mg/m$^2$/day, about 5 to about 80 mg/m$^2$/day; or at least about 0.02, 0.03, 0.05, 0.07, 0.1, 0.2, 0.3, 0.5, 0.7, 1, 2, 3, 5, 7, 10, 15, 20, 25, 30, 50, 70, or 100 mg/m²/day; or not more than about 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m²/day; or a range defined by any two of the foregoing values. These dosages may be converted into approximately equivalent human dosages in mg/kg/day by dividing by 37.

In some embodiments, the effective amount of the RARγ agonist is about 0.27 µg/kg/day to about 8 mg/kg/day; however, doses below or above this exemplary range are within the scope of the present disclosure. The daily dose can be about 0.013 to about 2.7 mg/kg/day, about 0.025 to about 2.5 mg/kg/day, about 0.130 to about 22 mg/kg/day; or at least about 0.0005, 0.0008, 0.001, 0.0013, 0.0020, 0.0025, 0.005, 0.0008, 0.0010, 0.0013, 0.0020, 0.0027, 0.005, 0.008, 0.010, 0.013, 0.020, 0.027, 0.05, 0.08, 0.1, 0.13, 0.2, 0.5, 0.8, 1.0, 1.3, 1.8, 2.0, or 2.7 mg/kg/day; or not more than about 0.0027, 0.005, 0.008, 0.010, 0.013, 0.020, 0.027, 0.05, 0.08, 0.1, 0.13, 0.2, 0.5, 0.8, 1.0, 1.3, 1.8, 2.0, or 2.7, 3.3, 4.0, 4.7, 5.4, 6.1, 6.8, 7.4, or 8.0 mg/kg/day, or a range defined by any two of the foregoing values. These dosages may be converted into approximately equivalent human dosages in mg/m²/day by multiplying by 37.

In some embodiments, the effective amount for a human is about 0.006 to about 200 mg/day or about 1 to about 100 mg/day. In some embodiments, the daily dose is given in a single administration. In other embodiments, the daily dose is split into multiple administrations, for example two administrations, 9-15, 10-14, 11-13, or 12 hours apart.

It is not necessary that the RARγ selective agonist be present at a therapeutic level in the subject throughout treatment. This is because the primary therapeutic effect of the RARγ selective agonist is indirect, promoting an immune response, the expansion of TIL, which persists in the absence of the RARγ selective agonist. Because it takes time for the immune response to develop, the beneficial effect may not be observed until administration of the RARγ selective agonist is paused. Indeed, in some embodiments, it may be beneficial to have a drug holiday during which administration of the RARγ selective agonist suspended. To the extent that administration of the RARγ selective agonist is associated with a toxicity or other undesirable side-effect, a suspension of administration allows time for the subject to recover from the ill effects, rather than for them to continue to worsen. As used herein "suspended" refers to a cessation of drug administration with the intent and expectation that it will resume at a later time and is distinct from discontinuation in which there no plan to resume administration of the drug. Resumption of administration of can be beneficial as immune responses tend to wane over time. Thus, with to any aspect comprising administering the RARγ selective agonist to a subject, in some embodiments, the administering occurs periodically throughout an interval of treatment. That is, the RARγ agonist is administered at regularly occurring time points within the interval of treatment. In some embodiments, periodically is twice daily, once daily, every other day, every third day, or twice weekly. In some embodiments, the administering occurs in repeated cycles throughout an interval of treatment. In some embodiments, a cycle comprises 1) administering the RARγ selective agonist periodically over a first span of time and 2) suspending administration of the RARγ selective agonist over a second span of time, after which a new cycle may be initiated. In some embodiments, the first span of time (during which the RARγ agonist is administered) is 10-15 days, or any integer number of days therein. In some embodiments, the second span of time (during which administration of the RARγ agonist is suspended) is two weeks to one month or any integer number of days therein. In various embodiments, the interval of treatment extends from a first administration of the RARγ agonist until a complete response is achieved, stable disease is obtained, or disease progression occurs.

The RARγ selective agonist may be administered to a subject by any suitable route of administration. In some embodiments, the RARγ a selective agonist is administered orally. In some embodiments, the RARγ selective agonist is administered by injection or infusion, for example, intravenously, subcutaneously, or intratumorally. In some embodiments, the RARγ selective agonist is administered intranasally. In some embodiments, the RARγ selective agonist is administered by nasal or oral (pulmonary) inhalation.

Ex vivo expanded TIL are generally administered by infusion, for example intravenous or intratumoral infusion. However, in some embodiments, ex vivo expanded TIL are administered in a single bolus or split into multiple boluses, intravenously, or intratumorally. In some embodiments, the RARγ selective agonist is included in the bolus or infusion with the TIL. In various embodiments, infusion may extend for half an hour, for an hour, for several hours, for a day, or for several days.

In some embodiments, about $10^9$ to >$10^{11}$ TIL are administered, for example, about $1 \times 10^{10}$ to $2 \times 10^{11}$. The RARγ selective agonist is used continually in the culture and may be included with the infused, expanded TIL. The RARγ agonist may also be administered to the patient subsequent to TIL infusion for a set period of time or until tumor is eliminated or no further benefit from the TIL is observed.

In some embodiments, the RARγ selective agonist is used as monotherapy. In other embodiments, it is used in combination with one of the current therapies, either before, during, or after, the other treatment.

RARγ selective agonists promote expansion of TIL that are CD8⁺ effector cells. Consistent with what is known about CD8⁺ effector cells generally, these cell express PD-1, which can act as a negative regulator of CD8⁺ effector cell activity. Thus, in some embodiments, treatment with a RARγ selective agonist is combined with PD-1 blockade. Treatment with RARγ selective agonists can also increase the presence of PD-1⁺ T cells among CD8⁺ TIL. For this reason as well, in some embodiments, treatment with a RARγ selective agonist is combined with PD-1 blockade. Several products for PD-1 blockade, also called immune checkpoint inhibition, are undergoing clinical evaluation. These include the anti-PD-1 antibodies pembrolizumab, nivolumab, cemiplimab, dostarlimab, tislelizumab, spartalizumab, camrelizumab, sintilimab, toripalimab, JTX-4014, INCMGA00012, AMP-514, and budigalimab, and the anti-PD-L1 antibodies atezolizumab, avelumab, durvalumab, envafolimab, CK-301, CS-1001, KN035SHR-1316, CBT-502, BGB-A333, and BMS-936559. Several non-antibody inhibitors of PD-L1 are also in development, including AUNP12 (a 29 mer peptide), CA-170 (a small organic molecule), and BMS-986189 (a macrocyclic peptide). AMP-224 is a fusion protein of PD-L2 (also known as B7-DC) with an antibody Fc region, which is being developed as an anti-PD-1 checkpoint inhibitor. Such antibodies constitute means for PD-1 blockade.

A growing mode of cancer treatment is chimeric antigen receptor T cell (CAR-T) therapy. CAR-T cells are effectively artificial TIL. Accordingly, in some embodiments, treatment with a RARγ selective agonist, as described herein, is combined with CAR-T therapy. RARγ-selective agonists can potentiate chimeric antigen receptor-modified immune cells (CAR-MIC) therapy, as described in US2019001563A1 and US20180338940A1 (each of which is incorporated by reference for all that they teach about potentiation of CAR-MIC with RARγ agonists). Thus, some embodiment are methods of potentiating CAR-MIC cancer immunotherapy comprising administering a RARγ-selective agonist having the structure of GAG1 to a cancer patient who is receiving, has received, or is scheduled to receive, CAR-MIC. In some instances, the CAR-MIC is a CAR-T cell.

With respect to any aspect comprising administering the RARγ selective agonist to a subject, some embodiments further comprise administering an inhibitor of regulatory T cells (Tregs). In some embodiments, the inhibitor of Tregs is a Treg-depleting antibody. In various embodiments, the Treg-depleting antibody is anti-CD25 antibody, an anti-GITR antibody, an anti-FoxP3 antibody, an anti-CCR$_4$ antibody, or an anti-folate receptor 4 antibody. In some embodiments, the inhibitor of Tregs comprises a RARα antagonist.

With respect to any aspect comprising administering the RARγ selective agonist to a subject, some embodiments further comprise administering an RXR agonist having the structure

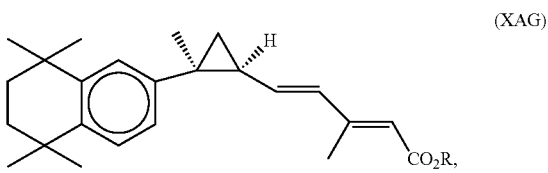

(XAG)

where R is H or C$_{1-6}$ alkyl, or a pharmaceutically acceptable salt thereof. In some embodiments, R is methyl or ethyl. In some embodiments, R is H; that is the RXR agonist is 3,7-dimethyl-6(S),7(S)-methano,7-[1,1,4,4-tetramethyl-1,2,3,4-tetrahydron-aphth-7-yl]2(E), 4(E) heptadienoic acid, also known as IRX4204. Compounds with the structure of XAG have anticancer activity as described in US 2008/0300312A1 and US 2020/0390736A1 (which are incorporated by reference for all that they teach about the treatment of cancer with these RXR agonists). Treatment with RARγ selective agonists can have undesirable side effects, such as weight loss that can become excessive, especially at higher dosages, as seen in some of the Examples below. Compounds with the structure of XAG also have an anticachectic effect, as described in US 20070185055A1 (which is incorporated by reference for all that it teaches about the treatment of cachexia with RXR agonists), which could counteract or mitigate the side effects of the RARγ agonist contributing to potentially excessive weight loss. Accordingly, for either or both of these reasons, in some embodiments treatment with a RARγ selective agonist, as described herein, is combined with treatment with an appropriate RXR agonist, such as IRX4204.

The average surface area of a human body is generally accepted to be 1.9 m$^2$ for an adult male, 1.6 m$^2$ for an adult female, and 1.33 m$^2$ for a 12-13 year old child. These values can be used to calculate dose ranges for doses of the RARγ selective agonist. The total daily dosage of RARγ selective agonist active agents can be administered as a single dose or as two doses administered with a 24 hour period spaced 8 to 16, or 10 to 14, hours apart. For repeated administrations over several days or longer, the treatment can be repeated until a desired suppression of disease or disease symptoms occurs. However, other dosage regimens may be useful and are within the scope of the disclosure. The desired dosage can be delivered by a single bolus administration of the composition, by multiple bolus administrations of the composition, or by continuous infusion administration of the composition.

The RARγ selective agonist can be administered to a mammal using standard administration techniques, including parenteral, oral, intravenous, intraperitoneal, subcutaneous, pulmonary, transdermal, intramuscular, intranasal, buccal, sublingual, or suppository administration. The term "parenteral," as used herein, includes intravenous, intramuscular, subcutaneous, rectal, vaginal, and intraperitoneal administration. The RARγ selective agonist preferably is suitable for oral administration, for example as a pill, tablet or capsule.

Administration may be continuous or intermittent. The dosage may also be determined by the timing and frequency of administration. Thus, the RARγ selective agonist disclosed herein can be given on a daily, weekly, biweekly, or monthly basis for a period of time, followed by an optional drug holiday (drug free period) and that this drug administration/drug holiday cycle can be repeated as necessary. For example, the RARγ selective agonist could be administered daily for a week, and then not administered for the rest of a month, and then administered for another week, etc. In certain embodiments, the total daily dosage of RARγ agonist can be administered as a single dose or as two doses administered with a 24-hour period spaced 8 to 16, or 10 to 14, hours apart.

The effectiveness of cancer therapy is typically measured in terms of "response." The techniques to monitor responses can be similar to the tests used to diagnose cancer such as, but not limited to:

A lump or tumor involving some lymph nodes can be felt and measured externally by physical examination.
Some internal cancer tumors will show up on an x-ray or CT scan and can be measured with a ruler.
Blood tests, including those that measure organ function can be performed.
A tumor marker test can be done for certain cancers.
Regardless of the test used, whether blood test, cell count, or tumor marker test, it is repeated at specific intervals so that the results can be compared to earlier tests of the same type.
Response to cancer treatment is defined several ways:
Complete response—all of the cancer or tumor disappears; there is no evidence of disease. Expression level of tumor marker (if applicable) may fall within the normal range.
Partial response—the cancer has shrunk by a percentage but disease remains. Levels of a tumor marker (if applicable) may have fallen (or increased, based on the tumor marker, as an indication of decreased tumor burden) but evidence of disease remains.
Stable disease—the cancer has neither grown nor shrunk; the amount of disease has not changed. A tumor marker (if applicable) has not changed significantly.
Disease progression—the cancer has grown; there is more disease now than before treatment. A tumor marker test (if applicable) shows that a tumor marker has risen.
Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis.

The terms "treating" or "treatment" broadly include any kind of treatment activity, including the mitigation, or prevention of disease, or an aspect thereof, in man or other animals, or any activity that otherwise affects the structure or any function of the body of man or other animals. Treatment activity includes the administration of the medicaments, dosage forms, and pharmaceutical compositions described herein to a patient, especially according to the various methods of treatment and methods of generating, differentiating or expanding TIL disclosed herein, whether by a healthcare professional, the patient his/herself, or any other person. Treatment activities include the orders, instructions, and advice of healthcare professionals such as physicians, physician's assistants, nurse practitioners, and the like, that are then acted upon by any other person including other healthcare professionals or the patient him/herself. This includes, for example, direction to the patient to undergo, or to a clinical laboratory to perform, a diagnostic procedure, such as for cancer diagnosis and staging, so that ultimately the patient may receive the benefit appropriate treatment. In some embodiments, the orders, instructions, and advice aspect of treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like. All such orders, instructions, and advice are to be seen as conditioning receipt of the benefit of the treatment on compliance with the instruction. In some instances, a financial benefit is also received by the patient for compliance with such orders, instructions, or advice. In some instances, a financial benefit is also received by the healthcare professional for compliance with such orders, instructions, or advice.

RARγ Selective Agonists

One aspect comprises an RARγ selective agonist, wherein the RARγ selective agonist is a compound having a structure of

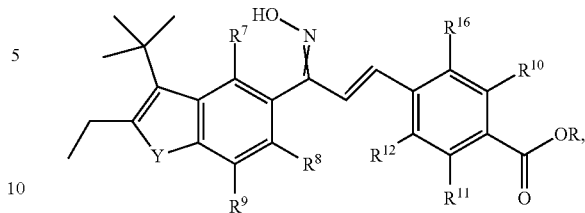

(GAG1)

or a pharmaceutically acceptable salt thereof, wherein R is H or $C_{1-6}$ alkyl. However, in some embodiments, the E configuration of the =N—OH group is preferred. $R^7$ to $R^{12}$ are independently: $C_{1-6}$ alkyl, a hydrogen atom, an alkoxy group, a halogen atom (for example F, Cl, or Br), a nitro group, a hydroxy group, $OCF_3$, or $COR^{13}$, where $R^{13}$ is $C_{1-6}$ alkyl or $CF_3$. Y is oxygen, sulfur, or $NR^{14}$, where $R^{14}$ is $C_{1-6}$ alkyl. In some embodiments, R is methyl or ethyl. In some embodiments, R is H. Some embodiments are a pharmaceutical composition or formulation comprising a compound having the structure of GAG1 or a pharmaceutically acceptable salt thereof. With respect to any method aspect, in some embodiments, the RARγ selective agonist is a compound having the structure of GAG1 or a pharmaceutically acceptable salt thereof.

In some embodiments, in the RARγ-selective agonist having a structure of GAG1, Y is O:

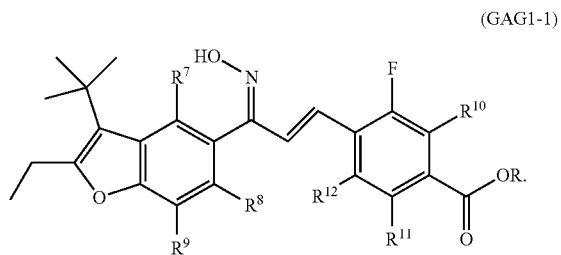

(GAG1-1)

In some embodiments, in the RARγ-selective agonist having a structure of GAG1, the =N—OH group is in the E configuration:

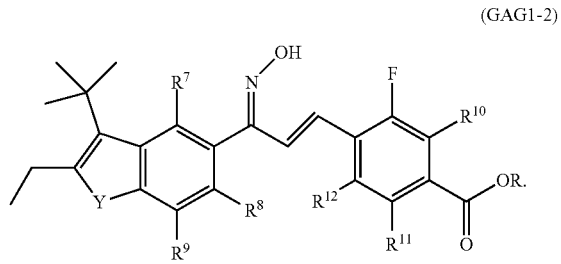

(GAG1-2)

With respect to any aspect, in some embodiments, the RARγ selective agonist is 4-((1E,3E)-3-(3-(tert-butyl)-2-ethyl-benzofuran-5-yl)-3-(hydroxyimino)prop-1-en-1-yl)-3-fluorobenzoic acid (GA1E), having the structure In some embodiments, the RARγ selective agonist is 3-fluoro-4-((1E,3E)-3-(hydroxyimino)-3-(5,5,8,8-tetramethyl-5,6,7,8-tetrahydronaphthalen-2-yl)prop-1-en-1-yl)benzoic acid (GA2E), having the structure

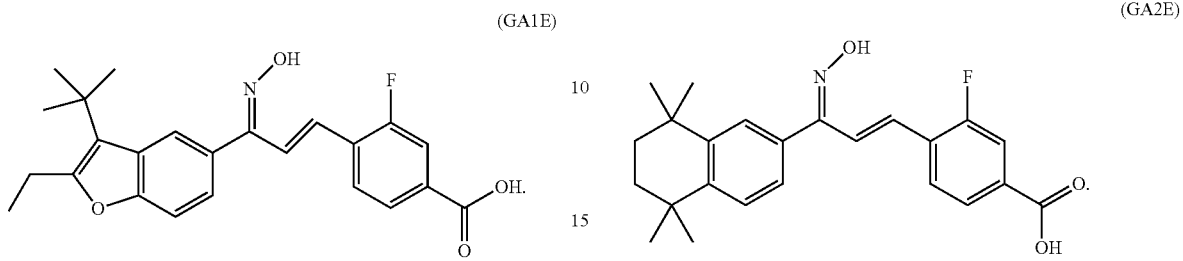

(GA1E)

(GA2E)

In some embodiments, the RARγ selective agonist is 4-((1E,3Z)-3-(3-(tert-butyl)-2-ethyl=benzofuran-5-yl)-3-(hydroxyimino)prop-1-en-1-yl)-3-fluorobenzoic acid (GA1Z), having the structure In some embodiments, the RARγ selective agonist is 3-fluoro-4-((1E,3Z)-3-(hydroxyimino)-3-(5,5,8,8-tetramethyl-5,6,7,8-tetrahydronaphthalen-2-yl)prop-1-en-1-yl)benzoic acid (GA2Z), having the structure

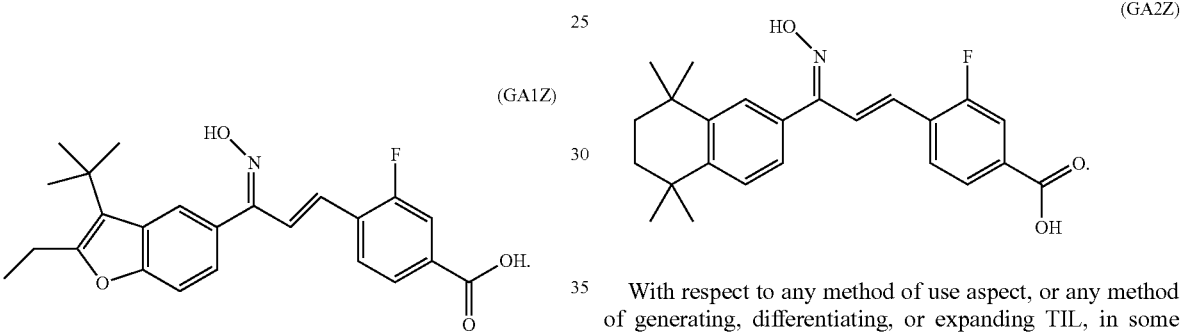

(GA1Z)

(GA2Z)

With respect to any method of use aspect, or any method of generating, differentiating, or expanding TIL, in some embodiments, the RARγ selective agonist is a compound of structure With respect to any method of use aspect, or any method of generating, differentiating, or expanding TIL, in some embodiments, the RARγ selective agonist is a compound of structure

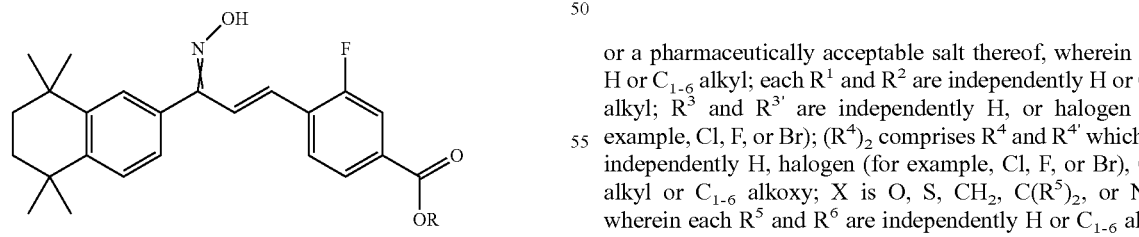

(GAG2)

(GAG3)

or a pharmaceutically acceptable salt thereof, wherein R is H or $C_{1-6}$ alkyl, and the crossed double bond to the =N—OH group indicates that stereochemistry is not specified. However, in some embodiments, the E configuration of the =N—OH group is preferred. In some embodiments, R is methyl or ethyl. In some embodiments, R is H. In some embodiments, R is methyl or ethyl.

or a pharmaceutically acceptable salt thereof, wherein R is H or $C_{1-6}$ alkyl; each $R^1$ and $R^2$ are independently H or $C_{1-6}$ alkyl; $R^3$ and $R^{3'}$ are independently H, or halogen (for example, Cl, F, or Br); $(R^4)_2$ comprises $R^4$ and $R^{4'}$ which are independently H, halogen (for example, Cl, F, or Br), $C_{1-6}$ alkyl or $C_{1-6}$ alkoxy; X is O, S, $CH_2$, $C(R^5)_2$, or $NR^6$, wherein each $R^5$ and $R^6$ are independently H or $C_{1-6}$ alkyl; the crossed double bond to the =N—OH group indicates that stereochemistry is not specified; and the COOR group is in the meta or para position and the two $R^4$ groups occupy the remaining positions on the ring. In some embodiments, the para-position of the COOR group is preferred. In some embodiments, the E configuration of the =N—OH group is preferred. In some embodiments, both $R^1$ are $CH_3$. In some embodiments, both $R^2$ are H. In some embodiments, X is $C(R^5)_2$. In some embodiments, both $R^5$ are $CH_3$. In some embodiments, one R³ is H and the other R³ is F. In some embodiments, both R⁴ are H. In some embodiments, all R³ and R⁴ are H. In some embodiments, R is H. In some embodiments, R is methyl or ethyl. In some embodiments, the para-position of the COOR group is preferred. In some embodiments, the E configuration of the =N—OH group is preferred. In some embodiments, both R¹ are CH₃. In some embodiments, both R¹ are H. In some embodiments, both R² are H. In some embodiments, X is C(R⁵)₂. In some embodiments, X is CH₂. In some embodiments, both R⁵ are CH₃. In some embodiments, both R³ are H, while in other embodiments, one R³ is H and one R³ is F. In some embodiments, both R⁴ are H. In some embodiments, all R³ and R⁴ are H. In some embodiments, the COOR group is in the para position. In some embodiments, the COOR group is in the meta position. In some embodiments, the =N—OH group is in the E configuration. In some embodiments the =N—OH group is in the Z configuration. In particular embodiments, R is H and the carboxylic acid group is in the para position, both R¹ are CH₃, both R² are H, X is C(CH₃)₂, all R³ and R⁴ are H, and the =N—OH group is in the E configuration (GA3Ep). Some embodiments specifically include one or more specific substituents at one or more of the variable positions. Some embodiments specifically include one or more of the alternatives, while other embodiments specifically exclude one or more of these alternatives.

With respect to GAG3, in some embodiments the RARγ selective agonist has the structure

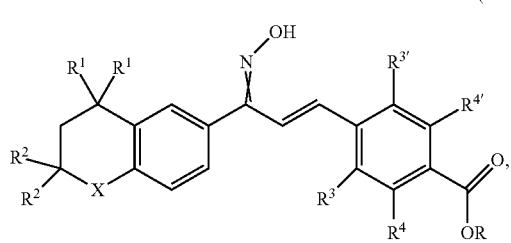

(GAG3p)

and other embodiments have the structure

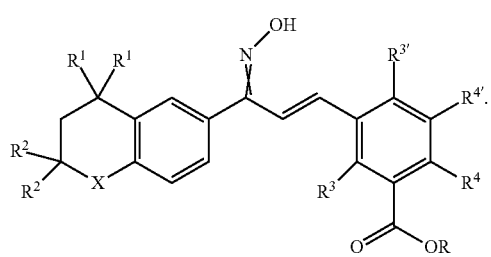

(GAG3m)

With respect to GAG3, in some embodiments the RARγ selective agonist has the structure

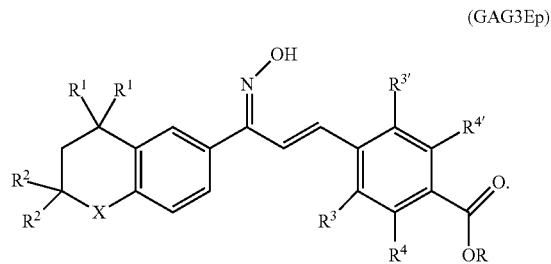

(GAG3Ep)

In some embodiments, the RARγ selective agonist is a compound with the structure

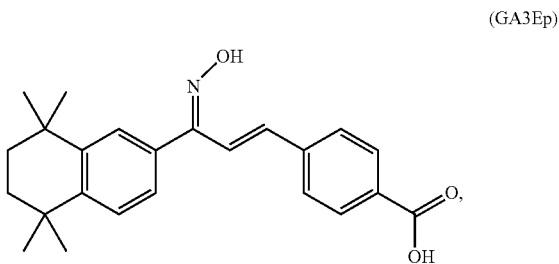 [SMILES: CC1(C)CCC(C)(C)c2cc(C(/C=C/c3ccc(C(=O)O)cc3)=N/O)ccc21]

(GA3Ep)

and in other embodiments, the RARγ selective agonist is a compound with the structure

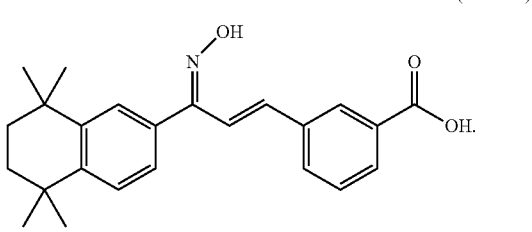

(GA3Em)

With respect to any of the preceding RARγ selective agonists of this section comprising a COOR group, in some embodiments R is H. In embodiments in which R is C₁₋₆ alkyl, the alkyl part of the ester has anywhere from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having anywhere from 1-6 carbon atoms, etc. The various subsets (including individual species) and combinations of these esters are contemplated as further distinct embodiments, including straight-chain, branched, and/or cyclic moieties of any length or set of lengths within the C₁₋₆ alkyl genus.

With respect to any of the preceding RARγ selective agonists of this section comprising a =N—OH group, some embodiments comprise either configuration, while other embodiments comprise only the E configuration, and still other embodiments comprise only the Z configuration, of this group.

With respect to any method of use aspect, in some embodiments the RARγ selective agonist is tazarotenic acid (selective for RARγ over RARα, but not over RARβ), CD437, CD2325, CD666, trifarotene, or BMS961.

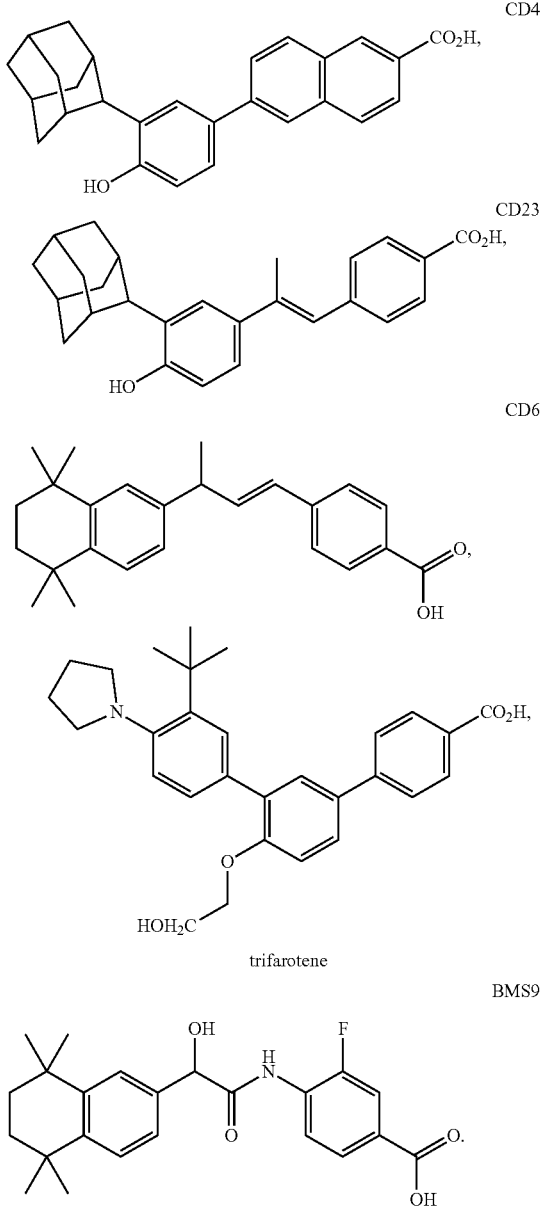

In some embodiments, the RARγ agonist is a RARγ-selective agonist in that it has no or only negligible agonistic activity with RARα and RARβ at clinically relevant concentrations. In some embodiments, the RARγ agonist is a RARγ-selective agonist in that it has no or only negligible agonistic activity with RARα at clinically relevant concentrations. In various embodiments, a RARγ selective agonist has no or only negligible agonistic activity with RARα or RARβ at some clinically relevant concentrations when the agonist's KD for RARγ is greater than 10-, 20-, 50-, or 100-fold lower than for the other RAR(s). KD is typically determined in a binding assay. In various embodiments, a RARγ selective agonist has no or only negligible agonistic activity with RARα or RARβ at some clinically relevant concentrations when the agonist's $EC_{50}$ with RARγ is greater than 10-, 20-, 50-, or 100-fold lower than for the other RAR(s). $EC_{50}$, is typically determined in an activation assay, for example, a transactivation assay. In some embodiments where a specific criteria of selectivity is not stated, the RARγ selective agonist meets at least one of these criteria, for example the least stringent.

These RARγ agonists constitute means for activating RARγ, or means for generating, differentiating, or expanding TIL. Some embodiments specifically include one or more of the disclosed genera, sub-genera, or species of these RARγ agonists. Some embodiments specifically exclude one or more of the disclosed genera, sub-genera, or species of these RARγ agonists.

EXAMPLES

The following non-limiting examples are provided for illustrative purposes only in order to facilitate a more complete understanding of representative embodiments now contemplated. These examples should not be construed to limit any of the embodiments described in the present specification.

Example 1

Synthesis of GAG1

The synthetic scheme for the synthesis of species of GAG1, GA1E and GA1Z, are presented in FIG. 1.

Ethyl-2-oxo-ethyl-5-bromo-salicylate-2-yl-butyrate

To a solution of ethyl-5-bromo-salicylate (Compound 1, 24.5 g, 100 mmol) in acetone (400 mL), were added ethyl-2-bromo butyrate (23.4 g, 120 mmol) and potassium carbonate (20.7 g, 150 mmol) and the mixture stirred for 24 h at ambient temperature. Solid material was removed by filtration and the solvent was removed by distillation to yield the title compound (not shown in FIG. 1) as a yellow oil. Yield=23.2 g.

5-Bromo-2-ethyl-benzofuran(2H)-3-one (Compound 2)

To a cold (0° C.) solution of ethyl-2-oxo-ethyl-5-bromo Salicylate-2-yl)-butyrate (23.2 g, 70.3 mmol) in dry toluene (300 mL) was added 20% sodium ethoxide in ethanol (27 g, 80 mmol) in small portions (5 min). The cooling bath was removed and the reaction was stirred at ambient temperature for 12 h. The reaction mixture was washed with water (25 mL) and brine (50 mL). The organic layer was dried and the solvent was removed by distillation under vacuum. The crude product was purified by silica gel column chromatography (10% ethyl acetate in hexane) to afford the title compound (Compound 2) as a white solid. Yield=16.5 g
$^1$HNMR (CDCl$_3$): δ 1.09 (triplet, 3H), 1.80-1.95 (m, 1H), 2.05-2.20 (m, 1H), 4.61 (t, 2), 7.12 (d, 1H), 7.70 (dd, 1H), 7.83 (d, 1H).

5-Bromo-3-t-butyl-2-ethyl-benzofuran (Compound 3)

To a cold (−78° C.) suspension of cerium chloride (25.41 g, 103 mmol) in THF (250 mL) was added t-BuMgCl in ether (2M, 41.2 mL, 82.4 mmol), and the resulting mixture stirred for 30 min. Then 5-bromo-2-ethyl-benzofuran(2H)-3-one (Compound 2) (16.5 g, 68.66 mmol) in THF (100 mL) was added and the mixture stirred at ambient temperature for 30 min. The reaction was quenched by adding MeOH (−78° C.), diluted with ethyl acetate (100 mL), washed with aq. NH$_4$Cl, water and brine (20 mL each). The organic layer was dried and the solvent was removed by distillation. The resulting residue was a mixture of the tertiary alcohol and unreacted compound 2, the mixture was used in the next step without further purification.

A mixture of the crude tertiary alcohol (obtained above), dichloromethane (300 mL) and p-TSA (200 mg) was stirred for 12 h at ambient temperature. The mixture was washed with aq. NaHCO$_3$, water and brine (100 mL each). The organic layer was dried and the solvent was removed by distillation. The residual crude product was purified by silicagel chromatography (3% ethyl acetate/hexane) to afford the title compound (Compound 3) as colorless oil. Yield=2.8 g $^1$HNMR (CDCl$_3$): δ 1.35 (triplet, 3H), 1.54 (s, 9H), 2.97 (q, 2H), 7.28 (d, 1H), 7.33 (dd, 1H), 7.88 (d, 1H).

1-(3-tert-butyl-2-ethyl-benzofuran-5-yl)-ethanone (Compound 4)

To a cold (−78° C.) solution of 5-bromo-3-t-butyl-2-ethyl benzofuran (Compound 3) (2.8 g, 10 mmol) in THF (60 mL) was added n-BuLi in hexane (2.5 M solution, 4.8 mL, 12 mmol). The mixture was gradually warmed to approximately 10° C. over 50 min, then cooled again to −78° C. and N-methoxyl-N-methylacetamide (1.23 g, 12 mmol) was added via syringe (neat). Cooling was removed and the reaction was stirred at ambient temperature for 12 hr. The reaction was quenched by adding aq. NH$_4$Cl, and the mixture was stirred for 15 min. The mixture was diluted with ethyl acetate (60 mL) washed with water and brine (10 mL each). The organic layer was dried and the solvent was removed by distillation. The product (Compound 4) was purified by silica gel chromatography (7% ethyl acetate in hexane), yield=2.1 g.

$^1$HNMR (CDCl$_3$): δ 1.33 (triplet, 3H), 1.55 (s, 9H), 2.68 (s, 3H), 2.97 (q, 2H), 7.87 (d, 1H), 8.41 (d, 2H).

4-[(E)-3-(3-tert-butyl-2-ethyl-benzofuran-5-yl)-3-oxo-prop-1-enyl]-3-fluoro-benzoic acid (Compound 5)

Methyl 3-fluoro-4-formylbenzoate (1.56 g, 8.6 mmol) was added to a solution of 1-(3-tert-butyl-2-ethyl-benzofuran-5-yl)-ethanone (Compound 4) (2.1 g 8.6 mmol) in 10 mL of 1 N sodium hydroxide and 20 mL of methanol. After stirring at room temperature for 18 h, the reaction mixture was acidified with 1N HCl and extracted with ethyl acetate (3×10 mL). The combined organic layer was washed with brine (1×10 mL), dried (MgSO4) and concentrated at reduced pressure. The product (Compound 5) was purified by silicagel chromatography (50% ethyl acetate in hexane), yield=1.6 gram.

$^1$HNMR (CDCl$_3$): δ 1.39 (triplet, 3H), 1.60 (s, 9H), 3.02 (q, 2H), 7.32 (s, 1H), 7.51 (d, 1H), 7.83 (t, 1H), 7.85 (d, 1H), 7.92 (d, 1H), 7.99 (d, 1H), 8.03 (d, 1H), 8.52 (d, 1H).

4-[(E,3E)-3-(3-tert-butyl-2-ethyl-benzofuran-5-yl)-3-hydroxyimino-prop-1-enyl]-3-fluoro-benzoic acid (GA1E)

To a solution of 4-[(E)-3-(3-tert-butyl-2-ethyl-benzofuran-5-yl)-3-oxo-prop-1-enyl]-3-fluoro-benzoic acid, (Compound 5) (1.60 g, 4.06 mmol) in 10 mL of ethanol was added hydroxylamine hydrochloride (653 mg, 9.40 mmol) and pyridine (1.86 g. 23.5 mmol). The reaction mixture was then heated at reflux for 6 h. After cooling to room temperature, the solvent was removed in vacuo and the residue was taken up in water. The aqueous layer was adjusted to pH 4-5 with 1 N HCl and the product was isolated by filtration. Further purification was done by silica gel chromatography (10% methanol/1% triethylamine/dichloromethane), yield=660 mg of pure E-isomer (GA1E) and 98 mg of impure Z-isomer (GA1Z) due to incomplete separation.

GA1E: $^1$HNMR (DMSO-D6): δ 1.31 (triplet, 3H), 1.50 (s, 9H), 2.97 (q, 2H), 6.95 (d, 1H), 7.38 (d, 1H), 7.57 (d, 1H), 7.71 (d, 1H), 7.82 (d, 1H), 7.86 (s, 1H), 7.90 (d, 1H), 7.97 (t, 1H).

Example 2

Specificity of Binding and Activity of GA1E and GA2E

Transactivation assays were conducted to test the specificity of binding activity of GA1E and GA2E for RARα and RARγ. Retinoic acid receptor transactivation activity and binding efficiencies were determined essentially as described in U.S. Pat. Nos. 5,298,429 and 5,071,773, incorporated by reference herein for all they teach regarding transactivation assays. Transactivation assays employed expression plasmids encoding the full-length receptors RARα and RARγ. Reporter plasmids containing the herpes virus thymidine kinase promoter and the appropriate retinoic acid receptor response element (RAREs) were positioned upstream of an open coding region encoding firefly luciferase.

Figure 3A:
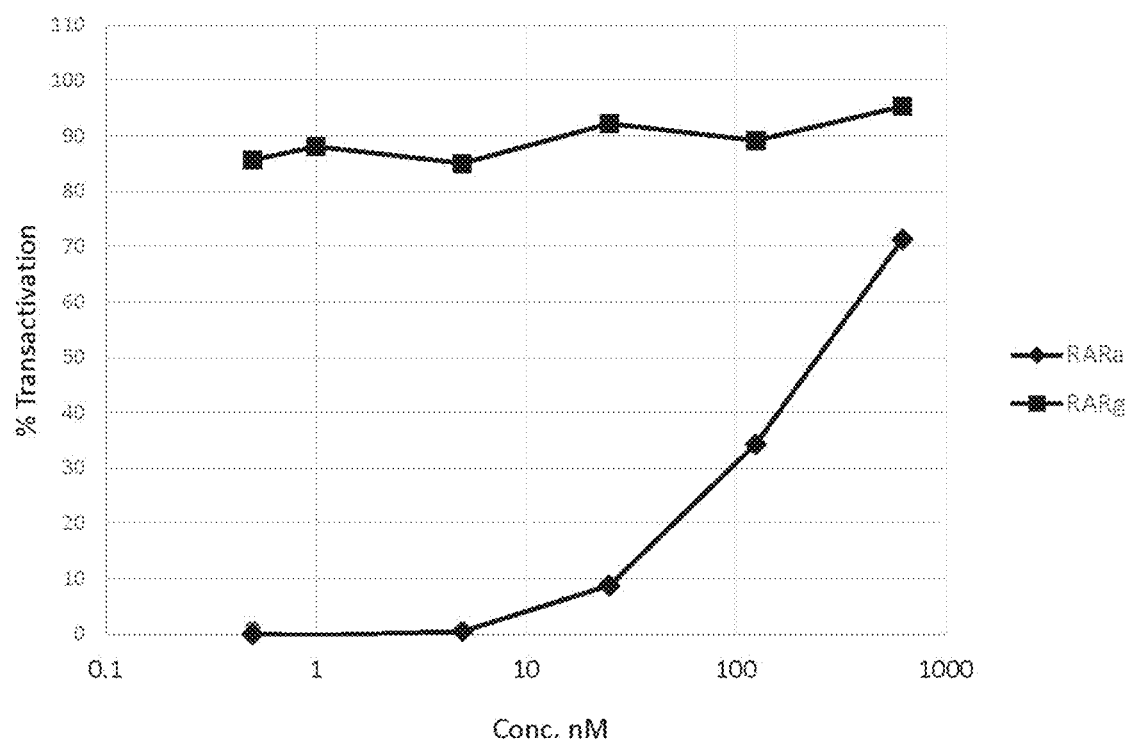
FIGS. 3A-B depict the results of RARα and RARγ transactivation assays of GA1E (FIG. 3A) and GA2E (FIG. 3B).
Figure 3B:
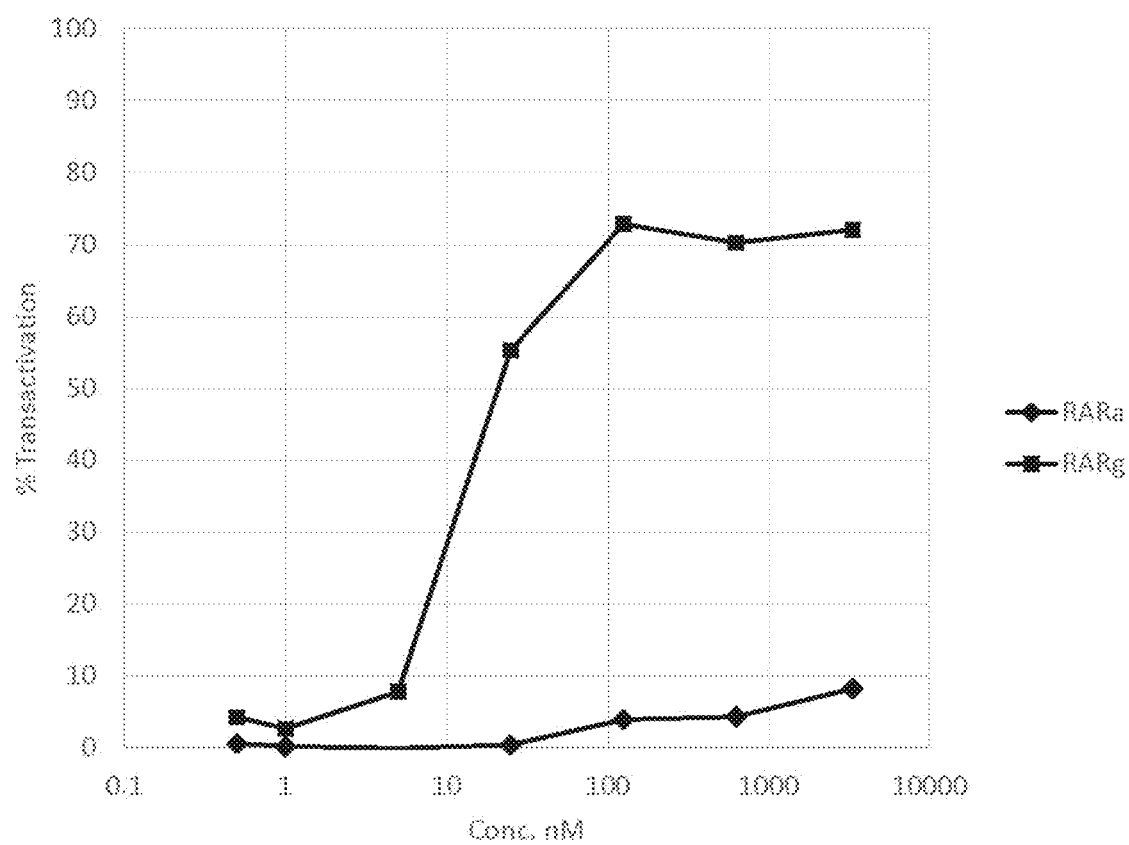

The ability of GA1E and GA2E to activate RARα and RARγ in a transactivation assay was tested over a concentration range of 0.5 to 625 nM (GA2E) or 0.05 to 3320 nM (GA1E). GA1E induced less than 10% transactivation for RARα across the whole concentration range, but over 50% transactivation for RARγ at concentrations ≥25 nM and over 70% at concentrations ≥125 nM (FIG. 3A). GA2E induced more than 85% transactivation at all tested concentrations and less than 10% transactivation of RARα at concentrations of:25 nM (FIG. 3B).

Example 3

Treatment of Triple Negative Breast Cancer in Mice with RARγ Agonists

The RARγ agonists tazarotenic acid and GA2E were evaluated in the EMT6 syngeneic mouse model of breast cancer. 5×10$^5$ EMT6 cells were injected into the mammary fat pad of immunocompetent female Balb/c mice. When the tumors reached an average volume of 50-150 mm$^3$, mice were matched by tumor size into control or treatment groups (n=10-11).

The mice were treated with 21 daily oral doses 10 mg/kg of 1 mg/ml tazarotenic acid or GA2E, or vehicle control, starting on Day 0. Tumor volume was measured, and the mice weighed, on days 0, 1, 3, 6, 8, 10, 13, 15, 17, 20, and 21.

Figure 4A:
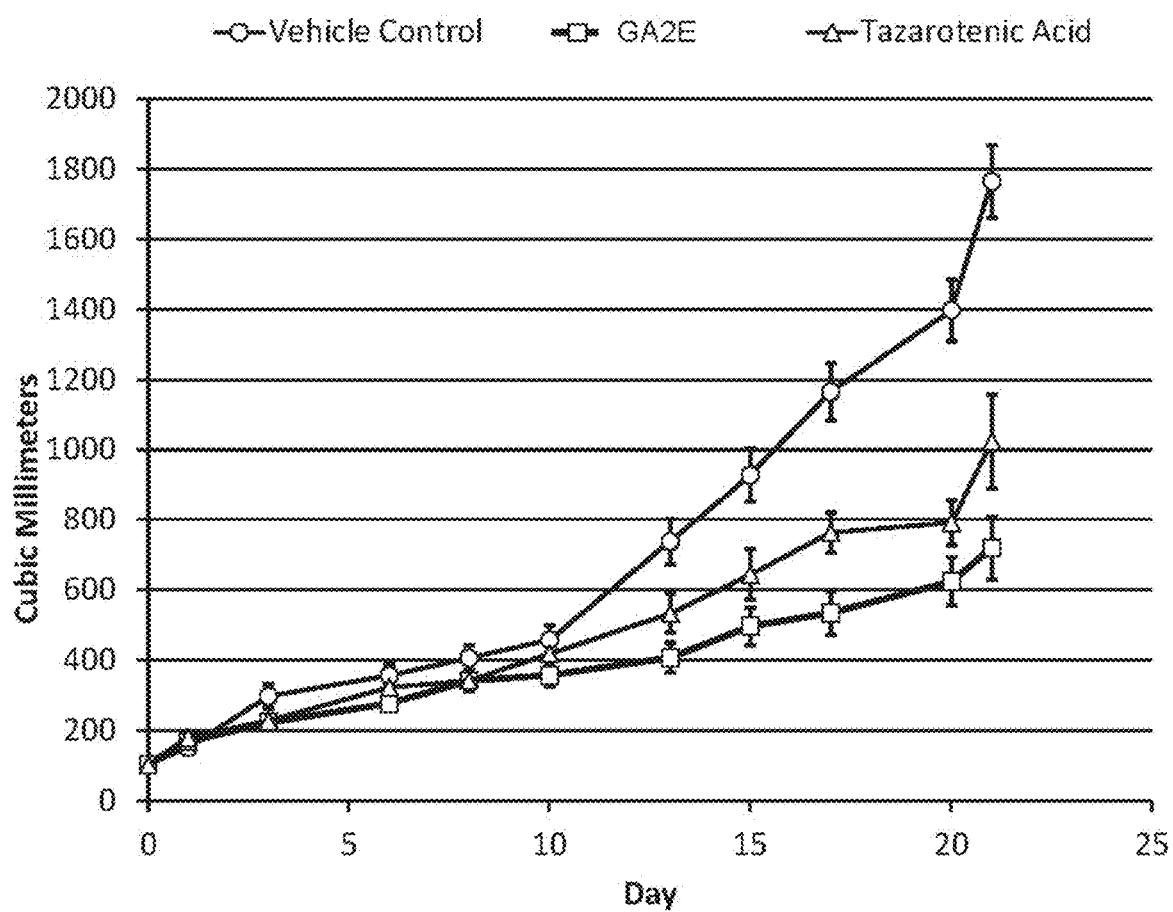
FIGS. 4A-B depict the results of treating a triple negative breast cancer in a syngeneic, immunocompetent mouse model with the RARγ selective agonists tazarotenic acid and GA2E, versus vehicle control.
Figure 4B:
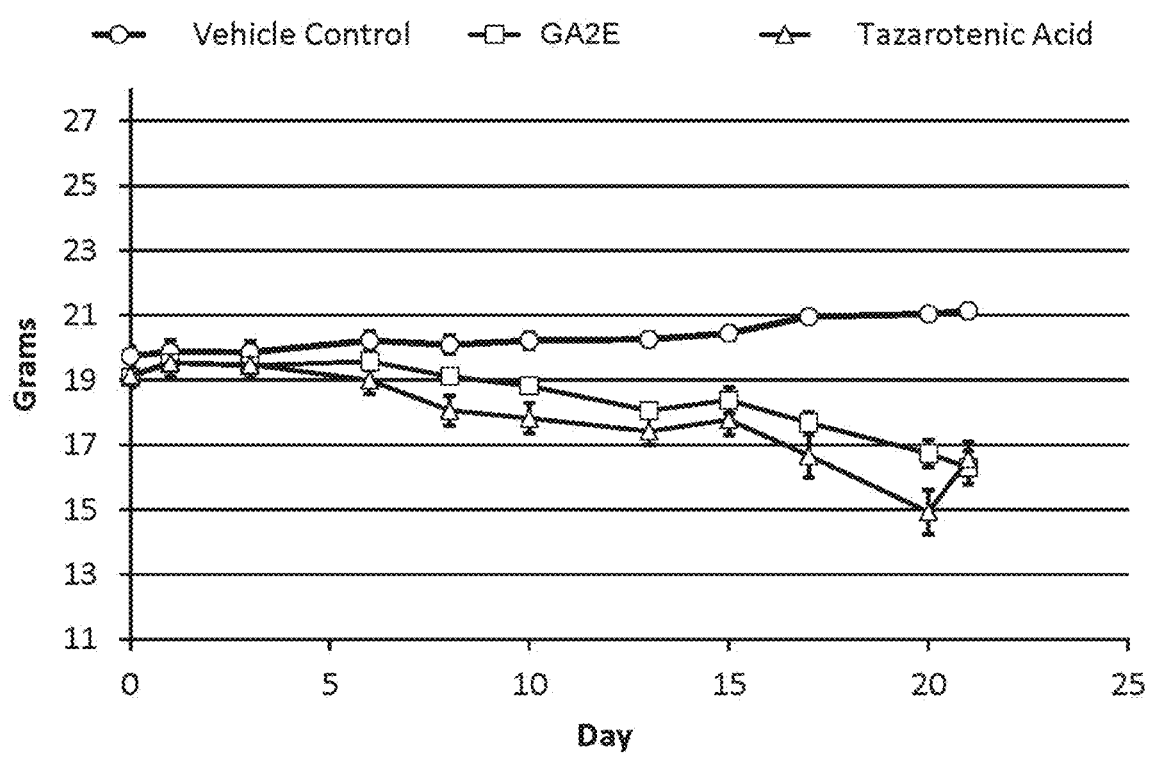

Both tazarotenic acid and GA2E inhibited tumor growth, with GA2E having the greater efficacy (FIG. 4A). The inhibition of tumor growth did not become apparent until more than 10 days after dosing had begun. At the end of the study, tazarotenic acid had inhibited tumor growth by 44% and GA2E by 63%. While the vehicle control group had a small weight gain, both treatment groups experienced similar but modest weight loss, between 15 and 20% (FIG. 4B), indicating the drug was acceptably well-tolerated for a cancer therapeutic.

Example 4

Figure 5A:
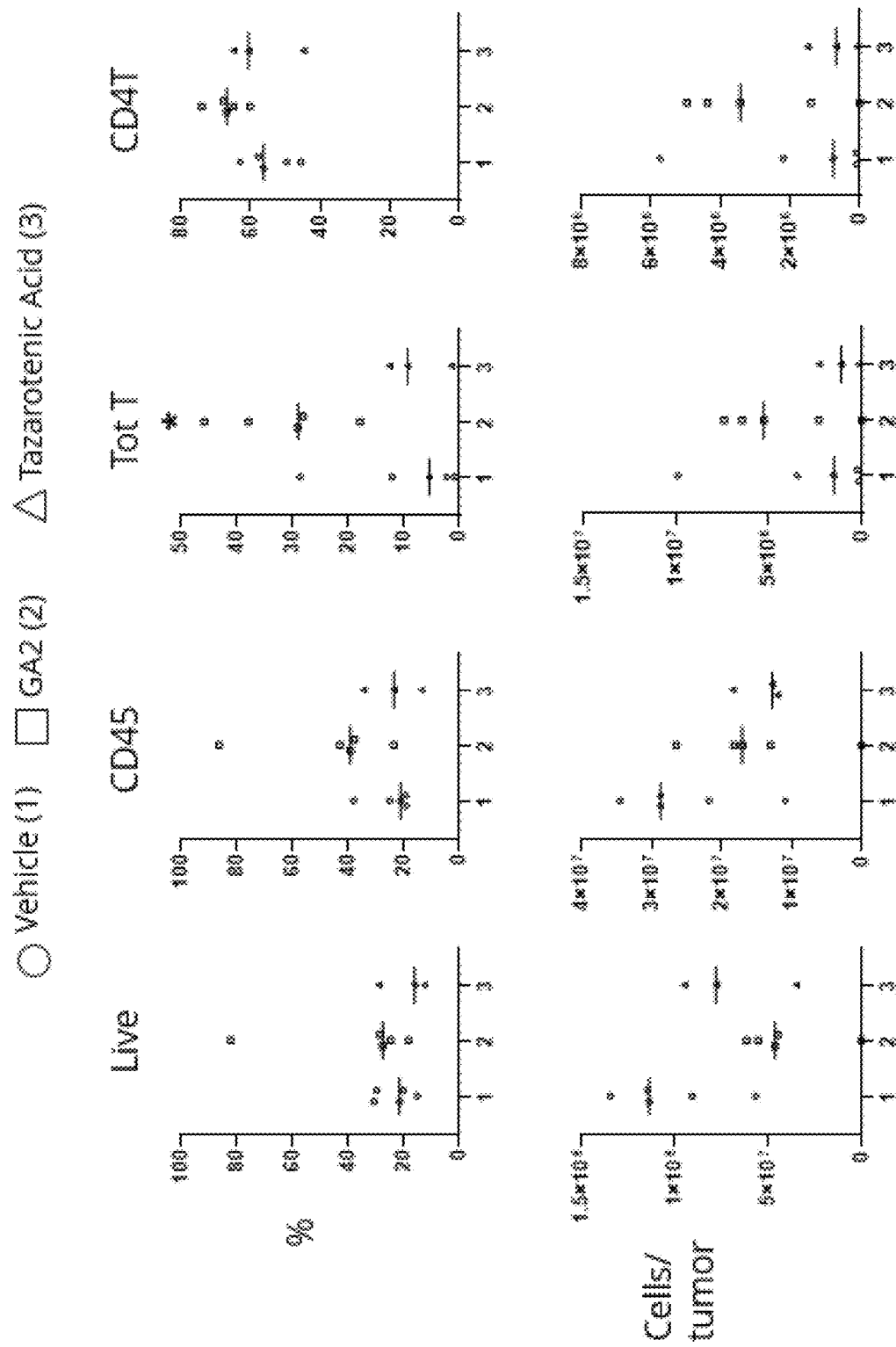
FIGS. 5A-B depict the results of flow cytometric analysis of tumors excised at the end of the study described in Example 3, for each of the treatments, GA2E, tazarotenic acid, and vehicle control. Results are shown both as percentage (upper panels) and absolute number of cells/tumor (lower panels).
Figure 5B:
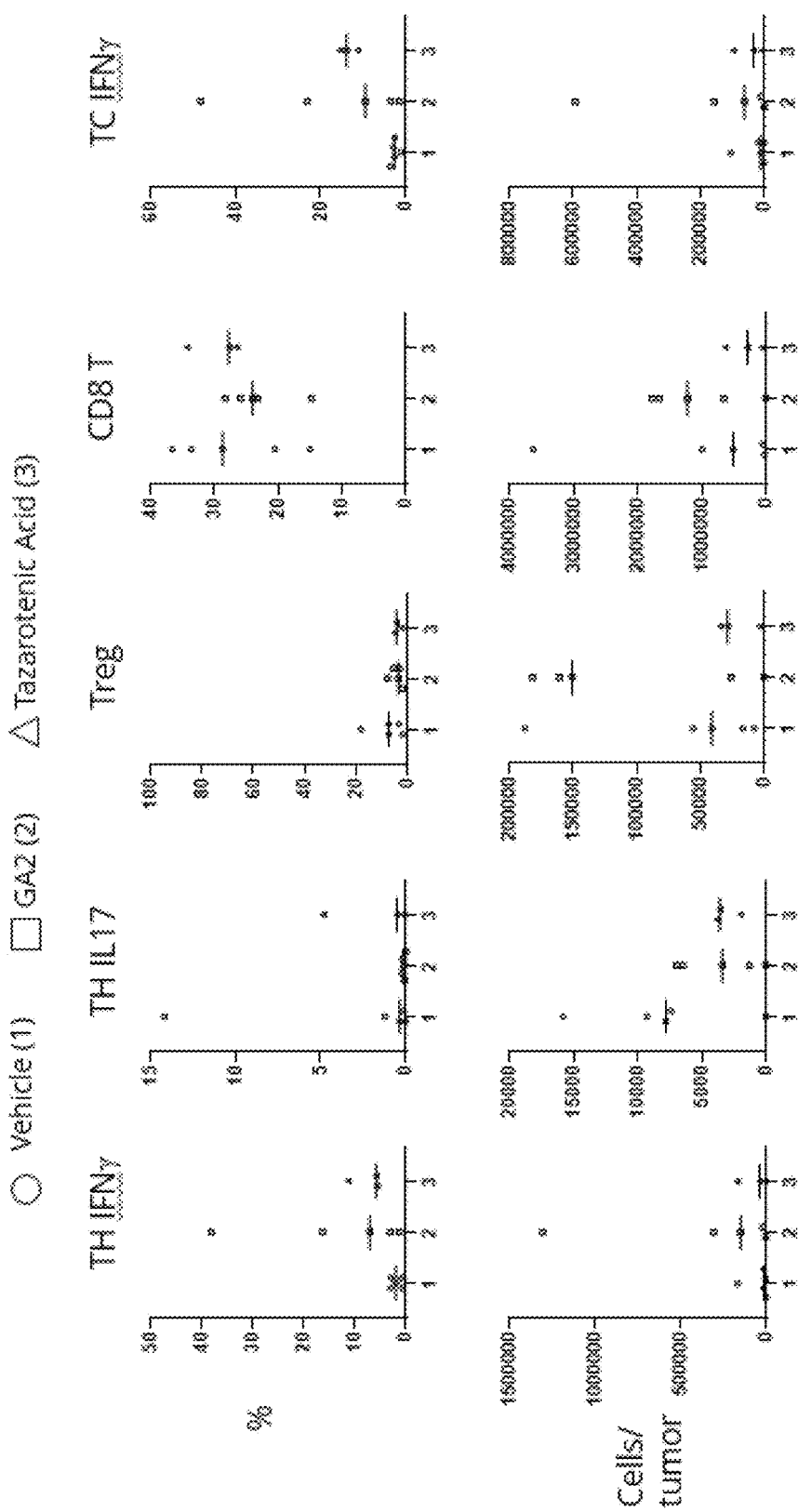

Increased TIL in Tumors from Triple Negative Breast Cancer in Mice with an RARγ Selective Agonist At the end of the study of Example 3, the tumors were excised, the cells disaggregated and dispersed without use of proteases, stained with various agents, and subjected to flow cytometry. FIG. 5A-B present the results of the flow cytometry both as a percentage of cells and as the number of cells per tumor. Generally, only a minority of cells in the tumor were alive, as revealed by staining with the dye FVS700, which penetrates and stains necrotic cells (FIG. 5A, "Live" panel). Of these live cells, a substantial proportion were leukocytes (FIG. 5A, "CD45" panels). Staining with anti-CD3 (FIG. 5A, "Tot T" panels) revealed a mean of only about 5% and 10% of the leukocytes were T cells for the vehicle and tazarotenic acid treated mice, respectively, but in the tumors from the mice treated with GA2E a mean of about 30% of the leukocytes were T cells; a statistically significant difference. The majority of the T cells were $CD4^+$ (FIG. 5A, "CD4' panels), expected to be predominantly helper cells. Of the $CD4^+$ cells, only small proportions were T memory cells (expected to be predominantly TH1 memory cells) based on intracellular staining for IFNγ (FIG. 5B, "TH IFGγ" panels), TH17 cells based in intracellular staining for IL-17 (FIG. 5B, "TH IL17" panels), or Treg cell based on staining for CD25 and FoxP3 (FIG. 5B, "Treg" panels). About 25-30% of the T cells were $CD8^+$ (FIG. 5B, "CD8 T" panels), expected to be predominantly cytotoxic cells. The proportion of $CD8^+$ T cells that were memory cells, based on intracellular staining for IFNγ (FIG. 5B, "TC IFNγ" panels), was numerically increased in the tumors from the mice treated with tazarotenic acid and GA2E, though the difference from the vehicle control animals did not achieve statistical significance. Thus GA2E treatment increased the number of TIL.

Example 5

Treatment of Triple Negative Breast Cancer in Mice with Various Dosages of an RARγ Agonist The EMT6 triple negative breast cancer model, essentially as described above, was used to assess the effects of increased dosages of GA2E. The mice were orally administered 10 (n=10), 25 (n=10), or 50 (n=11) mg/kg of GA2E, or vehicle control (n=10) daily for 17 days. However, all of the mice in the 50 mg/kg group were terminated for excessive weight loss not later than Day 12, as was one mouse in the 25 mg/ml group. Two mice in the vehicle control group were terminated at Day 12 with tumors >1500 $mm^3$.

Figure 6A:
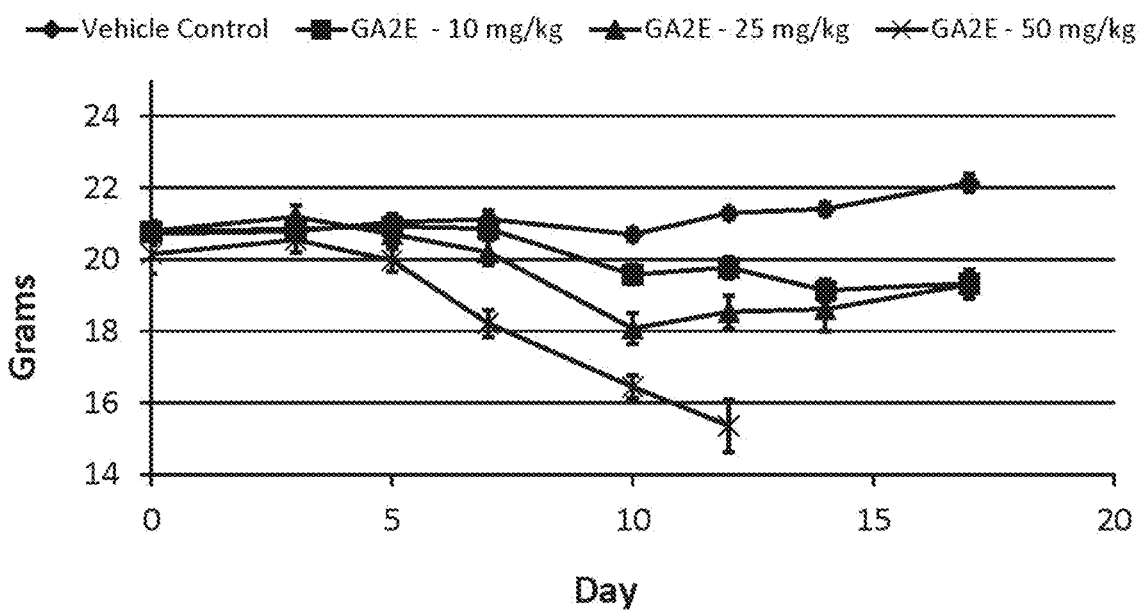
FIGS. 6A-B depict weight change in Balb/c mice implanted with EMT6 triple negative breast cancer cells in control mice (◆) and GA2E treated mice at 10 mg/kg (■), 25 mg/kg (▲), or 50 mg/kg (X) from the first day of treatment (Day 0) through the end of the study, reported as mass (FIG. 6A) or percent change (FIG. 6B).
Figure 6B:
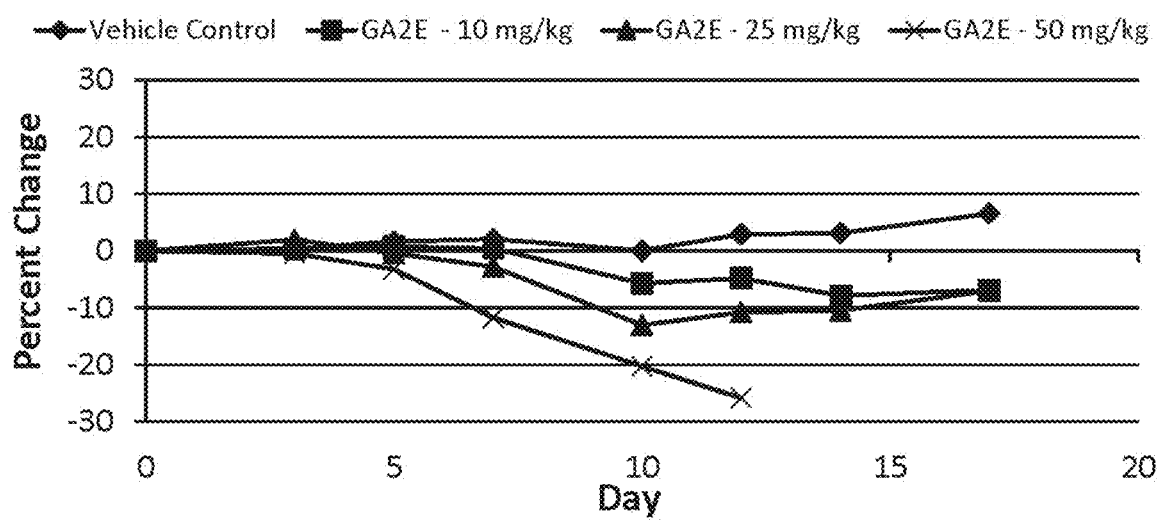

Overall, the 10 and 25 mg/kg were acceptably well-tolerated for a cancer therapeutic, with only a short excursion to more than 10% weight loss for the 25 mg/kg dosage (FIGS. 6A-B). The 25 mg/kg dosage was somewhat more effective at inhibiting tumor growth than the 10 mg/kg dosage. The tumor inhibition by the 50 mg/kg dosage was not clearly different than that of the other dosages in the limited time those animals were in the study (FIG. 7). Scaling to human according to body surface area, 10 and 25 mg/kg in the mouse correspond to approximately 0.8 and 2.0 mg/kg in humans, respectively.

Example 6

RARγ Selective Agonists Promote Activity and Proliferation of $CD8^+$ Memory T Cells Peripheral blood mononuclear cells (PBMC) from a cytomegalovirus (CMV)-positive donor were labeled with carboxyfluorescein succinimidyl ester (CFSE) and stimulated with CMV recall antigens at 1 mg/ml. The PBMC were then treated with one of three difference RARγ selective agonists or vehicle (DMSO) control and incubated at 37° C., 5% $CO_2$ for four days. Culture supernatant was harvested and assayed for IFNγ production and the PBMC evaluated for proliferation by flow cytometry for CFSE dilution.

CFSE is a fluorescent reactive cell membrane permeable dye. After it is taken up, CFSE covalently modifies proteins and is retained in cells for long periods of time. The CFSE-modified proteins are generally evenly divided between daughter cells at each division so that fluorescent intensity of the cells falls by have at each division. Thus diminution of the dye's fluorescent signal can be used as a measure of proliferation.

Figure 9C:
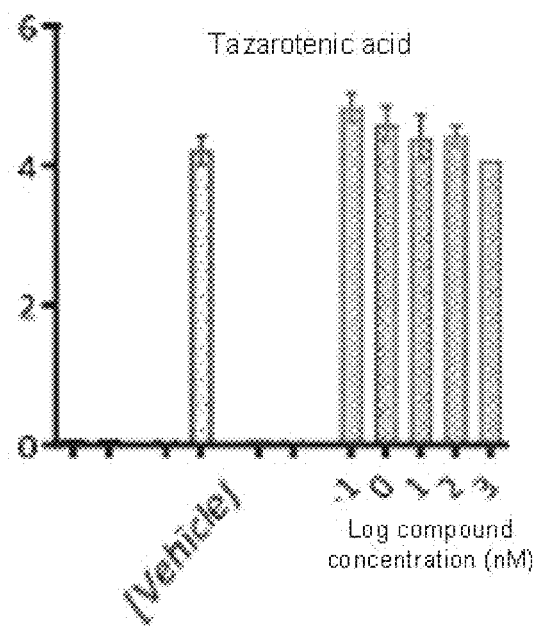

Treatment with RARγ selective agonists increased IFNγ production substantially over the vehicle control at concentrations of 0.1 to 1000 nM for each of GA2E, GA3Ep, and tazarotenic acid (FIGS. 8A-C). Proliferation of $CD8^+$ cells was also increased (FIG. 9A-C). Although the increase over the background level of proliferation is small, it is still quite meaningful as only a small proportion of the $CD8^+$ cells would be expected to be specific for CMV.

Example 7

RARγ Selective Agonist Promotes Generation of Human $CD8^+$ Effector TIL and Tumor Shrinkage (NSG-B2m Model)

The NSG-B2M mouse model is a severely immunocompromised animal, combining the lesions non-obese diabetic (NOD), severe combined immunodeficiency (SCID), IL-2 receptor γ null, and β2-microglobulin null. Human tumor cells readily engraft in this model and cells from the human immune system can also be engrafted in order to study various modes of cancer immunotherapy. Thus, one can model a human immune response to a human tumor in this system. Female NSG-B2M mice were injected in the mammary fat pad with $5×10^6$ JIMT-1 cells (human breast carcinoma cell line) suspended in 0.1 mL of phosphate-buffered saline (PBS) with an equal volume of Matrigel®. Once tumors reached a volume of 100-200 $mm^3$, the mice were implanted with $1×10^7$ human PBMC by subcutaneous injection into the right flank (pre-randomization). PBMC were obtained from two donors and distributed evenly between groups. When tumors reached an average tumor volume of 200-250 $mm^3$ (about 3 days post-PBMC injection) animals were matched by tumor volume into treatment and control groups, and dosing initiated. This first day of dosing was defined as Day 0. The mice were administered a daily oral dose of 10 mL/kg of 10% dimethyl sulfoxide (DMSO) in PBS as vehicle control or 10 mg/kg of GA2E dissolved in 10% DMSO in PBS as the treatment.

Tumor volume was measured twice weekly and on the day a study endpoint was reached. The mice were also weighed twice weekly and on the day a study endpoint was reached. Animals exhibiting a weight loss from Day 0 of >10% were provided a food supplement ad libitum. Animals exhibiting a weight loss of >20% in any 7-day period or >30% from Day 0 were considered moribund and euthanized.

Study endpoint was defined as when the mean tumor volume of the control group (uncensored) reaches 1500 mm³. If this occurs before Day 28, treatment groups and individual mice were permitted to be dosed and measured up to Day 28. If the mean tumor volume of the control group (uncensored) did not reach 1500 mm³ by Day 28, then the endpoint for all animals was the day when the mean tumor volume of the control group (uncensored) reached 1500 mm³ up to a maximum of Day 60.

Figure 10A:
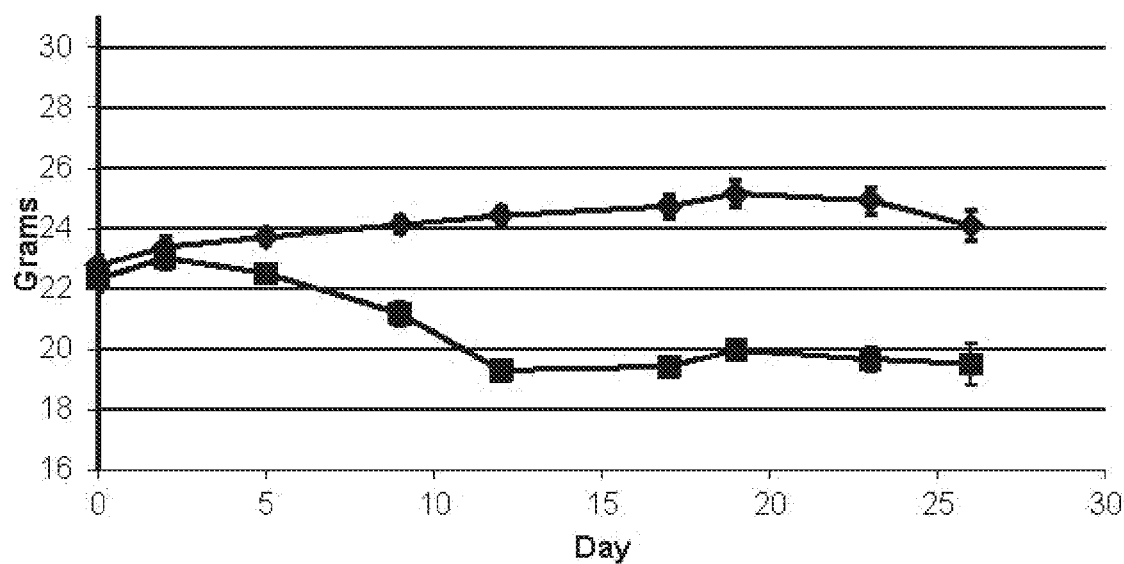
FIGS. 10A-B depict weight change in NSG-B2M mice implanted with a Her2⁺ breast cancer cell line (JIMT-1) and human PBMC in control (◆) and GA2E treated (■) mice, from the first day of treatment (Day 0) through the end of the study, reported as mass (FIG. 10A) or percent change (FIG. 10B).
Figure 10B:
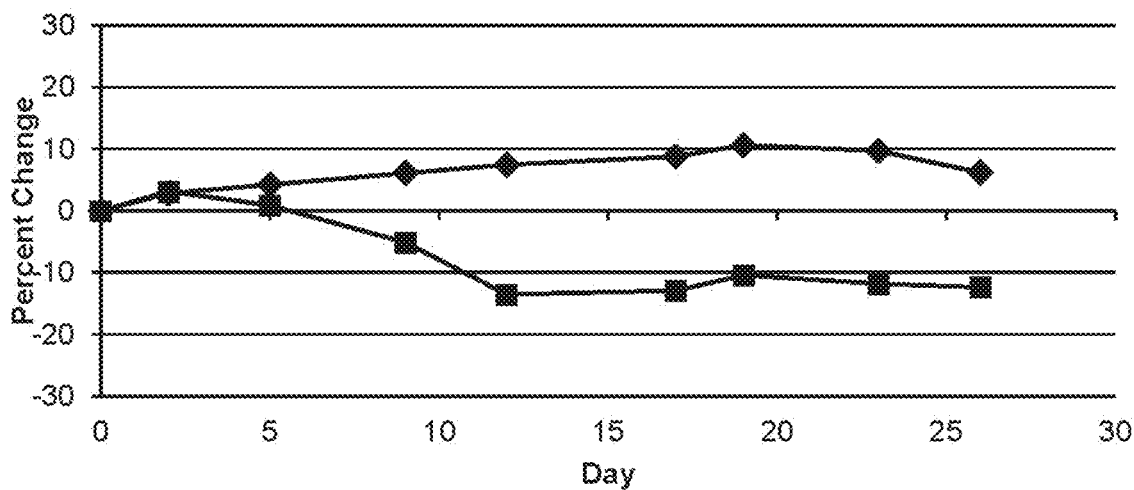
Figure 11:
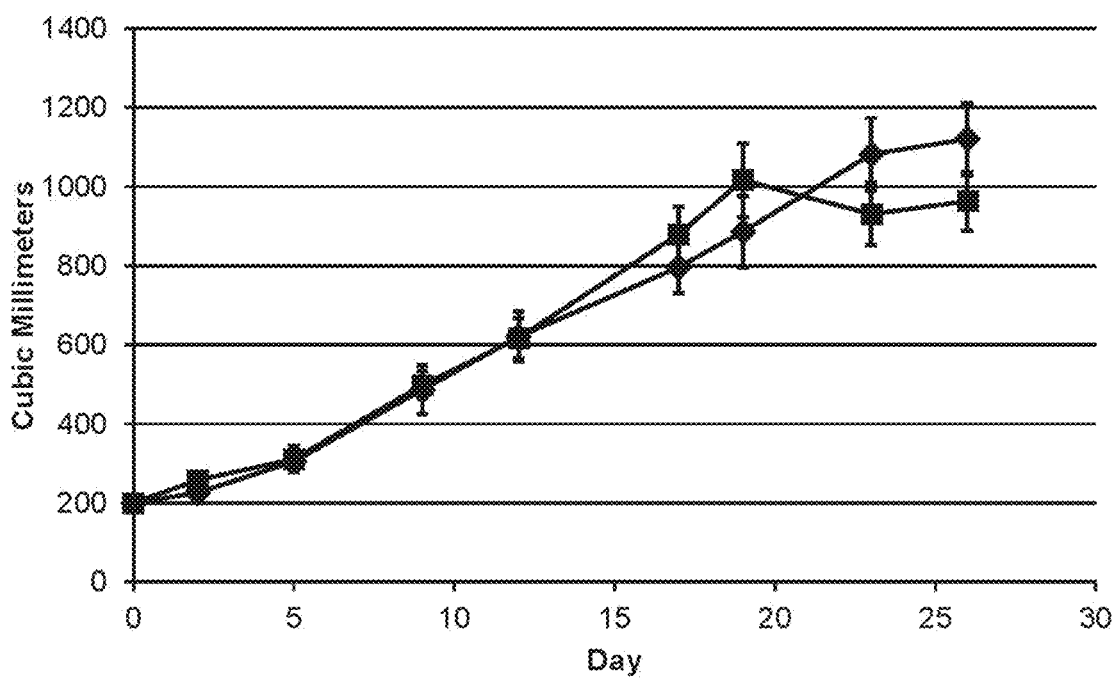
FIG. 11 depicts tumor growth, in mm³, in NSG-B2M mice implanted with a Her2⁺ breast cancer cell line (JIMT-1) and human PBMC in control (◆) and GA2E treated (■) mice, from the first day of treatment (Day 0) through the end of the study.

The GA2E-treated mice lost substantial weight, >10% by Day 12 of the study (FIG. 10A-B) and the animals were placed on drug holiday on Day 13 through the end of the study. No impact on tumor growth was observed while the mice were receiving GA2E, however, there was tumor shrinkage subsequent to Day 19 of the study (FIG. 11); and several of the mice showed shrinkage subsequence to day 17 (data not shown). These data suggest that the anti-tumor effects of RARγ agonists is not a direct effect on the tumor cells themselves, but are consistent with RARγ agonists promoting anti-tumor immunity.

The mice were sacrificed on Day 26 of the study and the tumors collected and analyzed by flow cytometry. Statistical analysis was by ordinary one-way ANOVA with Tukey's test for significance comparison between groups. Gates were set to identify single cells by forward light scatter, live cells as single cells based on side scatter and staining with the vital stain Fixable Viability Dye eFluor™ 780, white blood cells from live cells based on side scatter and staining with anti-CD45, lymphocytes from white blood cells based on side and forward light scatter, and total T lymphocytes (tot T) from lymphocytes based on side scatter and staining with anti-CD3. Total T lymphocytes were divided into $CD4^+$ (TH) and $CD8^+$ (TC) lymphocytes based on staining with and anti-CD4 and CD8 antibodies and subsets assessed. The following observations were made on a per-mg of tumor tissue basis.

Figure 12A:
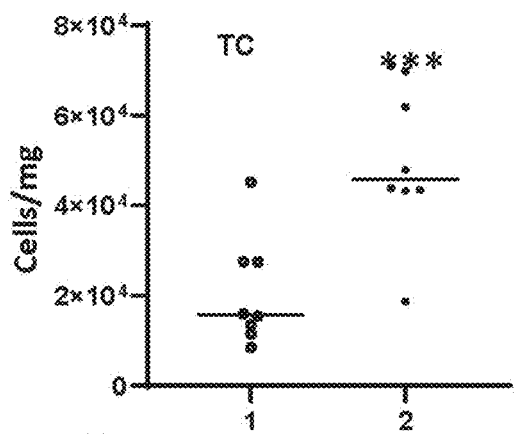
FIG. 12A-E depicts flow cytometric T subset analysis of CD8⁺ TIL from NSG-B2M mice implanted with a Her2⁺ breast cancer cell line (JIMT-1) and human PBMC in control (◆) and GA2E treated (■) mice on Day 26 (termination) of the study. The subsets were total CD8⁺ T cells (FIG. 12A, TC), naive CD8⁺ T cells (FIG. 12B, CD8 Naïve), central memory CD8⁺ T cells (FIG. 12C, CD8 TCM), effector memory CD8⁺ T cells (FIG. 12D, CD8 TEM), and terminally differentiated effector CD8⁺ T cells (FIG. 12E, CD8 TEFF). Significance of the difference between treated and control: * indicates P<0.05; *** indicates P<0.001; no asterisks indicates P>0.05.
Figure 12B:
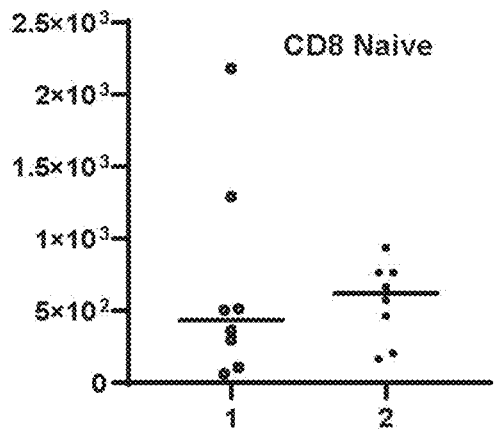
Figure 12C:
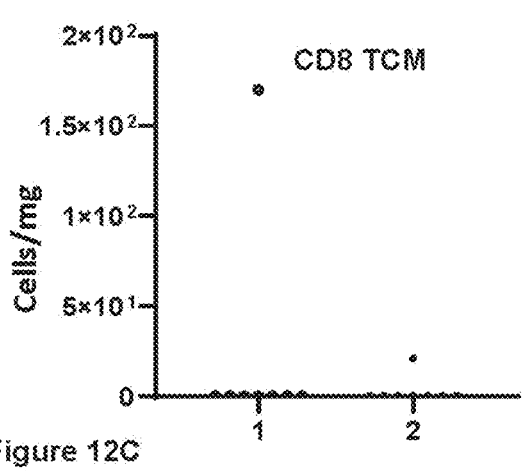
Figure 12D:
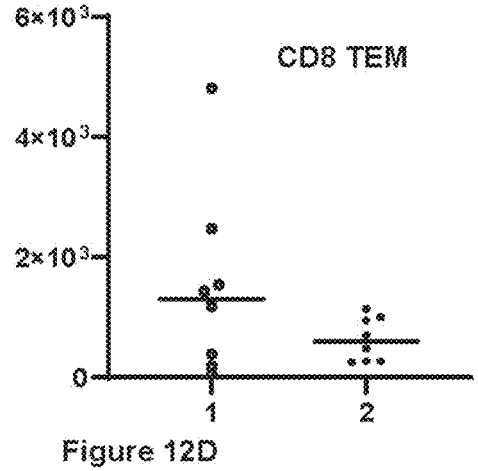
Figure 12E:
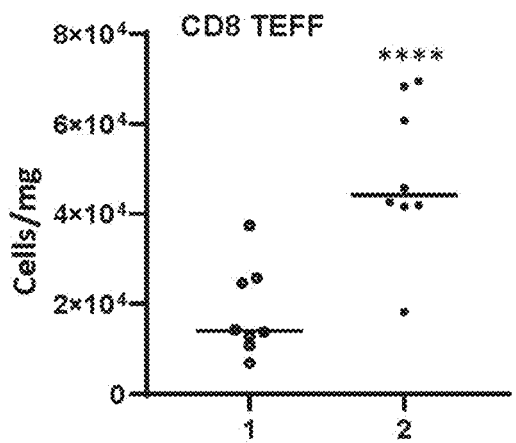

The concentration of total $CD8^+$ lymphocytes was increased in the GA2-treated tumors as compared to controls (FIG. 12A, $P<0.001$). There was no significant change in the concentration of naïve (defined as $CCR7^+$ $CD45AR^+$), T central memory ($CCR7^+$ $CD45AR^-$), or T effector memory ($CCR7^-$ $CD45AR^-$) subsets of $CD8^+$ cells in the tumors (FIGS. 12B, C, and D, respectively). However, there was a substantial increase the concentration of terminally differentiated $CD8^+$ T effector cells, defined as $CCR7^-$ $CD45AR^+$ (FIG. 12E, $P<0.0001$). CCR7 promotes homing to the lymph nodes, thus effector cells, found in the periphery are $CCR7^-$. That terminally differentiated $CD8^+$ T effector cells, expected to be cytolytic, are increased amongst TIL in shrinking tumors, is consistent with the interpretation that anti-cancer activity of RARγ agonists, such as GA2E, arises through an immunologic mechanism rather than a direct effect. The concentration of $CD8^+$ TIL expressing the T cell markers PD-1, CD18β, and CD54 was also increased in the GA2E-treated tumors as compared to controls (FIG. 13A, $P<0.0001$; FIG. 13B, $P<0.001$; and FIG. 13C, $P<0.01$; respectively). CD18 and CD54 are both involved in cell-cell adhesion and immune surveillance. Their increased presence in TIL suggests improved efficiency in forming the immunologic synapse and antigen recognition by the $CD8^+$ T effector cells. PD-1 is involved in immune homeostasis, facilitating down-regulation of immune responses, for example, through apoptosis of the effector cells expressing PD-1. The increase in $PD-1^+$ cells reflects an upregulated response. Antagonists of the PD-1/PD-L axis, such as anti-PD-1 and anti-PD-L1 antibodies (immune checkpoint inhibitors) may thus further augment the immune response promoted by RARγ agonists, such as GA2E.

Figures 15A, 15B:
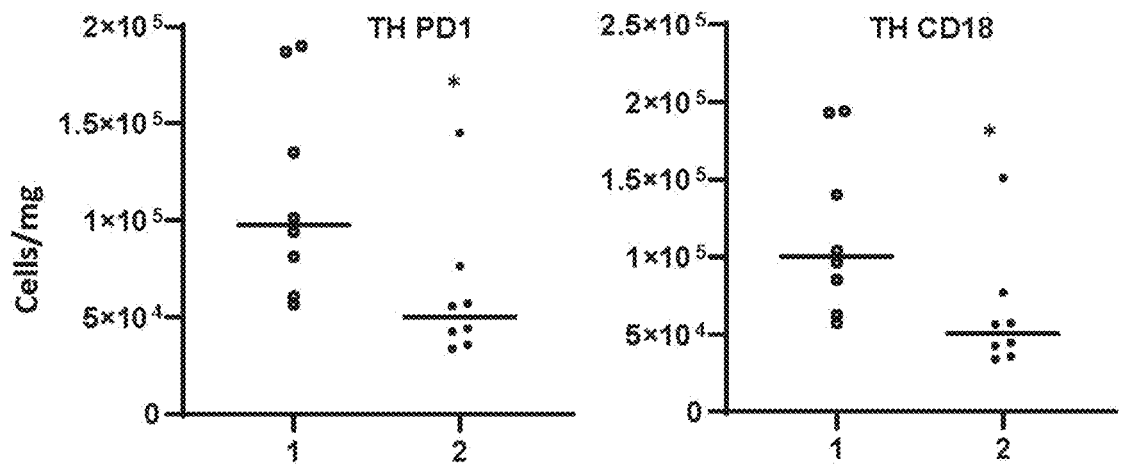
FIG. 15A-D depicts flow cytometric biomarker analysis of CD4⁺ TIL from NSG-B2M mice implanted with a Her2⁺ breast cancer cell line (JIMT-1) and human PBMC in control (◆) and GA2E treated (■) mice on Day 26 (termination) of the study. The subsets were PD-1⁺ CD8⁺ T cells (FIG. 15A, TH PD1), CD18β⁺ CD4⁺ T cells (FIG. 15B, TH CD18), CD54⁺ CD4⁺ T cells (FIG. 15C, TH CD54), and Fox3P⁺ CD4⁺ T cells (FIG. 15D, Tregs). Significance of the difference between treated and control: * indicates P<0.05; no asterisks indicates P>0.05.
Figures 15C, 15D:
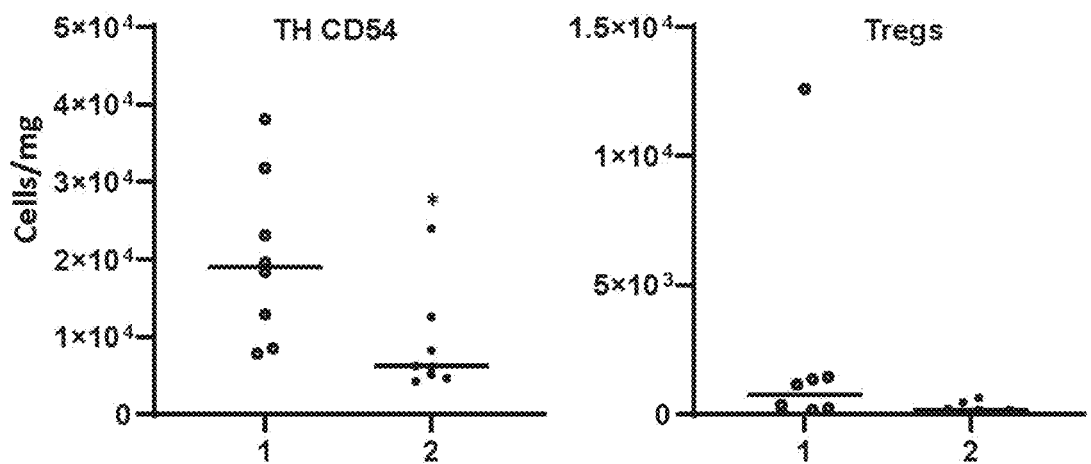

The concentration of total CD4+ lymphocytes was decreased (FIG. 14A; $P<0.05$), as were all of the tested subsets: naïve (defined as $CCR7^+$ $CD45AR^+$), T central memory ($CCR7^+CD45AR^-$), T effector memory ($CCR7^-$ $CD45AR^-$) terminally differentiated $CD4^+$ T effector cells ($CCR7^-$ $CD45AR^+$) (FIGS. 14B, C, and D, $P<0.05$ each, and FIG. 14D, $P>0.05$, respectively). The concentration of $CD4^+$ TIL expressing the T cell markers PD-1, CD18β, CD54, and FoxP3 was also increased in the GA2-treated tumors as compared to controls (FIG. 15A, $P<0.05$; FIG. 15B, $P<0.05$; FIG. 15C, $P<0.05$; and FIG. 15D, $P>0.05$; respectively).

The effect of treatment with the RARγ agonist GA2E, in this model of human anti-tumor immune response, was to substantially increase the concentration of $CD8^+$ TIL in the tumor, especially of terminally differentiated effector cells. In contrast, the concentration of $CD4^+$ TIL in the tumor was decreased. Similarly, whereas the concentration $PD-1^+$, $CD8β^+$ and $CD54^+$ $CD8^+$ TIL was increased, it was decreased $CD4^+$ TIL. All of these data are consistent with promotion of a $CD8^+$ effector cell-based TIL antitumor response accompanied by a diminished $CD4^+$ response. Applicants are not aware of another class of small molecule agents that specifically increases $CD8^+$ effector cells in the TIL population. The desirability of such an effect for cancer treatment is manifest.

The tumor cells were also assessed by flow cytometry for expression of PD-L1, CD18β, CD58 (LFA-3), and Her2. Treatment with GA2E did not significantly alter the proportion of cells expressing these markers, consistent with RARγ agonists not having a direct effect on the tumor cells.

Example 8

Figure 16:
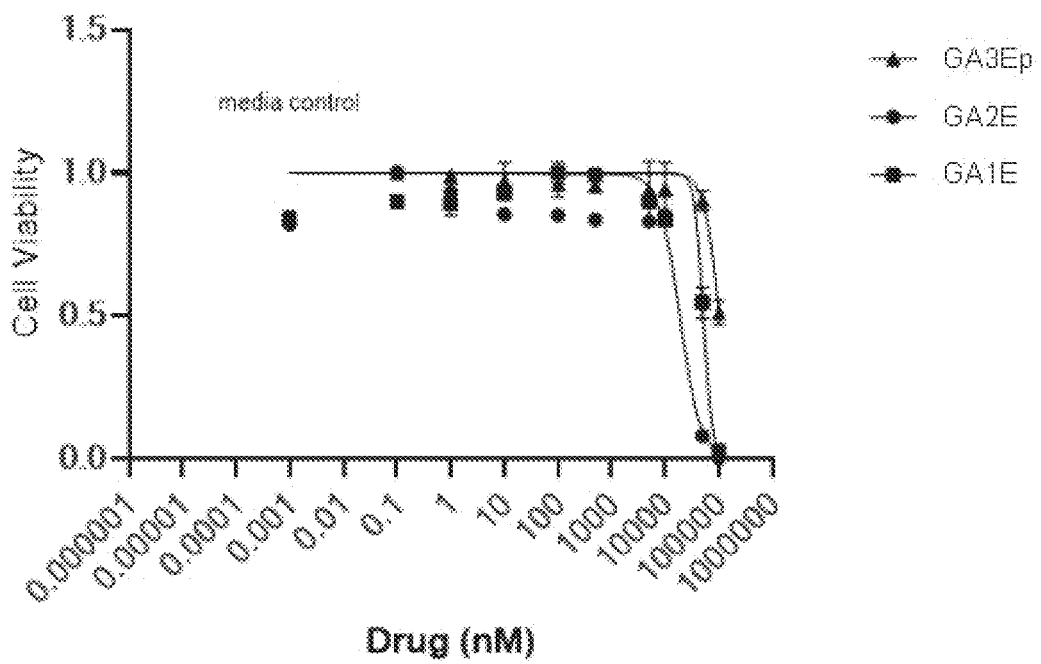
FIG. 16 depicts dose-response curves for cell viability for EMT6 cells grown in the presence of three RARγ agonists GA1E (■), GA2E (•), and GA3Ep (▲).

Effect of RARγ Agonists on In Vitro Culture of Triple Negative Breast Cancer Cell Line EMT6 cells were cultured in vitro for 5 days the presence of a multiple concentrations of the RARγ agonists GA1E, GA2E, and GA3Ep and viability assessed by the Cell Titer Glo Assay® (Promega). The compounds had no effect at concentrations below 1 μM, but rapidly became toxic as concentrations exceeded 10 μM (FIG. 16). The $IC_{50}$ for GA1E, GA2E, and GA3Ep were 52 μM, 19 μM, and 101 μM for GA1E, GA2E, and GA3Ep, respectively. These data confirm that the anti-cancer effects of the RARγ agonists observed in vivo arise not from a direct effect on the tumor cells but, most likely, from promotion of a TIL-based antitumor immune response. That is, at the concentrations used, the RARγ agonists did not directly inhibit tumor growth, and therefore their tumor inhibitory effect arises from their promotion of TIL.

Example 9

Effect of RARγ Agonists on In Vitro Culture of Lewis Lung Cancer Cell Line

Figure 17:
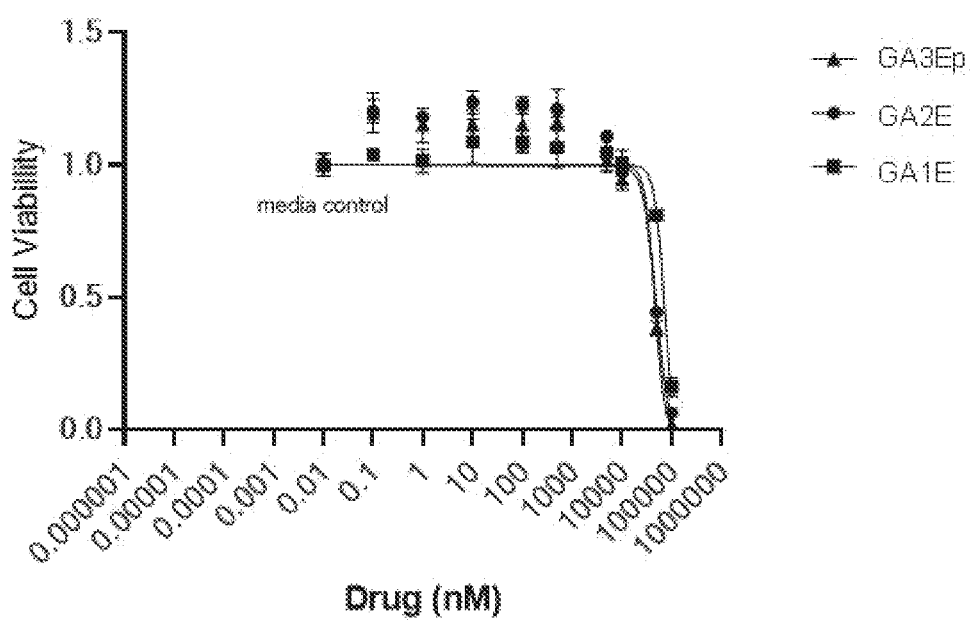
FIG. 17 depicts dose-response curves for cell viability for Lewis Lung carcinoma (LLC) cells grown in the presence of three RARγ agonists GA1E (■), GA2E (•), and GA3Ep (▲).

Lewis lung carcinoma (LLC) cells were cultured in vitro the presence of a multiple concentrations of the RARγ agonists GA1E, GA2E, and GA3Ep and viability assessed by the Cell Titer Glo Assay®. The compounds had no effect at concentrations below 1 µM, but rapidly became toxic as concentrations exceeded 10 µM (FIG. 17). The $IC_{50}$ for GA1E, GA2E, and GA3Ep were 96 µM, 46 µM, and 45 µM for GA1E, GA2E, and GA3Ep, respectively. These data confirm that the anti-cancer effects of the RARγ agonists observed in vivo arise not from a direct effect on the tumor cells but, most likely, from promotion of a TIL-based antitumor immune response. That is, at the concentrations used, the RARγ agonists did not directly inhibit tumor growth, and therefore their tumor inhibitory effect arises from their promotion of TIL.

Example 10

RARγ Selective Agonist Promotes Generation of Human $CD8^+$ Effector TIL and Tumor Shrinkage (LLC Model)

The LLC model is based on an epidermoid carcinoma of the lung that spontaneously arose in a C57BL/6 mouse some 70 years ago, Syngeneic models have been useful in predicting clinical benefit. C57BL/6 mice, 6-8 weeks old, were injected subcutaneously in the left flank with 0.1 mL containing $3 \times 10^5$ LLC cells. When tumors reached an average tumor volume of 50-150 mm³, the mice were matched by tumor size and sorted into control and treatment groups, and dosing initiated (Day 0). Three groups of 10 mice each were established: vehicle control, 10 mg/kg GA2E, and 25 mg/kg GA2E. The mice received one oral dose per day for 13 days. Tumor volumes and weight were measured on days 0, 2, 4, 6, 9, 11, and 13. This study was ended on Day 13, as the average tumor volume was >1500 mm³, and the tumors analyzed by flow cytometry. Two animals in the 10 mg/kg group and one animal in the 25 mg/kg group were terminated early due to ulceration of the tumor.

Figure 18A:
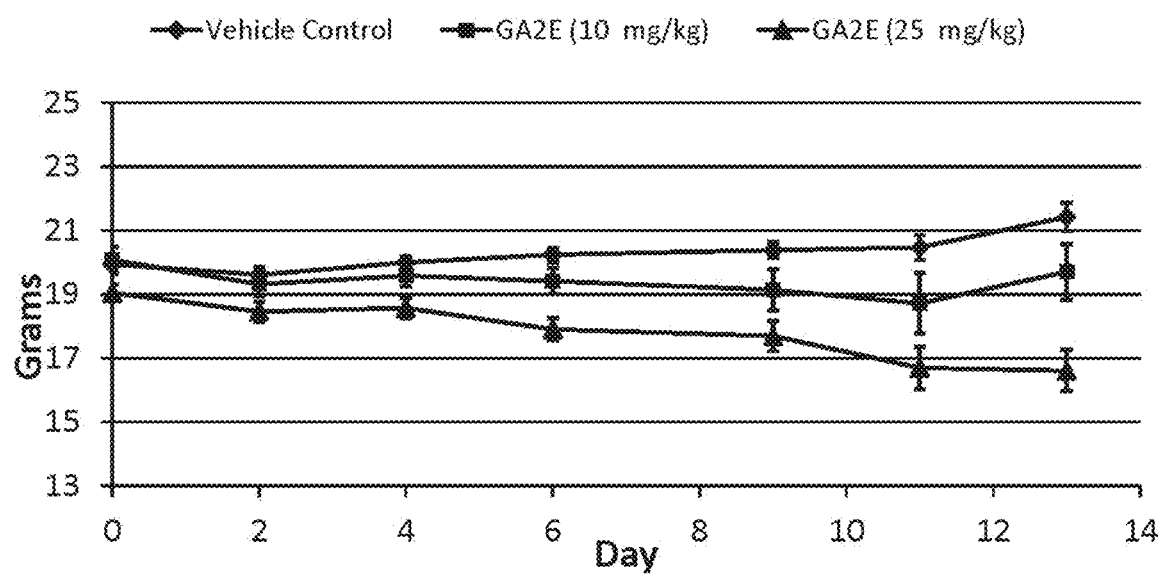
FIGS. 18A-B depict weight change in B57BL/6 mice implanted with LLC cells in control mice (◆) and GA2E treated mice at 10 mg/kg (■) or 25 mg/kg (▲), from the first day of treatment (Day 0) through the end of the study, reported as mass (FIG. 18A) or percent change (FIG. 18B).
Figure 18B:
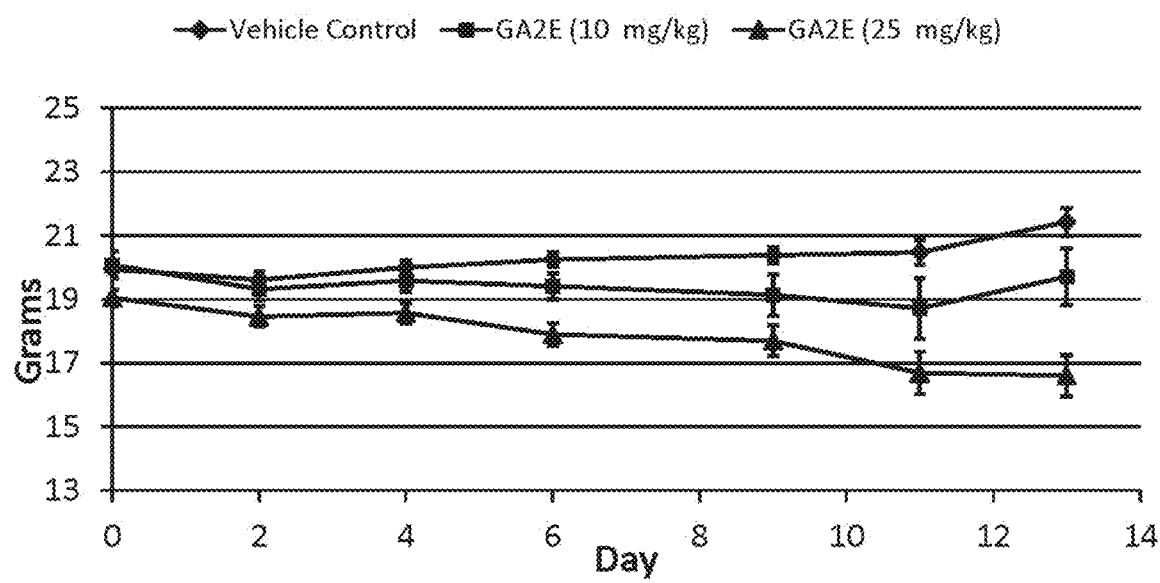
Figure 19:
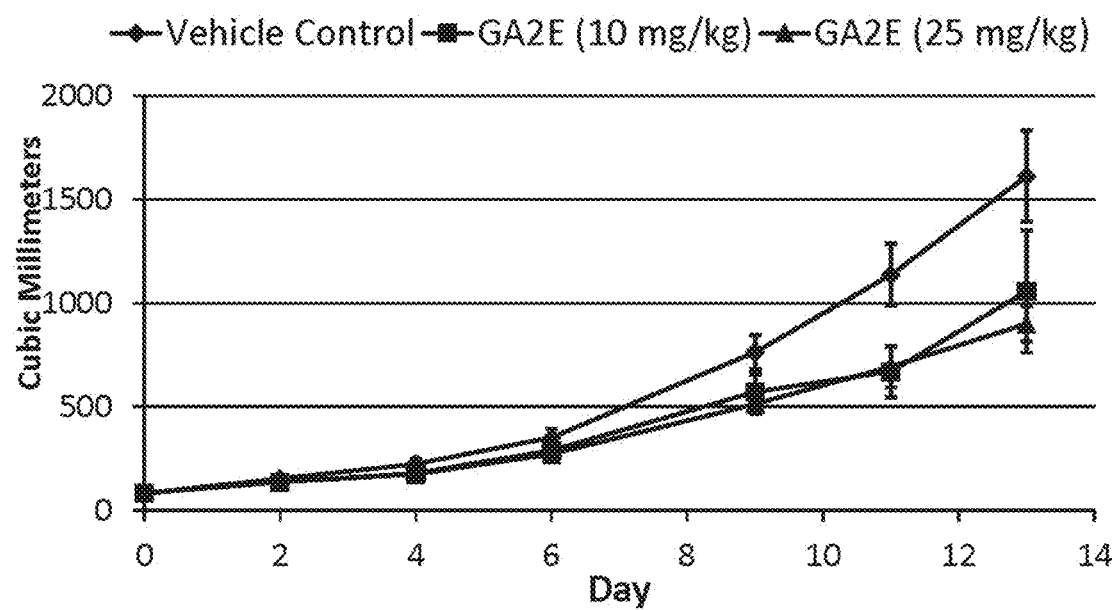
FIG. 19 depicts tumor growth, in mm³, in B57BL/6 mice implanted with LLC cells in control mice (◆) and GA2E treated mice at 10 mg/kg (■) or 25 mg/kg (▲), from the first day of treatment (Day 0) through the end of the study.

The 10 mg/kg dosage of GA2E was well tolerated, with minimal weight loss over the course of the study. The 25 mg/kg dosage of GA2E was less well tolerated, being associated with steady weight loss over the course of the study, exceeding 10% by about Day 10 (FIG. 18A-B). Both dosages of drug inhibited tumor growth, though there was not a significant difference in the tumor inhibition of effect of the two dosages (FIG. 19).

Figure 20:
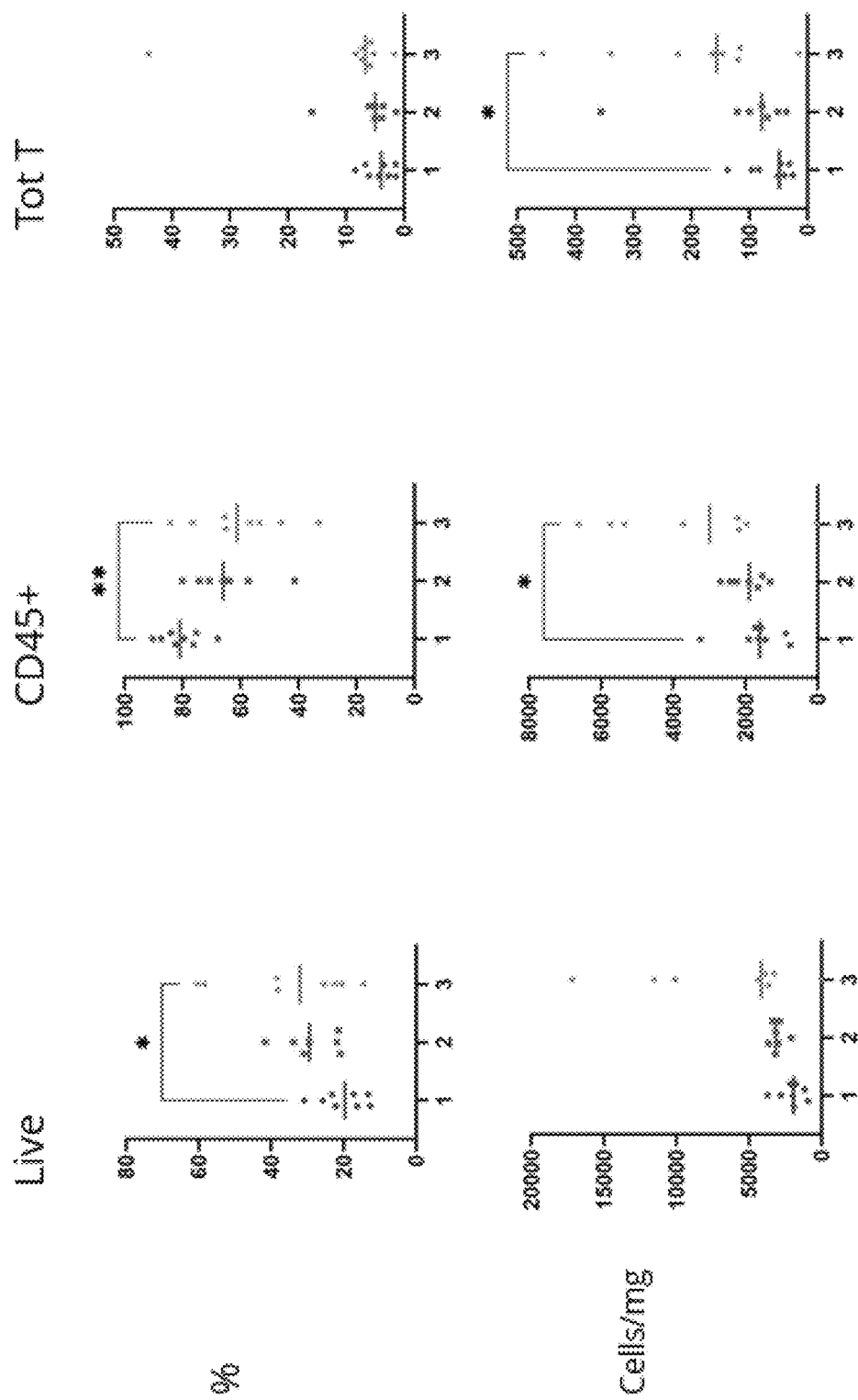
FIG. 20 depicts the results of flow cytometric analysis of LLC tumors excised at the end of the study described in Example 10, for each of the treatments, vehicle control and GA2E at dosages of 10 and 25 mg/kg in columns 1, 2, and 3, respectively, in each panel. Results are shown both as percentage of total T cells (upper panels) and as absolute number of cells pre mg/tumor (lower panels). Depicted are the number of live cells in the tumors and their percentage of the total cells (Live), the number of leukocytes based on CD45 staining and their percentage of the live cells (CD45), and the total number of T cells based on CD3 staining and their percentage of the leukocytes (Tot T).

The mice were sacrificed on Day 13 of the study and the tumors collected and analyzed by flow cytometry. Statistical analysis was by ordinary one-way ANOVA with Tukey's test for significance comparison between groups. Gates were set to identify single cells by forward light scatter, live cells as single cells based on side scatter and staining with the vital stain Fixable Viability Dye eFluor™ 780, white blood cells from live cells based on side scatter and staining with anti-CD45, lymphocytes from white blood cells based on side and forward light scatter, and total T lymphocytes (tot T) from lymphocytes based on side scatter and staining with anti-CD3. Total T lymphocytes were divided into $CD4^+$ (TH) and $CD8^+$ (TC) lymphocytes based on staining with and anti-CD4 and CD8 antibodies and subsets assessed (FIG. 20). The following observations were made on a per-mg of tumor tissue basis.

Figure 21:
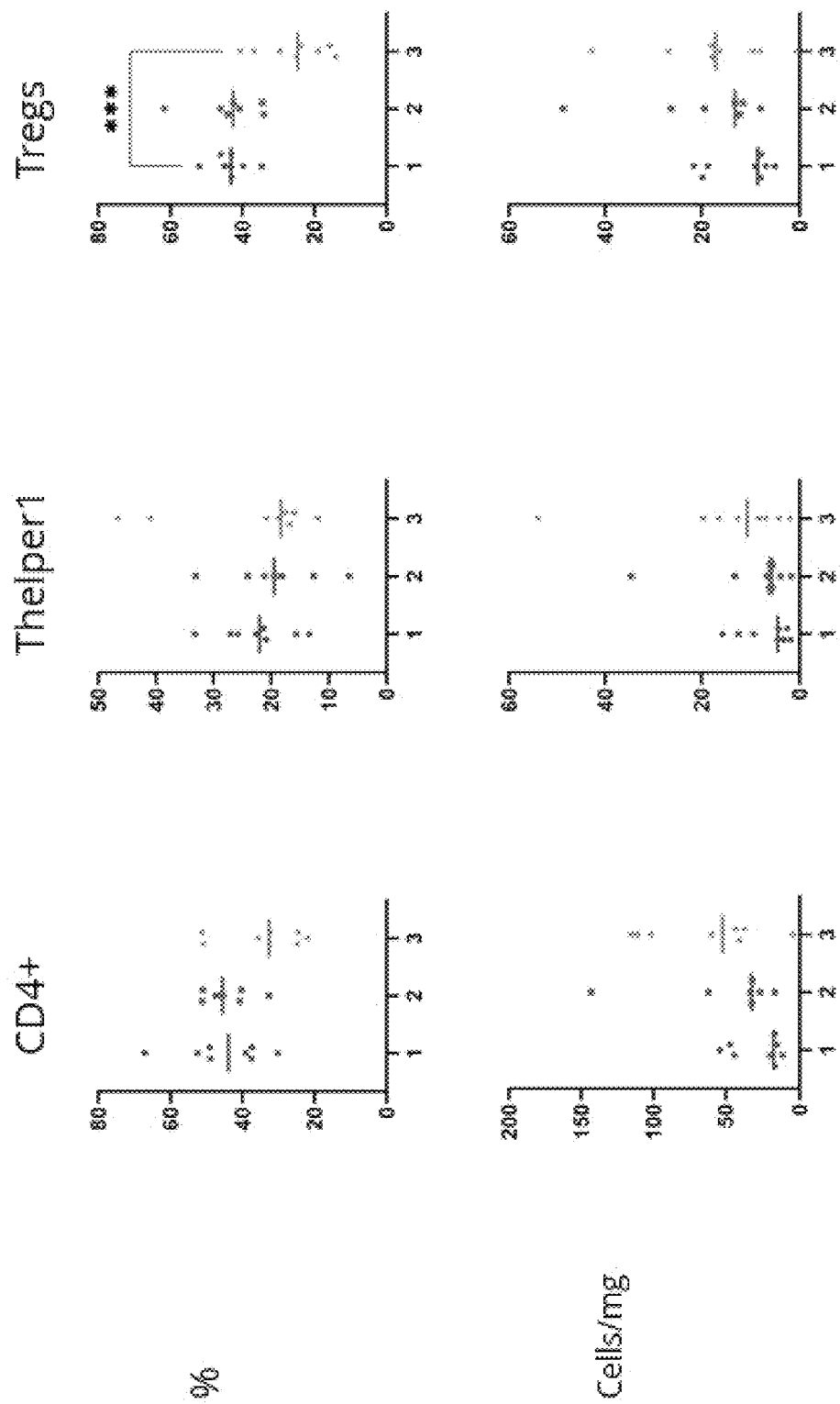
FIG. 21 depicts the results of flow cytometric analysis of LLC tumors excised at the end of the study described in Example 10, for each of the treatments, vehicle control and GA2E at dosages of 10 and 25 mg/kg in columns 1, 2, and 3, respectively, in each panel. Results are shown both as percentage of total T cells (upper panels) and as absolute number of cells pre mg/tumor (lower panels). Depicted are the number of CD4⁺ T cell based on CD4 staining and their percentage of total T cells (CD4+), T helper cells based on positive staining for CD4 and intracellular IFN-γ (Thelper1), and T regulatory cells based on positive staining for CD4, CD25, and FOXP3.
Figure 22:
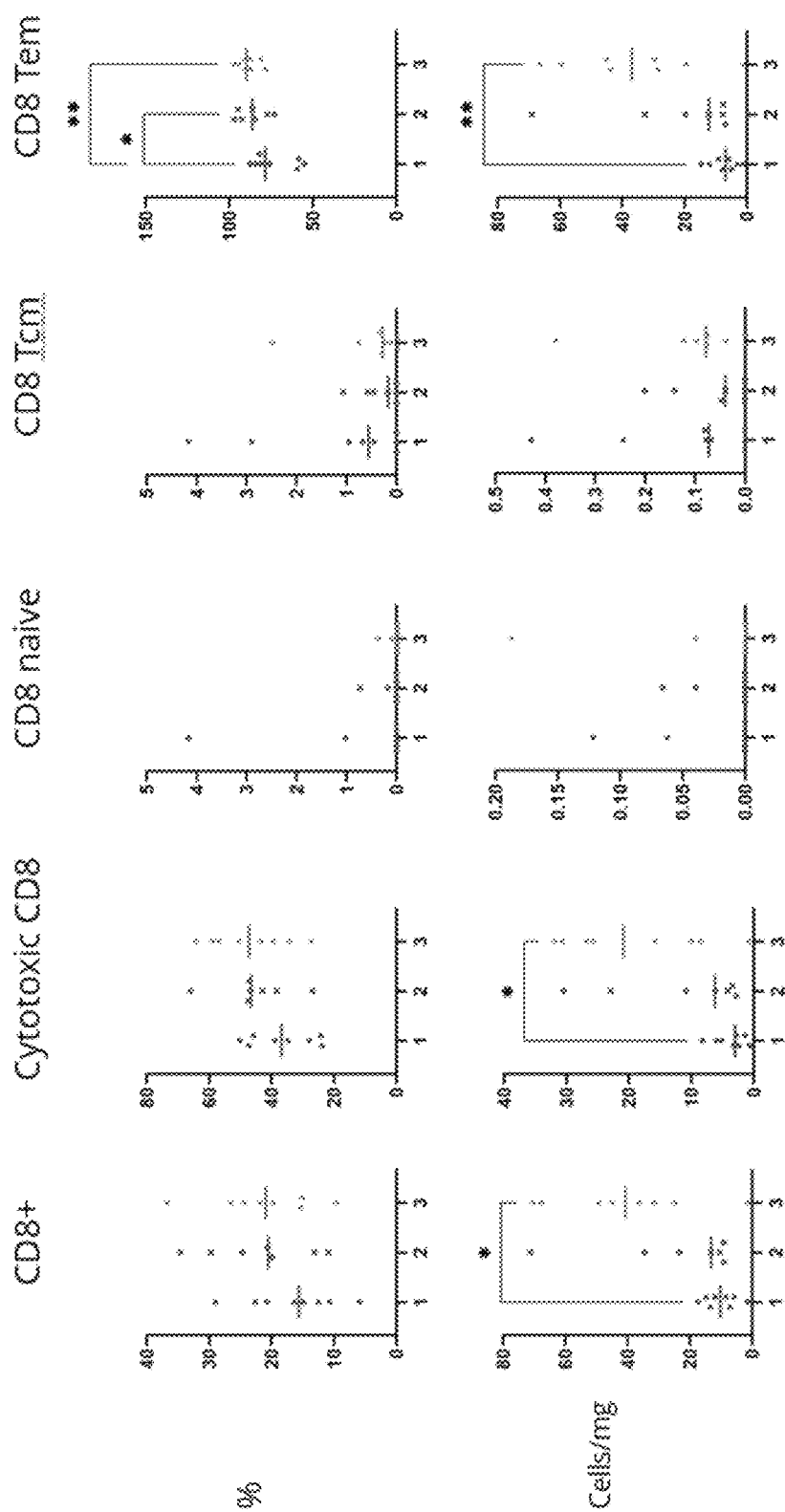
FIG. 22 depicts the results of flow cytometric analysis of LLC tumors excised at the end of the study described in Example 10, for each of the treatments, vehicle control and GA2E at dosages of 10 and 25 mg/kg in columns 1, 2, and 3, respectively, in each panel. Results are shown both as percentage of total T cells (upper panels) and as absolute number of cells pre mg/tumor (lower panels). Depicted are the number of CD8⁺ T cell based on CD8 staining and their percentage of total T cells (CD8⁺), cytotoxic T cells based on positive staining for CD8 and intracellular IFN-γ (Cytotoxic CD8), naïve CD8⁺ T cells based on positive staining for CD8 and CD62L, and negative staining for CD44 (CD8 naïve), CD8⁺ central memory T cells (CD8 Tcm) based on positive staining for CD8, CD62L, and CD44, and CD8⁺ effector memory T cells (CD8 Tem) based on positive staining for CD8 and CD44 and negative staining for CD62L.

The concentration of total $CD8^+$ lymphocytes was increased in the GA2E-treated tumors as compared to controls (FIG. 22, panel CD8+; P<0.05 for the 25 mg/kg dosage). The concentration of cytotoxic cells was also increased (FIG. 22, panel Cytotoxic CD8; P<0.05 for the 25 mg/kg dosage) as was the concentration of effector memory $CD8^+$ T cells in the tumors (FIG. 22, panel CD8 Tem; P<0.01 for the 25 mg/kg dosage). The concentration of naïve and central memory $CD8^+$ T cells in the tumors did not change significantly with the treatment (FIG. 22, panels CD8 naïve and CD8 Tcm, respectively). The concentration of total $CD4^+$ T cells, T helper cells and T regulatory cells in the tumor did not change significantly with the treatment (FIG. 21). However, as a percentage of total T cell the proportion of Treg cells was significantly reduced (FIG. 21, panel Tregs; P<0.001). Accordingly, upon treatment with GA2E, the number of TIL present in the tumors, with phenotypes that should be more effective in killing tumor cells, was expanded.

The Examples demonstrate that RARγ agonists inhibit tumor growth in multiple cancer models including breast cancer ($Her2^+$ and triple negative) and lung cancer cell lines and promote TIL with mouse and human lymphocytes. As the RARγ agonists did not appear to have a tumor growth inhibitory effect in vitro, it is apparent that the tumor growth inhibitory effect observed in vivo is due to increased production and promotion anti-tumor activity of TIL.

Example 11

Pharmacological Activation of RARγ Signaling Using RARγ Agonists has a Cooperative Effect with Immune Checkpoint Inhibitor Antibody in Rejection of B 16 Melanoma Cells The anti-tumor effects of an immune checkpoint inhibitor antibody treatment (such as anti-CTLA-4 antibody) combined with 10 nM of a RARγ agonist disclosed herein are examined in C57BL/6 mice engrafted with B16F10 tumor cells. Mice treated with vehicles only do not show a survival advantage over untreated control mice. Mice treated with both the immune checkpoint inhibitor antibody and RARγ agonist have improved survival at 50 days indicating that these two agents cooperate to eliminate the B16 melanoma cells. Surviving mice that undergo combination treatment are resistant to re-challenge with live tumor cells indicating the effective formation of B16-specific memory cells. Importantly, the anti-melanoma effect is obtained with this combination of drugs without signs of acute or delayed toxicity.

Embodiments

Embodiment 1. A method of treating cancer comprising administering to a patient in need thereof an effective amount RARγ-selective agonist having the structure

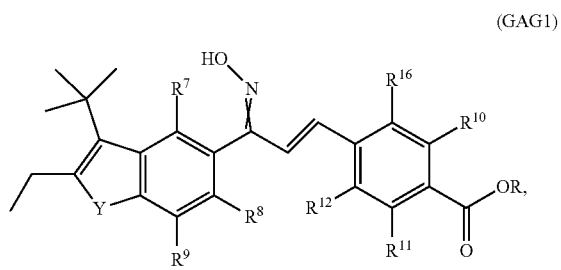

(GAG1)

or a pharmaceutically acceptable salt thereof, wherein R is H or $C_{1-6}$ alkyl; the crossed double bond to the =N—OH group indicates that stereochemistry is not specified; $R^7$ to $R^{12}$ are independently, $C_{1-6}$ alkyl, a hydrogen atom, an alkoxy group, a halogen atom, a nitro group, a hydroxy group, OCF$_3$, or COR$^{13}$, where R$^{13}$ is C$_{1-6}$ alkyl or CF$_3$; Y is oxygen, sulfur, or NR$^{14}$, where R$^{14}$ is C$_{1-6}$ alkyl; and R$^{16}$ is H or F.

Embodiment 2. The method of Embodiment 1, wherein the RARγ-selective agonist has the structure

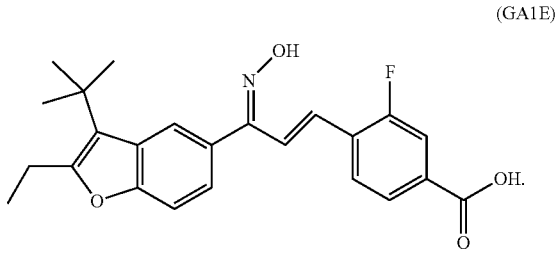 [SMILES: CCc1oc2ccc(C(/C=C/c3ccc(C(=O)O)cc3F)=N/O)cc2c1C(C)(C)C]

(GA1E)

Embodiment 3. The method of Embodiment 1 or 2, wherein the cancer is a solid tumor.
Embodiment 4. The method of Embodiment 3, wherein the cancer is breast cancer.
Embodiment 5. The method of Embodiment 4, wherein the breast cancer is triple negative breast cancer.
Embodiment 6. The method of Embodiment 4, wherein the breast cancer is Her2$^+$ breast cancer.
Embodiment 7. The method of Embodiment 3, wherein the cancer is lung cancer.
Embodiment 8. The method of any one of Embodiments 1-7, wherein the effective amount is about 1 to about 100 mg/day.
Embodiment 9. The method of any one of Embodiments 1-8, further comprising administration of a CAR-T cell.
Embodiment 10. The method of any one of Embodiments 1-8, further comprising administration of an immune checkpoint inhibitor.
Embodiment 11. A method of generating or expanding tumor infiltrating lymphocytes (TIL) by contacting the TIL with a RARγ selective agonist.
Embodiment 12. The method of Embodiment 11, wherein contacting comprises administering the RARγ selective agonist to a subject having cancer.
Embodiment 13. The method of Embodiment 11, wherein contacting comprises culturing the TIL in vitro in a media supplemented with the RARγ selective agonist.
Embodiment 14. The method of Embodiment 13, comprising isolating TIL from a tumor explant.
Embodiment 15. The method of Embodiment 13, comprising culturing peripheral blood mononuclear cells (PBMC) in vitro, in the presence of irradiated tumor cells, in a media supplemented with the RARγ selective agonist.
Embodiment 16. The method of claim 15, wherein the PBMC and the irradiated tumor cells are obtained from the same individual.
Embodiment 17. The method of any one of Embodiments 13-16, wherein the media is further supplemented with IL-2.
Embodiment 18. The method of any one of Embodiments 13-17, further comprising supplementing the culture media with an anti-PD-1 or anti-PD-L1 antibody.
Embodiment 19. A method of treating cancer, comprising infusing the TIL generated or expanded according to any one of claims 11-18 to a patient in need thereof
Embodiment 20. A method of treating cancer, comprising providing RARγ selective agonist-expanded TIL to a patient in need thereof.
Embodiment 21. The method of Embodiment 20, wherein providing comprises administering TIL cultured in vitro in a media supplemented with the RARγ selective agonist.

Embodiment 22. The method of Embodiments 20 or 21, wherein providing comprises administering the RARγ selective agonist to the patient.
Embodiment 23. The method of any one of Embodiments 20-22, wherein the cancer is a solid tumor.
Embodiment 24. The method of Embodiment 23 wherein the cancer is breast cancer.
Embodiment 25. The method of Embodiment 24, wherein the breast cancer is triple negative breast cancer.
Embodiment 26. The method of Embodiment 24, wherein the breast cancer is Her2$^+$ breast cancer.
Embodiment 27. The method of Embodiment 24, wherein the cancer is lung cancer.
Embodiment 28. The method of claim any one of Embodiments 11-27, wherein the RARγ selective agonist is a compound of structure

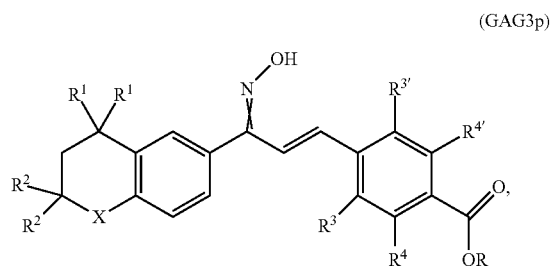

(GAG3p)

or a pharmaceutically acceptable salt thereof, wherein R is H or C$_{1-6}$ alkyl; each R$^1$ and R$^2$ are independently H or C$_{1-6}$ alkyl; R$^3$, R$^{3'}$, R$^4$, and R$^{4'}$ are independently, H or F; X is O, S, CH$_2$, C(R$^5$)$_2$, or NR$^6$, wherein each R$^5$ and R$^6$ are independently H or C$_{1-6}$ alkyl; the crossed double bond to the =N—OH group indicates that stereochemistry is not specified.
Embodiment 29. The method of Embodiment 28, wherein the RARγ selective agonist is a compound of structure

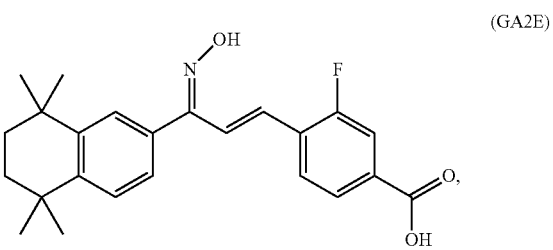 [SMILES: CC1(C)CCC(C)(C)c2cc(C(/C=C/c3ccc(C(=O)O)cc3F)=N/O)ccc21]

(GA2E)

or a pharmaceutically acceptable salt thereof.
Embodiment 30. The method of Embodiment 28, wherein the RARγ selective agonist is a compound of structure

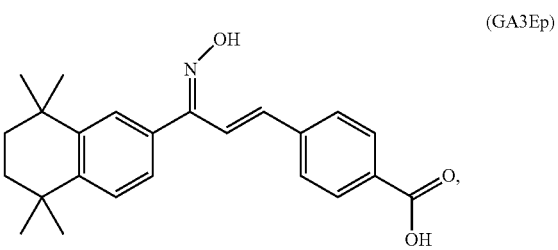 [SMILES: CC1(C)CCC(C)(C)c2cc(C(/C=C/c3ccc(C(=O)O)cc3)=N/O)ccc21]

(GA3Ep)

or a pharmaceutically acceptable salt thereof.

Embodiment 31. The method of any one of Embodiments 19-30, wherein the RARγ selective agonist is a compound of structure

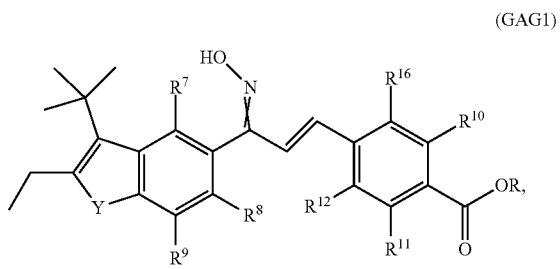

(GAG1)

or a pharmaceutically acceptable salt thereof, wherein R is H or $C_{1-6}$ alkyl; the crossed double bond to the =N—OH group indicates that stereochemistry is not specified; $R^7$ to $R^{12}$ are independently, $C_{1-6}$ alkyl, a hydrogen atom, an alkoxy group, a halogen atom, a nitro group, a hydroxy group, $OCF_3$, or $COR^{13}$, where $R^{13}$ is $C_{1-6}$ alkyl or $CF_3$; Y is oxygen, sulfur, or $NR^{14}$, where $R^{14}$ is $C_{1-6}$ alkyl; and $R^{16}$ is H or F.

Embodiment 32. The method of Embodiment 31, wherein the RARγ-selective agonist has the structure

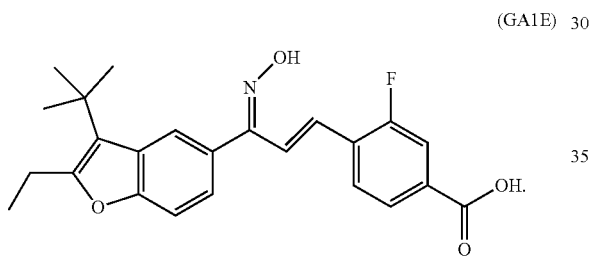

(GA1E)

Embodiment 33. The method of any one of Embodiments 1-10, or 19-32, comprising administering the RARγ selective agonist to a subject, wherein the administering occurs periodically throughout an interval of treatment.

Embodiment 34. The method of any one of Embodiments 1-10, or 19-32, comprising administering the RARγ selective agonist to a subject, wherein the administering occurs in repeated cycles throughout an interval of treatment.

Embodiment 35. The method of Embodiment 34, wherein one cycle of treatment comprises 1) administering the RARγ selective agonist periodically over a first span of time and 2) suspending administration of the RARγ selective agonist over a second span of time, after which a new cycle may be initiated.

Embodiment 36. The method of Embodiment 35, wherein the first span of time is 10-15 days or any integer number of days therein.

Embodiment 37. The method of Embodiments 35 or 36, wherein the second span of time is two weeks to one month or any integer number of days therein.

Embodiment 38. The method of any one of Embodiments 33-37, wherein periodically is daily.

Embodiment 39. The method of any one of Embodiments 33-37, wherein periodically is twice daily.

Embodiment 40. The method of any one of Embodiments 33-37, wherein periodically is every other day.

Embodiment 41. The method of any one of Embodiments 33-40, wherein the interval of treatment extends from a first administration until a complete response is achieved.

Embodiment 42. The method of any one of Embodiments 33-40, wherein the interval of treatment extends from a first administration until the cancer again progresses after stable disease or regression.

Embodiment 43. The method of any one of Embodiments 1-10, or 19-42, further comprising administering an inhibitor of Treg cells.

Embodiment 44. The method of Embodiment 43, wherein the inhibitor of Treg cells comprises a RARα antagonist.

Embodiment 45. The method of Embodiment 43, wherein the inhibitor of Treg cells comprises a Treg-depleting antibody.

Embodiment 46. The method of Embodiment 45, wherein the Treg-depleting antibody comprises an anti-CD25 antibody, an anti-GITR antibody, an anti-FoxP3 antibody, an anti-$CCR_4$ antibody, or an anti-folate receptor 4 antibody.

Embodiment 47. The method of any one of Embodiments 1-8, or 19-46 further comprising administration of an anti-PD-1 or anti-PD-L1 antibody.

Embodiment 48. The method of any one of Embodiments 1-10, or 19-46, further comprising administering an RXR agonist having the structure

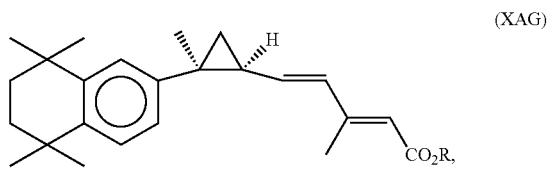

(XAG)

where R is H or $C_{1-6}$ alkyl, or a pharmaceutically acceptable salt thereof.

Embodiment 49. The method of Embodiment 48, wherein the RXR agonist is 3,7-dimethyl-6(S),7(S)-methano,7-[1,1,4,4-tetramethyl-1,2,3,4-tetrahydron-aphth-7-yl]2(E), 4(E) heptadienoic acid (IRX4204).

Embodiment 50. A method of potentiating chimeric antigen receptor-T (CAR-T) cancer immunotherapy comprising administering an effective amount RARγ-selective agonist having the structure

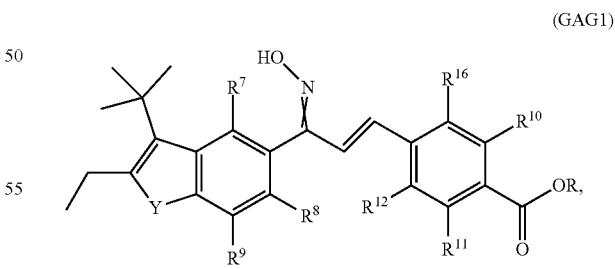

(GAG1)

or a pharmaceutically acceptable salt thereof, wherein R is H or $C_{1-6}$ alkyl; the crossed double bond to the =N—OH group indicates that stereochemistry is not specified; $R^7$ to $R^{12}$ are independently, $C_{1-6}$ alkyl, a hydrogen atom, an alkoxy group, a halogen atom, a nitro group, a hydroxy group, $OCF_3$, or $COR^{13}$, where $R^{13}$ is $C_{1-6}$ alkyl or $CF_3$; Y is oxygen, sulfur, or $NR^{14}$, where $R^{14}$ is $C_{1-6}$ alkyl; and $R^{16}$ is H or F, to a cancer patient who is receiving, has received, or is scheduled to receive, CAR-T cells.

Embodiment 51. A method of potentiating immune checkpoint inhibitor cancer immunotherapy comprising administering an effective amount RARγ-selective agonist having the structure

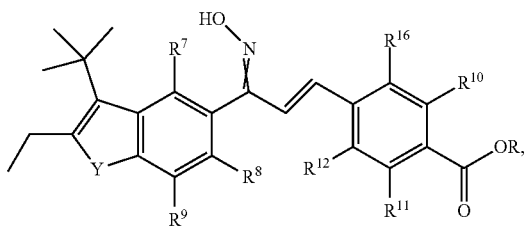

(GAG1)

or a pharmaceutically acceptable salt thereof, wherein R is H or $C_{1-6}$ alkyl; the crossed double bond to the =N—OH group indicates that stereochemistry is not specified; $R^7$ to $R^{12}$ are independently, $C_{1-6}$ alkyl, a hydrogen atom, an alkoxy group, a halogen atom, a nitro group, a hydroxy group, $OCF_3$, or $COR^{13}$, where $R^{13}$ is $C_{1-6}$ alkyl or $CF_3$; Y is oxygen, sulfur, or $NR^{14}$, where $R^{14}$ is $C_{1-6}$ alkyl; and $R^{16}$ is H or F, to a cancer patient who is receiving, has received, or is scheduled to receive, an immune checkpoint inhibitor.

Embodiment 52. A RARγ-selective agonist of the structure:

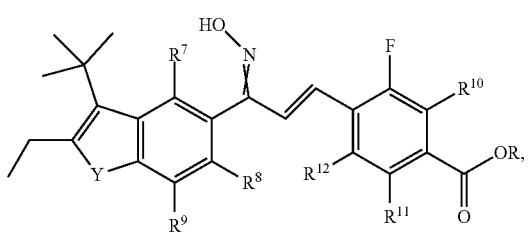

(GAG1)

or a pharmaceutically acceptable salt thereof, wherein R is H or $C_{1-6}$ alkyl; $R^7$ to $R^{12}$ are independently: $C_{1-6}$ alkyl, a hydrogen atom, an alkoxy group, a halogen atom, a nitro group, a hydroxy group, $OCF_3$, or $COR^{13}$, where $R^{13}$ is $C_{1-6}$ alkyl or $CF_3$. Y is oxygen, sulfur, or $NR^{14}$, where $R^{14}$ is $C_{1-6}$ alkyl.

Embodiment 53. The RARγ-selective agonist of Embodiment 52, wherein R is H, methyl, or ethyl.

Embodiment 54. The RARγ-selective agonist of Embodiment 52, wherein Y is O.

Embodiment 55. The RARγ-selective agonist of Embodiment 54 having the following structure:

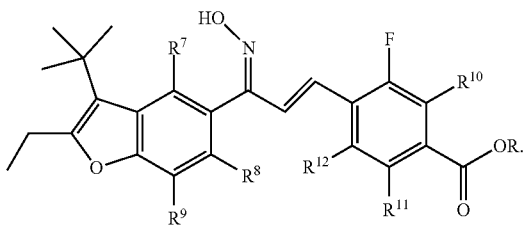

(GAG1-1)

Embodiment 56. The RARγ-selective agonist of Embodiment 52, wherein the =N—OH group is in the E configuration.

Embodiment 57. The RARγ-selective agonist of Embodiment 56 having the following structure:

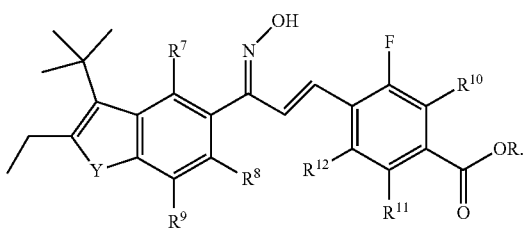

(GAG1-2)

Embodiment 58. The RARγ-selective agonist of Embodiment 52, wherein the RARγ selective agonist is 4-((1E,3E)-3-(3-(tert-butyl)-2-ethyl-benzofuran-5-yl)-3-(hydroxyimino)prop-1-en-1-yl)-3-fluorobenzoic acid (GA1E), having the structure

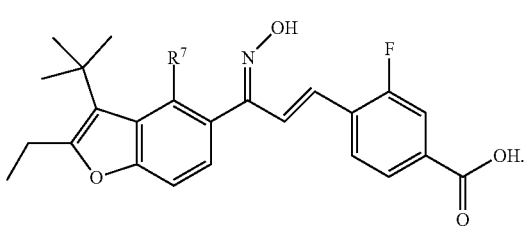

(GA1E)

Embodiment 59. The RARγ-selective agonist of Embodiment 52, wherein the RARγ selective agonist is 4-((1E,3Z)-3-(3-(tert-butyl)-2-ethyl=benzofuran-5-yl)-3-(hydroxyimino)prop-1-en-1-yl)-3-fluorobenzoic acid (GA1Z), having the structure

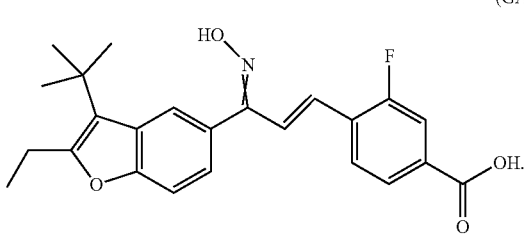

(GA1Z)

Embodiment 60. A RARγ-selective agonist having the structure

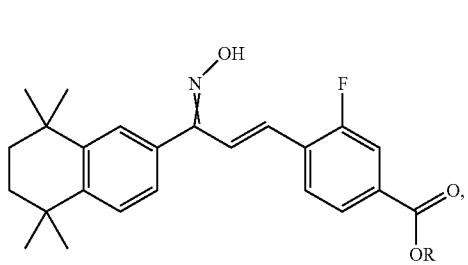
(GAG2)

or a pharmaceutically acceptable salt thereof, wherein R is H or $C_{1-6}$ alkyl, and the crossed double bond to the =N—OH group indicates that stereochemistry is not specified.

Embodiment 61. The RARγ-selective agonist of Embodiment 60, wherein R is H, methyl, or ethyl.

Embodiment 62. The RARγ-selective agonist of Embodiment 60, wherein the =N—OH group is in the E configuration.

Embodiment 63. The RARγ-selective agonist of Embodiment 60, wherein the RARγ selective agonist is 3-fluoro-4-((1E,3E)-3-(hydroxyimino)-3-(5,5,8,8-tetramethyl-5,6,7,8-tetrahydronaphthalen-2-yl)prop-1-en-1-yl)benzoic acid (GA2E), having the structure

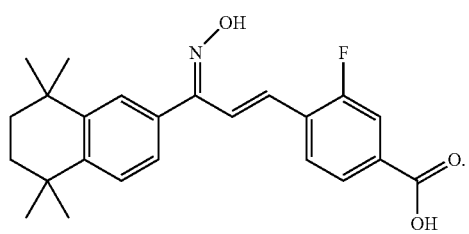
(GA2E)

Embodiment 64. The RARγ-selective agonist of Embodiment 60, wherein the RARγ selective agonist is 3-fluoro-4-((1E,3Z)-3-(hydroxyimino)-3-(5,5,8,8-tetramethyl-5,6,7,8-tetrahydronaphthalen-2-yl)prop-1-en-1-yl)benzoic acid (GA2Z), having the structure

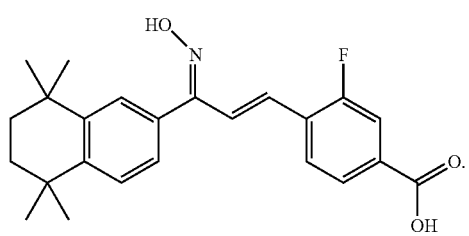
(GA2Z)

Embodiment 65. A RARγ-selective agonist having the structure

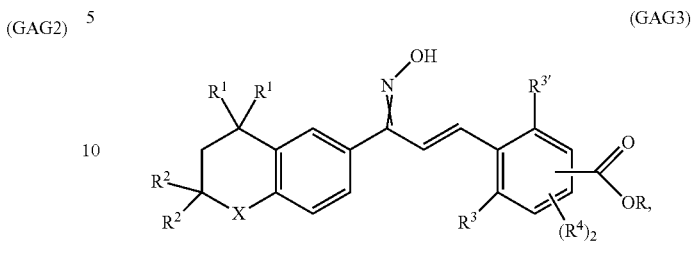
(GAG3)

or a pharmaceutically acceptable salt thereof, wherein R is H or $C_{1-6}$ alkyl; each $R^1$ and $R^2$ are independently H or $C_{1-6}$ alkyl; $R^3$ and $R^{3'}$ are independently H, or halogen; $(R^4)_2$ comprises $R^4$ and $R^{4'}$ which are independently H, halogen, $C_{1-6}$ alkyl or $C_{1-6}$ alkoxy; X is O, S, $CH_2$, $C(R^5)_2$, or $NR^6$, wherein each $R^5$ and $R^6$ are independently H or $C_{1-6}$ alkyl; the crossed double bond to the =N—OH group indicates that stereochemistry is not specified; and the COOR group is in the meta or para position and the two $R^4$ groups occupy the remaining positions on the ring.

Embodiment 66. The RARγ-selective agonist of Embodiment 65, having the structure

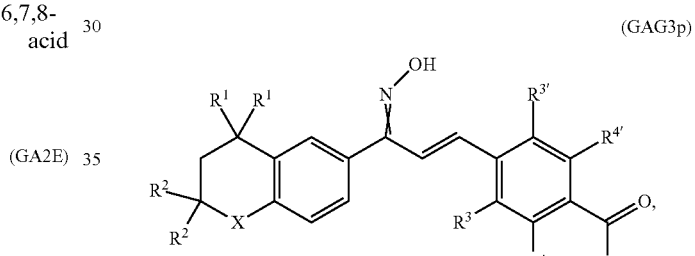
(GAG3p)

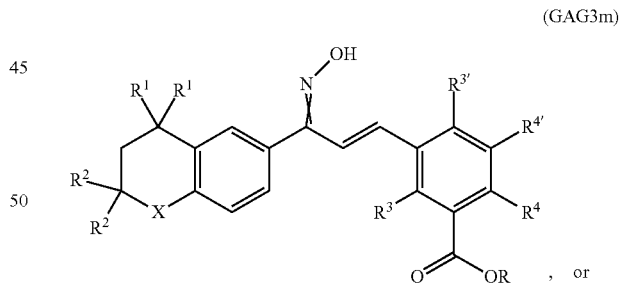
(GAG3m)

, or

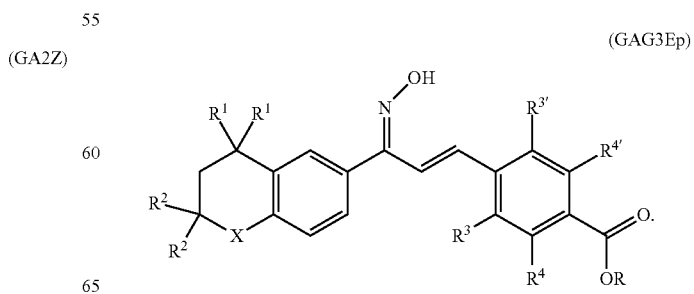
(GAG3Ep)

Embodiment 67. The RARγ-selective agonist of Embodiment 65, having the structure

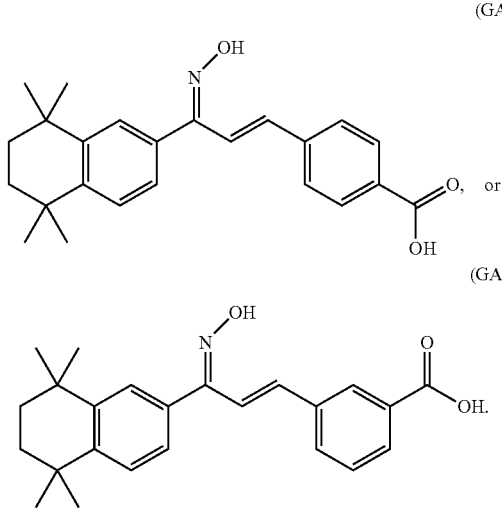

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed.

No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating cancer comprising administering to a patient in need thereof an effective amount of an RARγ-selective agonist of the structure:

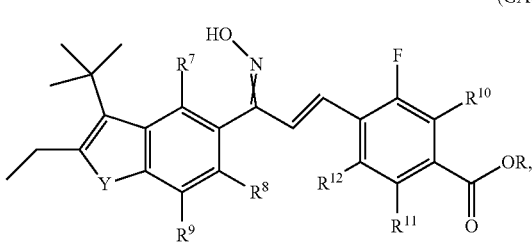

(GAG1)

or a pharmaceutically acceptable salt thereof, wherein R is H or $C_{1-6}$ alkyl; $R^7$ to $R^{12}$ are independently $C_{1-6}$ alkyl, a hydrogen atom, an alkoxy group, a halogen atom, a nitro group, a hydroxy group, $OCF_3$, or $COR^{13}$, wherein $R^{13}$ is $C_{1-6}$ alkyl or CF; Y is oxygen, sulfur, or $NR_{14}$, wherein $R_{14}$ is $C_{1-6}$ alkyl; and the crossed double bond to the =N—OH group indicates that stereochemistry is not specified.

2. The method of claim 1, wherein the cancer is breast cancer or lung cancer.

3. The method of claim 2, wherein the breast cancer is triple negative breast cancer.

4. The method of claim 3, wherein the breast cancer is Her2$^+$ breast cancer.

5. The method of claim 1, wherein the effective amount is about 1 to about 100 mg/day.

6. The method of claim 1, further comprising administration of a CAR-T cell or an immune checkpoint inhibitor.

7. The method of claim 1, comprising administering the RARγ selective agonist periodically throughout an interval of treatment or in repeated cycles throughout an interval of treatment.

8. The method of claim 7, wherein periodically is daily, twice daily, or ever other day.

9. A method of treating cancer, comprising infusing tumor infiltrating lymphocytes (TIL) generated or expanded, wherein the TIL are generated or expanded by contacting the TIL with an RARγ selective agonist of the structure:

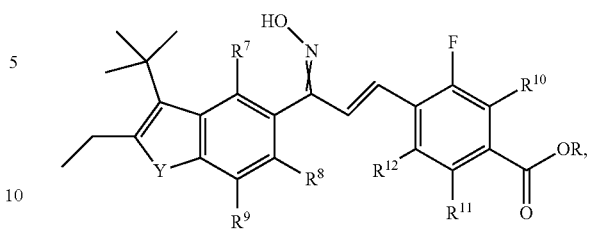

(GAG1)

or a pharmaceutically acceptable salt thereof, wherein R is H or $C_{1-6}$ alkyl; $R^7$ to $R^{12}$ are independently $C_{1-6}$ alkyl, a hydrogen atom, an alkoxy group, a halogen atom, a nitro group, a hydroxy group, $OCF_3$, or $COR^{13}$, wherein $R^{13}$ is $C_{1-6}$ alkyl or CF; Y is oxygen, sulfur, or $NR_{14}$, wherein $R_{14}$ is $C_{1-6}$ alkyl; and the crossed double bond to the =N—OH group indicates that stereochemistry is not specified.

10. The method of claim 9, wherein the TIL are cultured in vitro in a media supplemented with the RARγ selective agonist.

11. The method of claim 9, comprising isolating TIL from a tumor explant.

12. The method of claim 9, comprising culturing peripheral blood mononuclear cells (PBMC) in vitro, in the presence of irradiated tumor cells, in a media supplemented with the RARγ selective agonist.

13. The method of claim 12, wherein the PBMC and the irradiated tumor cells are obtained from the same individual.

14. The method of claim 1, wherein R is H, methyl, or ethyl.

15. The method of claim 1, wherein Y is O.

16. The method of claim 1, wherein the =N—OH group is in the E configuration.

17. The method of claim 1, wherein the RARγ selective agonist is 4-((1E,3E)-3-(3-(tert-butyl)-2-ethyl-benzofuran-5-yl)-3-(hydroxyimino)prop-1-en-1-yl)-3-fluorobenzoic acid

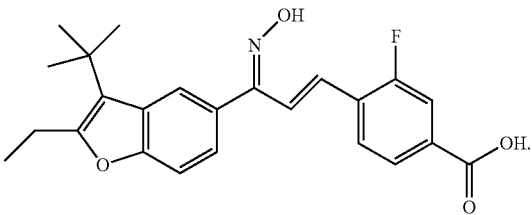

(GA1E)

* * * * *